(12) United States Patent
Shoenfeld et al.

(10) Patent No.: US 10,842,844 B2
(45) Date of Patent: *Nov. 24, 2020

(54) PHOSPHORYLCHOLINE CONJUGATES AND USES THEREOF

(71) Applicant: TPCERA LTD., Jerusalem (IL)

(72) Inventors: Yehuda Shoenfeld, Ramat Gan (IL); Miriam Blank, Tel Aviv (IL)

(73) Assignee: TPCERA LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/101,781

(22) Filed: Aug. 13, 2018

(65) Prior Publication Data

US 2018/0353566 A1    Dec. 13, 2018

Related U.S. Application Data

(63) Continuation of application No. 14/956,167, filed on Dec. 1, 2015, now Pat. No. 10,046,021, which is a continuation-in-part of application No. 14/766,108, filed as application No. PCT/IL2014/050124 on Feb. 5, 2014, now Pat. No. 9,987,372.

(60) Provisional application No. 61/760,668, filed on Feb. 5, 2013.

(51) Int. Cl.
| | | |
|---|---|---|
| A61K 38/08 | (2019.01) | |
| A61K 38/07 | (2006.01) | |
| A61K 47/64 | (2017.01) | |
| A61K 47/54 | (2017.01) | |

(52) U.S. Cl.
CPC ............. *A61K 38/07* (2013.01); *A61K 38/08* (2013.01); *A61K 47/544* (2017.08); *A61K 47/548* (2017.08); *A61K 47/64* (2017.08); *A61K 47/646* (2017.08)

(58) Field of Classification Search
None
See application file for complete search history.

(56) References Cited

U.S. PATENT DOCUMENTS

| | | | |
|---|---|---|---|
| 5,455,032 A | 10/1995 | Kinney | |
| 7,067,480 B2 | 6/2006 | Harnett | |
| 7,097,824 B2 | 8/2006 | Sharma | |
| 8,012,483 B2 | 9/2011 | De Faire | |
| 9,987,372 B2 | 6/2018 | Shoenfeld et al. | |
| 10,046,021 B2 * | 8/2018 | Shoenfeld ............. | A61K 47/64 |
| 2008/0175852 A1 | 7/2008 | Rezanka | |
| 2010/0210567 A1 | 8/2010 | Bevec | |
| 2010/0303721 A1 | 12/2010 | Weinstock et al. | |
| 2011/0166250 A1 | 7/2011 | Pacetti | |

FOREIGN PATENT DOCUMENTS

| | | |
|---|---|---|
| EP | 2258728 A1 | 12/2010 |
| EP | 2260873 A1 | 12/2010 |
| WO | 03024474 A2 | 3/2003 |
| WO | 2005052115 A2 | 6/2005 |
| WO | 2006003518 A2 | 1/2006 |
| WO | 2014122646 A1 | 8/2014 |

OTHER PUBLICATIONS

Uniprot entry for hemocyanin (retrieved from http://www.uniprot.org/uniprot/Q53IP9 on Mar. 15, 2017, 8 pages).
Rossomando et al: "Characterization and cAMP inhibition of a lysyl-(N-e:-5'-phospho) adenosyl phosphoamidase in Dictyostelium discoideum"; International Journal of Biochemistry; vol. 18, Issue 5, 1986, pp. 481-484.
Singhal et al. ('Specific interaction of liposomes with PMN leukocytes upon incorporating tuftsan in their bilayers' FEBS etters, v 178(1), Dec. 1984, pp. 109-113).
AOCS lipid library (retrieved from http:I/lipidlibrary.aocs.org/Primer/content.cfm?itemnumber=39351 on Apr. 18, 2017, 13 pages).
Pubchem entry (retrieved from http://pubchem.ncbi.nlm.nih.gov/compound/phosphocholine#section=top on Apr. 18, 2017, 26 pages).
Bashi, Tomer, et al. "Novel therapeutic compound tuftsin-phosphorylcholine attenuates collagen-induced arthritis." Clinical & Experimental Immunology (Feb. 4, 2016).
Anthony et al., (2007) Protective immune mechanisms in helminth infection. Nat Rev Immunol 7(12): 975-87.
Bhasin et al., (2007) Modulation of microglial/macrophage activation by macrophage inhibitory factor (TKP) or tuftsin TKPR) attenuates the disease course of experimental autoimmune encephalomyelitis_ BMC Immunol 8: 10.
Blank et al., (1999) Prevention of experimental antiphospholipid syndrome and endothelial cell activation by synthetic peptides. Proc Natl Acad Sci US A 96(9): 5164-8.
Chen et al., (2009) Regulation of dendritic cells and macrophages by an anti-apoptotic cell natural antibody that suppresses TLR responses and inhibits inflammatory arthritis. J Immunol 183(2): 1346-59.
Chilton et al., (2004) Flt3-ligand treatment prevents diabetes in NOD mice. Diabetes 53(8): 1995-2002.
Dagan et al., (1987) Tuftsin and tuftsin conjugates potentiate immunogenic processes: effects and possible mechanisms. J Biol Response Mod 6(6): 625-36.
Elliott and Weinstock (2009) Helminthic therapy: using worms to treat immune-mediated disease. Adv Exp Med Biol 566: 157-66.
Goodridge et al., (2007) Phosphorylcholine mimics the effects of ES-62 on macrophages and dendritic cells. Parasite Immunol 29(3): 127-37.
Harnett and Harnett (2009) Immunomodulatory activity and therapeutic potential of the filarial nematode secreted product, ES-62. Adv Exp Med Biol 666: 88-94.

(Continued)

*Primary Examiner* — Ronald T Niebauer
(74) *Attorney, Agent, or Firm* — The Roy Gross Law Firm, LLC; Roy Gross

(57) ABSTRACT

The present invention provides phosphorylcholine conjugates and pharmaceutical compositions comprising same for the prevention or treatment of autoimmune diseases. In particular, the conjugates of the present invention are effective in treating autoimmune diseases associated with pathological inflammation.

20 Claims, 45 Drawing Sheets

Specification includes a Sequence Listing.

(56) References Cited

OTHER PUBLICATIONS

Harnett et al., (2008) The phosphorycholine moiety of the filarial nematode immunomodulator ES-62 is responsible for its anti-inflammatory action in arthritis. Ann Rheum Dis 67(4): 518-23.

Harnett et al., (2010) The therapeutic potential of the filarial nematode-derived immunodulator, ES-62 in inflammatory disease. Clin Exp Immunol 159(3): 256-67.

Harris and Gause (2011) To B or not to B: B cells and the Th2-type immune response to helminths. Trends Immunol 32(2): 80-8.

Houston et al., (2008) Gene inactivation confirms the identity of enzymes involved in nematode phosphorylcholine-Nglycan synthesis. Mal Biochem Parasitol 157(1): 88-91.

Jackson et al., (2009) Review series on helminths, immune modulation and the hygiene hypothesis: immunity against helminths and immunological phenomena in modem human populations: coevolutionary legacies? Immunology 126(1) 18-27.

Kataoka et al., (2011) The nasal dendritic cell-targeting Flt3 ligand as a safe adjuvant elicits effective protection against fatal pneumococcal pneumonia. Infect Immun 79(7): 2819-28.

Krause et al., (1999) Inhibition of diabetes in NOD mice by idiotypic induction of SLE J Autoimmun 13(1): 49-55.

Kuijk and van Die (2010) Worms to the rescue: can worm glycans protect from autoimmune diseases? IUBMB Life 62(4): 303-12.

Liu et al., (2009) Helminth infection can reduce insulitis and type 1 diabetes through CD25- and IL-10-independent mechanisms. Infect Immun 77(12): 5347-58.

Lukas et al., (1984) Stimulating effect of tuftsin and its analogues on the defective monocyte chemotaxis in systemic upus erythematosus. Immunopharmacology 7(3-4): 171-8.

McInnes et al., (2003) A novel therapeutic approach targeting articular inflammation using the filarial nematode-derived phosphorylcholine-containing glycoprotein ES-62. J Immunol 171(4): 2127-33.

Osada et al., (2010) Schistosoma mansoni infection reduces severity of collagen-induced arthritis via down-regulation of pro-inflammatory mediators. Int J Parasitol 39(4): 457-64.

Poltl et al., (2007) N-glycans of the porcine nematode parasite Ascaris suum are modified with phosphorylcholine and core fucose residues. FEBS J 274(3): 714-26.

Ruyssers et al., (2010) Schistosoma mansoni proteins attenuate gastrointestinal motility disturbances during experimental colitis in mice. World J Gastroenterol 16(6): 703-12.

Sewell et al., (2003) Immunomodulation of experimental autoimmune encephalomyelitis by helminth ova immunization. Int Immunol 15(1): 59-69.

Shaw et al., (2003) The autoreactivity of anti-phosphorylcholine antibodies for atherosclerosis-associated neo-antigens and apoptotic cells. J Immunol 170(12): 6151-7.

Shoenfeld et al., (2002) Efficacy of IVIG affinity-purified anti-double-stranded DNA anti-idiotypic antibodies in the treatment of an experimental murine model of systemic lupus erythematosus. Int Immunol 14(11 ): 1303-11.

Summers et al., (2005) Trichuris suis therapy for active ulcerative colitis: a randomized controlled trial. Gastroenterology 128(4): 825-32.

Summers et al., (2005) Trichuris suis therapy in Crohn's disease. Gut 54(1): 87-90.

Tanaka et at, (2007) Intranasal immunization with phosphorylcholine induces antigen specific mucosal and systemic Immune responses in mice. Vaccine 25(14): 2680-7.

Wilson and Maizels (2004) Regulation of allergy and autoimmunity in helminth infection. Clin Rev Allergy Immunol 26(1): 35-50.

Bashi et al. Successful modulation of murine lupus nephritis with tuftsin-phosphorylcholine Journal of Autoimmunity v59 2015 pp. 1-7.

Gottlieb et al. Tuftsin analogs for probing its specific receptor site on phagocytic cells Eur. J. Biochem. v125 1982 pp. 631-638.

Shor et al. Phosphorylcholine-tuftsin compound prevents development of dextransulfate-sodium-salt induced murine colitis: Implications for the treatment of human inflammatory bowel disease Journal of Autoimmunity v56 2015 pp. 111-117.

Goodridge et al., "In vivo exposure of murine dendritic cell and macrophage bone marrow progenitors to the phosphorylcholine-containing filarial nematode glycoprotein ES-62 polarizes their differentiation to an anti-inflammatory phenotype" Immunology 113 491-498. 2004.

Jia et al., "Polyamidoamine dendrimers surface-engineered with biomimetic phosphorylcholine as potential drug delivery carriers" Colloids and Surfaces B: Biointerfaces 84 49-54 2011.

* cited by examiner

SEQUENCE LISTING

```
<160> NUMBER OF SEQ ID NOS: 40

<210> SEQ ID NO 1
<211> LENGTH: 16
<212> TYPE: DNA
<213> ORGANISM: Artificial
<220> FEATURE:
<223> OTHER INFORMATION: Synthetic

<400> SEQUENCE: 1
gaacgctaca cactgc                                                         16

<210> SEQ ID NO 2
<211> LENGTH: 16
<212> TYPE: DNA
<213> ORGANISM: Artificial
<220> FEATURE:
<223> OTHER INFORMATION: Synthetic

<400> SEQUENCE: 2
ctggacctgt gggttg                                                         16

<210> SEQ ID NO 3
<211> LENGTH: 17
<212> TYPE: DNA
<213> ORGANISM: Artificial
<220> FEATURE:
<223> OTHER INFORMATION: Synthetic

<400> SEQUENCE: 3
ccccaactgg taaatca                                                        17

<210> SEQ ID NO 4
<211> LENGTH: 17
<212> TYPE: DNA
<213> ORGANISM: Artificial
<220> FEATURE:
<223> OTHER INFORMATION: Synthetic

<400> SEQUENCE: 4
ccgaggacta aggagtg                                                        17
```

```
<210> SEQ ID NO 5
<211> LENGTH: 18
<212> TYPE: DNA
<213> ORGANISM: Artificial
<220> FEATURE:
<223> OTHER INFORMATION: Synthetic

<400> SEQUENCE: 5
aacctcgttt gtacctct                                                 18

<210> SEQ ID NO 6
<211> LENGTH: 16
<212> TYPE: DNA
<213> ORGANISM: Artificial
<220> FEATURE:
<223> OTHER INFORMATION: Synthetic

<400> SEQUENCE: 6
caccatagca aagggc                                                   16

<210> SEQ ID NO 7
<211> LENGTH: 20
<212> TYPE: DNA
<213> ORGANISM: Artificial
<220> FEATURE:
<223> OTHER INFORMATION: Synthetic

<400> SEQUENCE: 7
gggcaaggga tgctctctag                                               20

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
ctgaagctgc tgcagagctg                                               20

<210> SEQ ID NO 9
<211> LENGTH: 17
<212> TYPE: DNA
<213> ORGANISM: Artificial
<220> FEATURE:
<223> OTHER INFORMATION: Synthetic

<400> SEQUENCE: 9
acgtcgtagc aaaccac                                                  17

<210> SEQ ID NO 10
<211> LENGTH: 17
<212> TYPE: DNA
<213> ORGANISM: Artificial
<220> FEATURE:
<223> OTHER INFORMATION: Synthetic

<400> SEQUENCE: 10
agatagcaaa tcggctg                                                  17

<210> SEQ ID NO 11
<211> LENGTH: 16
<212> TYPE: DNA
<213> ORGANISM: Artificial
<220> FEATURE:
<223> OTHER INFORMATION: Synthetic
```

```
<400> SEQUENCE: 11 gaaccccat tgctgt                                                    16

<210> SEQ ID NO 12
<211> LENGTH: 16
<212> TYPE: DNA
<213> ORGANISM: Artificial
<220> FEATURE:
<223> OTHER INFORMATION: Synthetic

<400> SEQUENCE: 12
gccctgtatt ccgtct                                                   16

<210> SEQ ID NO 13
<211> LENGTH: 18
<212> TYPE: DNA
<213> ORGANISM: Artificial
<220> FEATURE:
<223> OTHER INFORMATION: Synthetic

<400> SEQUENCE: 13
taccacaata tgcgaccc                                                 18

<210> SEQ ID NO 14
<211> LENGTH: 20
<212> TYPE: DNA
<213> ORGANISM: Artificial
<220> FEATURE:
<223> OTHER INFORMATION: Synthetic

<400> SEQUENCE: 14
ctcaaattca tctacggtcc                                               20

<210> SEQ ID NO 15
<211> LENGTH: 16
<212> TYPE: DNA
<213> ORGANISM: Artificial
<220> FEATURE:
<223> OTHER INFORMATION: Synthetic

<400> SEQUENCE: 15
gtgacgttga catccg                                                   16

<210> SEQ ID NO 16
<211> LENGTH: 16
<212> TYPE: DNA
<213> ORGANISM: Artificial
<220> FEATURE:
<223> OTHER INFORMATION: Synthetic

<400> SEQUENCE: 16
cagtaacagt ccgcct                                                   16

<210> SEQ ID NO 17
<211> LENGTH: 4
<212> TYPE: PRT
<213> ORGANISM: Artificial
<220> FEATURE:
<223> OTHER INFORMATION: Synthetic

<400> SEQUENCE: 17

Thr Lys Pro Arg
1
```

```
<210> SEQ ID NO 18
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is absent or Arg.

<400> SEQUENCE: 18

Thr Lys Pro Xaa
1

<210> SEQ ID NO 19
<211> LENGTH: 5
<212> TYPE: PRT
<213> ORGANISM: Artificial
<220> FEATURE:
<223> OTHER INFORMATION: Synthetic

<400> SEQUENCE: 19

Thr Lys Pro Pro Arg
1               5

<210> SEQ ID NO 20
<211> LENGTH: 4
<212> TYPE: PRT
<213> ORGANISM: Artificial
<220> FEATURE:
<223> OTHER INFORMATION: Synthetic

<400> SEQUENCE: 20

Ser Lys Pro Arg
1

<210> SEQ ID NO 21
<211> LENGTH: 4
<212> TYPE: PRT
<213> ORGANISM: Artificial
<220> FEATURE:
<223> OTHER INFORMATION: Synthetic

<400> SEQUENCE: 21

Thr Arg Pro Arg
1

<210> SEQ ID NO 22
<211> LENGTH: 4
<212> TYPE: PRT
<213> ORGANISM: Artificial
<220> FEATURE:
<223> OTHER INFORMATION: Synthetic

<400> SEQUENCE: 22

Ser Lys Pro Lys
1

<210> SEQ ID NO 23
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Gly, Ala, Leu, Val, Arg, His, Lys, Ser,
```

```
        Thr, Asn, Gln, Ile, Met, or any non-natural, non-charged and
        non-polar amino acid.
<220> FEATURE:
<221> NAME/KEY: MISC_FEATURE
<222> LOCATION: (6)..(6)
<223> OTHER INFORMATION: Xaa is His or Tyr.

<400> SEQUENCE: 23

Thr Lys Pro Arg Xaa Xaa
1               5

<210> SEQ ID NO 24
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Gly, Ala, Leu, Val, Arg, His, Lys, Ser,
        Thr, Asn, Gln, Ile, Met, or any non-natural, non-charged and
        non-polar amino acid.
<220> FEATURE:
<221> NAME/KEY: MISC_FEATURE
<222> LOCATION: (2)..(2)
<223> OTHER INFORMATION: Xaa is His or Tyr.

<400> SEQUENCE: 24

Xaa Xaa Thr Lys Pro Arg
1               5

<210> SEQ ID NO 25
<211> LENGTH: 6
<212> TYPE: PRT
<213> ORGANISM: Artificial
<220> FEATURE:
<223> OTHER INFORMATION: Synthetic

<400> SEQUENCE: 25

Thr Lys Pro Arg Gly Tyr
1               5

<210> SEQ ID NO 26
<211> LENGTH: 6
<212> TYPE: PRT
<213> ORGANISM: Artificial
<220> FEATURE:
<223> OTHER INFORMATION: Synthetic

<400> SEQUENCE: 26

Thr Lys Pro Arg Gly His
1               5

<210> SEQ ID NO 27
<211> LENGTH: 6
<212> TYPE: PRT
<213> ORGANISM: Artificial
<220> FEATURE:
<223> OTHER INFORMATION: Synthetic

<400> SEQUENCE: 27

Thr Lys Pro Arg Ala Tyr
1               5

<210> SEQ ID NO 28
<211> LENGTH: 6
<212> TYPE: PRT
<213> ORGANISM: Artificial
```

```
<220> FEATURE:
<223> OTHER INFORMATION: Synthetic

<400> SEQUENCE: 28

Thr Lys Pro Arg Ala His
1               5

<210> SEQ ID NO 29
<211> LENGTH: 6
<212> TYPE: PRT
<213> ORGANISM: Artificial
<220> FEATURE:
<223> OTHER INFORMATION: Synthetic

<400> SEQUENCE: 29

Thr Lys Pro Arg Leu Tyr
1               5

<210> SEQ ID NO 30
<211> LENGTH: 6
<212> TYPE: PRT
<213> ORGANISM: Artificial
<220> FEATURE:
<223> OTHER INFORMATION: Synthetic

<400> SEQUENCE: 30

Thr Lys Pro Arg Leu His
1               5

<210> SEQ ID NO 31
<211> LENGTH: 6
<212> TYPE: PRT
<213> ORGANISM: Artificial
<220> FEATURE:
<223> OTHER INFORMATION: Synthetic

<400> SEQUENCE: 31

Thr Lys Pro Arg Val Tyr
1               5

<210> SEQ ID NO 32
<211> LENGTH: 6
<212> TYPE: PRT
<213> ORGANISM: Artificial
<220> FEATURE:
<223> OTHER INFORMATION: Synthetic

<400> SEQUENCE: 32

Thr Lys Pro Arg Val His
1               5

<210> SEQ ID NO 33
<211> LENGTH: 6
<212> TYPE: PRT
<213> ORGANISM: Artificial
<220> FEATURE:
<223> OTHER INFORMATION: Synthetic

<400> SEQUENCE: 33

Gly Tyr Thr Lys Pro Arg
1               5

<210> SEQ ID NO 34
<211> LENGTH: 6
<212> TYPE: PRT
<213> ORGANISM: Artificial
<220> FEATURE:
```

```
<223> OTHER INFORMATION: Synthetic

<400> SEQUENCE: 34

Gly His Thr Lys Pro Arg
1               5

<210> SEQ ID NO 35
<211> LENGTH: 6
<212> TYPE: PRT
<213> ORGANISM: Artificial
<220> FEATURE:
<223> OTHER INFORMATION: Synthetic

<400> SEQUENCE: 35

Ala Tyr Thr Lys Pro Arg
1               5

<210> SEQ ID NO 36
<211> LENGTH: 6
<212> TYPE: PRT
<213> ORGANISM: Artificial
<220> FEATURE:
<223> OTHER INFORMATION: Synthetic

<400> SEQUENCE: 36

Ala His Thr Lys Pro Arg
1               5

<210> SEQ ID NO 37
<211> LENGTH: 6
<212> TYPE: PRT
<213> ORGANISM: Artificial
<220> FEATURE:
<223> OTHER INFORMATION: Synthetic

<400> SEQUENCE: 37

Leu Tyr Thr Lys Pro Arg
1               5

<210> SEQ ID NO 38
<211> LENGTH: 6
<212> TYPE: PRT
<213> ORGANISM: Artificial
<220> FEATURE:
<223> OTHER INFORMATION: Synthetic

<400> SEQUENCE: 38

Leu His Thr Lys Pro Arg
1               5

<210> SEQ ID NO 39
<211> LENGTH: 6
<212> TYPE: PRT
<213> ORGANISM: Artificial
<220> FEATURE:
<223> OTHER INFORMATION: Synthetic

<400> SEQUENCE: 39

Val Tyr Thr Lys Pro Arg
1               5

<210> SEQ ID NO 40
<211> LENGTH: 6
<212> TYPE: PRT
<213> ORGANISM: Artificial
<220> FEATURE:
<223> OTHER INFORMATION: Synthetic
```

```
<400> SEQUENCE: 40

Val His Thr Lys Pro Arg
1               5
```

PHOSPHORYLCHOLINE CONJUGATES AND USES THEREOF

CROSS-REFERENCE TO RELATED APPLICATIONS

This application is a continuation of U.S. application Ser. No. 14/956,167 filed on Dec. 1, 2015, which claims benefit to U.S. application Ser. No. 14/766,108 filed on Aug. 5, 2015, which is a 35 U.S.C. § 371 National Phase Entry Application from International Application No. PCT/IL2014/050124 filed on Feb. 5, 2014, and designating the United States, which claims the benefit of U.S. Provisional Application No. 61/760,668 filed on Feb. 5, 2013. The contents of all of these applications are hereby expressly incorporated by reference as fully set forth herein, in their entirety.

FIELD OF THE INVENTION

The present invention relates to phosphorylcholine based agents and pharmaceutical compositions comprising same for the prevention and treatment of autoimmune diseases, particularly autoimmune diseases associated with pathological inflammation.

BACKGROUND OF THE INVENTION

A strong correlation between improved sanitation and significant increase in the prevalence of autoimmune and autoinflammatory syndromes has been demonstrated in western countries. Moreover, a correlation between the presence of parasitic worms (helminths) in certain geographic areas and protection from atopic, autoimmune, and autoinflammatory diseases was reported. These studies led to the "hygiene hypothesis", postulating that the recent increase in autoimmune disease incidences in the west reflects an absence of appropriate priming of the immune response by infectious agents, including parasitic worms, during childhood.

During the last decades many studies reported that infection with parasitic helminthes, or systemic treatment with helminths extracts, can reduce inflammation associated with autoimmune diseases, such as multiple sclerosis (MS), rheumatoid arthritis (RA), type I diabetes mellitus (T1DM), and inflammatory bowel disease (IBD).

Although such studies were successful, using potential pathogens as therapeutic agents has raised ethic and safety issues. Therefore, considerable effort has been spent in identifying and characterizing the parasite-derived molecules responsible for their immunomodulation.

The currently most-well defined nematode-derived immunomodulatory molecule is ES-62. ES-62 is a tetrameric glycoprotein (62 kDa subunits) that has phosphorylcholine (PC)-moieties attached via an N-type glycan.

It has been proposed that the immunomodulatory activity of ES-62 is attributed to the presence of the PC moieties. Further support for the PC immunomodulatory activity was found in other parasitic nematodes like *Ascaris suum* that express only the PC-immunomodulatory moiety.

U.S. Pat. No. 5,455,032 discloses compositions useful for inducing immunoprotection against infections by pathogenic organisms containing phosphocholine antigens, including *Streptococcus pneumoniae* and other microorganisms that have a phosphocholine antigen component on their membranes or capsids. Further disclosed are vaccines and methods for inducing immunoprotection against infection by these pathogenic organisms.

U.S. Pat. No. 7,067,480 discloses the use of a phosphorylcholine-containing glycoprotein, particularly ES-62, in the treatment or prophylaxis of autoimmune diseases associated with abnormal inflammation such as rheumatoid arthritis.

U.S. Pat. No. 8,012,483 discloses a method for identifying subjects at risk of developing ischemic cardiovascular diseases by determining the presence of antibodies, particularly IgM antibodies, toward phosphorylcholine and further discloses pharmaceutical compositions comprising a phosphorylcholine conjugate, or an antibody with specificity to a phosphorylcholine conjugate for active or passive immunogens in the treatment or prevention of atherosclerosis.

U.S. Patent Application, Publication No. 2010/0303721, discloses a method of treating an excessive immune response including an aberrant/enhanced Th1 response with a helminthic parasite preparation. The autoimmune diseases includes Crohn's disease and ulcerative colitis, rheumatoid arthritis, type 1 diabetes mellitus, lupus erythematosus, sarcoidosis, multiple sclerosis, autoimmune thyroiditis, allergic rhinitis, colon polyps/colon cancer and asthma.

There remains a need to develop small molecules as safe and stable immunomodulators, with minimal adverse side effects, for treating autoimmune diseases, particularly disease associated with abnormal inflammation.

SUMMARY OF THE INVENTION

The present invention provides pharmaceutical compositions comprising phosphorylcholine (PC) conjugates and uses thereof for treatment and/or prevention of autoimmune diseases and disorders, such as, rheumatoid arthritis, lupus, multiple sclerosis, and inflammatory bowel disease.

The present invention is based in part on the unexpected discovery that phosphorylcholine-conjugates comprising tuftsin derivatives (TD-PC), such as Thr-Lys-Pro-Arg-Gly-Tyr-PC (namely, SEQ ID NO: 25 conjugated to PC), exhibited an inhibitory and immunomodulatory effect on the development and progression of colitis, rheumatoid arthritis and systemic lupus erythematosus (SLE) in vivo.

The present invention provides, in one aspect, a phosphorylcholine-conjugate comprising at least one phosphorylcholine derivative attached to at least one tuftsin derivative, the tuftsin derivative comprising a tuftsin attached to a plurality of amino acids, the plurality comprising a first amino acid attached to a second amino acid, wherein the first amino acid is selected from the group consisting of glycine, alanine, leucine, valine, arginine, histidine, lysine, serine, threonine, asparagine, glutamine, isoleucine, methionine, and non-natural, non-charged and non-polar amino acids, and wherein the second amino acid is selected from the group consisting of tyrosine and histidine.

In certain embodiments, the first amino acid is selected from the group consisting of glycine, alanine, leucine, valine, β-alanine-6-aminohexanoic acid and 5-aminopentanoic acid. In certain embodiments, the first amino acid is selected from the group consisting of glycine, alanine, leucine and valine. Each possibility represents a separate embodiment of the invention. In certain embodiments, the first amino acid is glycine. Each possibility represents a separate embodiment of the invention.

In certain embodiments, the second amino acid is tyrosine. In certain embodiments, the second amino acid is tyrosine, and the PC derivative is p-aminophenylphosphorylcholine. In certain embodiments, the PC derivative is 4-aminophenylphosphorylcholine.

In certain embodiments, the second amino acid is tyrosine, the PC derivative is p-aminophenylphosphorylcholine, wherein said tyrosine is bound to the p-aminophenylphosphorylcholine In certain embodiments, the second amino acid is histidine.

In certain embodiments, the phosphorylcholine-conjugate described above comprises one phosphorylcholine derivative attached to one tuftsin derivative. In certain embodiments, the phosphorylcholine-conjugate described above comprises a plurality of phosphorylcholine derivatives attached to a plurality of tuftsin derivatives. In certain embodiments, the phosphorylcholine-conjugate described above comprises a plurality of tuftsin derivatives attached to one phosphorylcholine derivative. In certain embodiments, the phosphorylcholine-conjugate described above comprises a plurality of phosphorylcholine derivatives attached to one tuftsin derivative.

In certain embodiments, the phosphorylcholine-conjugate described above comprises at least one phosphorylcholine derivative and the at least one tuftsin derivative are separated by a spacer.

In certain embodiments, the tuftsin derivative comprises an amino-acid sequence selected from the group consisting of SEQ ID NO: 23 to SEQ ID NO: 40. Each possibility represents a separate embodiment of the invention.

In certain embodiments, the tuftsin derivative comprises the amino-acid sequence set forth in any one of SEQ ID NOs: 23 and 24.

In certain embodiments, the tuftsin derivative comprises the amino-acid sequence set forth in SEQ ID NO: 25.

In certain embodiments, the tuftsin derivative is consisting of the amino-acid sequence set forth in SEQ ID NO: 25.

The present invention further provides, in another aspect, a pharmaceutical composition comprising any one of the phosphorylcholine-conjugates described above, and further comprises a pharmaceutically acceptable carrier, diluent or excipient.

The present invention further provides, in another aspect, a method for treating an autoimmune disease in a subject in need thereof comprising administering to the subject the pharmaceutical composition described above.

In certain embodiments, treating comprises at least one of preventing the onset of said autoimmune disease, attenuating the progress of said autoimmune disease and inhibiting the progression of said autoimmune disease. In certain embodiments, treating comprises at least one of attenuating the progress of said autoimmune disease and inhibiting the progression of said autoimmune disease. Each possibility represents a separate embodiment of the invention.

In certain embodiments, the subject is at high risk of developing said autoimmune disease.

In certain embodiments, the autoimmune disease is associated with abnormal inflammation. In certain embodiments, the autoimmune disease is selected from the group consisting of rheumatoid arthritis, lupus, colitis, multiple sclerosis, pemphigus vulgaris, antiphospholipid syndrome, psoriasis, autoimmune hepatitis, sarcoidosis, inflammatory bowel disease, crohn's disease and chronic obstructive pulmonary disease. In certain embodiments, the autoimmune disease is selected from the group consisting of rheumatoid arthritis, lupus and colitis. In certain embodiments, the autoimmune disease is lupus. In certain embodiments, the autoimmune disease is colitis. In certain embodiments, the autoimmune disease is rheumatoid arthritis. Each possibility represents a separate embodiment of the invention.

In certain embodiments, the pharmaceutical composition is administered in a route of administration selected from the group consisting of oral, intravenous, intramuscular, sublingual, intramucosal, intraperitoneal, nasal, subcutaneous, topical, and intradermal or transdermal. In certain embodiments, the pharmaceutical composition is orally administered. Each possibility represents a separate embodiment of the invention.

In certain embodiments, the subject is a mammal. In certain embodiments, the subject is human.

The present invention further provides, in another aspect, a kit comprising a container comprising any one of the phosphorylcholine-conjugates described above.

In certain embodiments, the kit described above further comprises a second container comprising a pharmaceutically acceptable carrier, diluent or excipient. In certain embodiments, the kit described above further comprises instructions for preparing a pharmaceutical composition from the contents of said first and said second containers.

DETAILED DESCRIPTION OF THE INVENTION

Figure 1:
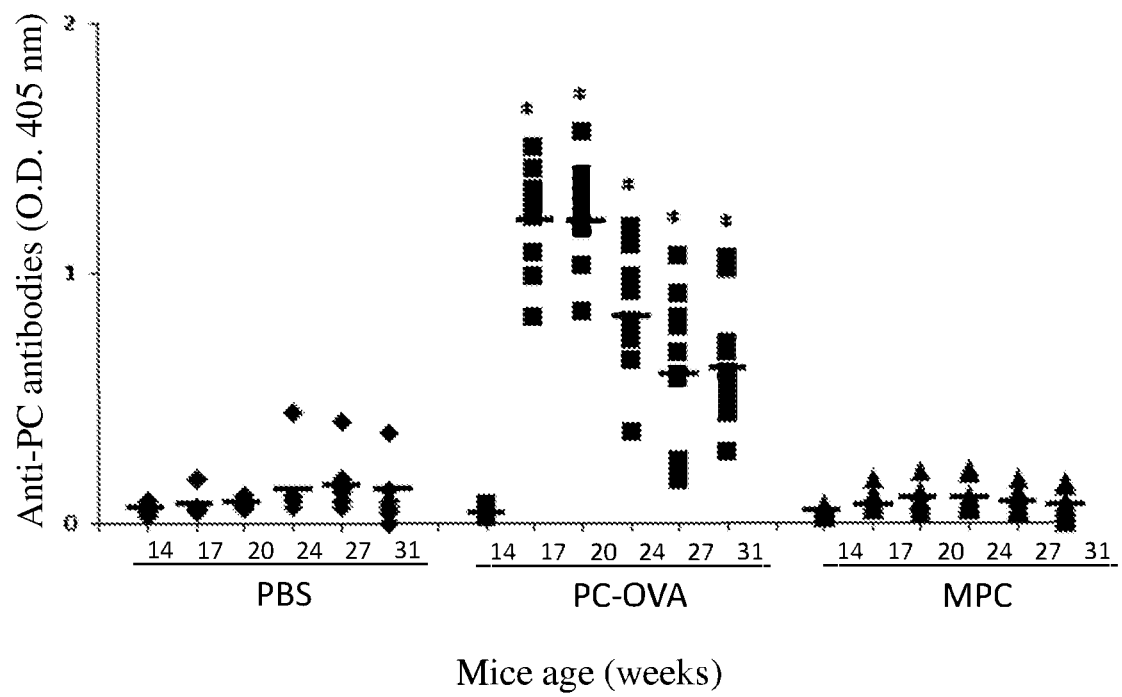
FIG. 1 shows the level of anti-PC antibodies (in units of Optical Density, O.D., at 405 nm) in the sera of NZBxNZW/F1 mice ("lupus mice") treated with PC-OVA (square; *=$p<0.001$), MPC (triangle; $p>0.05$) or PBS (control; diamond).

The present invention provides pharmaceutical compositions comprising at least one phosphorylcholine (PC) conjugated to at least one tuftsin derivative. According to some embodiments, the pharmaceutical compositions of the invention exhibit an immunomodulatory activity. According to some embodiments, the pharmaceutical compositions are for treating, ameliorating the progress of, and preventing onset of, autoimmune diseases.

The present invention provides, in one aspect, a phosphorylcholine-conjugate comprising at least one phosphorylcholine derivative attached to at least one tuftsin derivative, the tuftsin derivative comprising a tuftsin (threonine-lysine-proline-arginine; TKPR; SEQ ID NO: 17) attached to a plurality of amino acids, the plurality comprising a first amino acid attached to a second amino acid, wherein the first amino acid is selected from the group consisting of glycine, alanine, leucine, valine, arginine, histidine, lysine, serine, threonine, asparagine, glutamine, isoleucine, methionine, and non-natural, non-charged and non-polar amino acids, and wherein the second amino acid is selected from the group consisting of tyrosine and histidine.

The term "phosphorylcholine (PC) conjugate" as used herein, refers to a phosphorylcholine moiety or a derivative thereof linked to a tuftsin-derivative (TD), optionally via a spacer.

The term "spacer", as used herein, refers to a connecting or otherwise bridging element between the tuftsin derivative and the PC derivative, typically linked by chemical methods or biological means thereto. Non-limiting examples of spacers include: amino acids, peptides, polypeptides, proteins, hydrocarbons and polymers among others. Each possibility is a separate embodiment of the invention.

As used herein, the term "derivative of phosphorylcholine" includes, but is not limited to, the following: 4-aminophenyl-phosphocholine, 4-diazonio-phenyl-phosphorylcholine, 4-nitro-phenyl-phosphocholine and 12-(3-iodophenyl) dodecyl-phosphocholine among others. Each possibility is a separate embodiment of the invention.

As used herein, the term "tuftsin" refers to a tetrapeptide (threonine-lysine-proline-arginine, TKPR; SEQ ID NO: 17). Tuftsin may be synthesized chemically or isolated from the spleen by enzymatic cleavage of the Fc domain of IgG heavy chain. Tuftsin is known for its phagocytosis-stimulating activity and augmentation of antigen presenting capacity of macrophages in-vitro and in-vivo. According to some embodiments, tuftsin may be considered as an immunomodulatory molecule.

The terms "tuftsin derivative", "TD" and "tuftsin-derived carrier moiety" are interchangeable and refer to tuftsin (THR-LYS-PRO-ARG; SEQ ID NO: 17) attached to at least two additional amino acids which are independently selected. These terms thus include, but are not limited to, the SEQ ID NOs presented in Table 1. Non-natural amino acids, preferably non-charged and non-polar non-natural amino acids such as 13-alanine-6- aminohexanoic acid and 5-aminopentanoic acid, may also be comprised in the tuftsin derivative.

The term "moiety" as used herein refers to a part of a molecule, which lacks one or more atom(s) compared to the corresponding molecule. The term "moiety", as used herein, further relates to a part of a molecule that may include either whole functional groups or parts of functional groups as substructures. The term "moiety" further means part of a molecule that exhibits a particular set of chemical and/or pharmacologic characteristics which are similar to the corresponding molecule.

The term "attached to" as used herein refers to a covalent bond between at least two molecules or moieties. According to the principles of the present invention, the natural and non-natural amino-acids comprised in the tuftsin derivative are adjacent and attached to one another, while the at least one phosphorylcholine derivative is attached to the at least one tuftsin derivative either directly or indirectly via a spacer.

In certain embodiments, the first amino acid is selected from the group consisting of glycine, alanine, leucine, valine, β-alanine-6-aminohexanoic acid and 5-aminopentanoic acid. In certain embodiments, the first amino acid is selected from the group consisting of glycine, alanine, leucine and valine. Each possibility represents a separate embodiment of the invention.

In certain embodiments, the first amino acid is glycine.

In certain embodiments, the second amino acid is tyrosine. In certain embodiments, the PC derivative is p-aminophenylphosphorylcholine. In certain embodiments, the second amino acid is tyrosine and the PC derivative is p-aminophenylphosphorylcholine wherein the tyrosine is conjugated to said p-aminophenylphosphorylcholine. In certain embodiments, the second amino acid is histidine.

In certain embodiments, the phosphorylcholine-conjugate described above comprises one phosphorylcholine derivative attached to one tuftsin derivative. In certain embodiments, the phosphorylcholine-conjugate described above comprises a plurality of phosphorylcholine derivatives attached to a plurality of tuftsin derivatives. In certain embodiments, the phosphorylcholine-conjugate described above comprises a plurality of tuftsin derivatives attached to one phosphorylcholine derivative. In certain embodiments, the phosphorylcholine-conjugate described above comprises a plurality of phosphorylcholine derivatives attached to one tuftsin derivative.

In certain embodiments, the phosphorylcholine-conjugate described above comprises at least one phosphorylcholine derivative and the at least one tuftsin derivative are separated by a spacer.

TABLE 1

Amino-acid sequences of certain tuftsin derivatives

| Amino-acid sequences | SEQ ID NO: |
|---|---|
| Threonine-Lysine-Proline-Arginine-Xaa-Xaa | 23 |
| Xaa-Xaa-Threonine-Lysine-Proline-Arginine | 24 |
| Threonine-Lysine-Proline-Arginine-Glycine-Tyrosine | 25 |
| Threonine-Lysine-Proline-Arginine-Glycine-Histidine | 26 |
| Threonine-Lysine-Proline-Arginine-Alanine-Tyrosine | 27 |
| Threonine-Lysine-Proline-Arginine-Alanine-Histidine | 28 |
| Threonine-Lysine-Proline-Arginine-Leucine-Tyrosine | 29 |
| Threonine-Lysine-Proline-Arginine-Leucine-Histidine | 30 |
| Threonine-Lysine-Proline-Arginine-Valine-Tyrosine | 31 |
| Threonine-Lysine-Proline-Arginine-Valine-Histidine | 32 |
| Glycine-Tyrosine-Threonine-Lysine-Proline-Arginine | 33 |
| Glycine-Histidine-Threonine-Lysine-Proline-Arginine | 34 |
| Alanine-Tyrosine-Threonine-Lysine-Proline-Arginine | 35 |
| Alanine-Histidine-Threonine-Lysine-Proline-Arginine | 36 |
| Leucine-Tyrosine -Threonine-Lysine-Proline-Arginine | 37 |
| Leucine-Histidine-Threonine-Lysine-Proline-Arginine | 38 |
| Valine-Tyrosine-Threonine-Lysine-Proline-Arginine | 39 |
| Valine-Histidine-Threonine-Lysine-Proline-Arginine | 40 |

In certain embodiments, the tuftsin derivative comprises or consists of an amino-acid sequence selected from the group consisting of SEQ ID NO: 23 and SEQ ID NO: 24. In certain embodiments, the tuftsin derivative comprises or consists of an amino-acid sequence selected from the group consisting of SEQ ID NO: 25 to SEQ ID NO: 40. In certain embodiments, the tuftsin derivative comprises or consists of an amino-acid sequence selected from the group consisting of SEQ ID NO: 25 to SEQ ID NO: 32. In certain embodiments, the tuftsin derivative comprises or consists of an amino-acid sequence selected from the group consisting of SEQ ID NO: 33 to SEQ ID NO: 40. In certain embodiments, the tuftsin derivative comprises or consists of an amino-acid sequence selected from the group consisting of SEQ ID NO: 25 to SEQ ID NO: 26. In certain embodiments, the tuftsin derivative comprises or consists of an amino-acid sequence selected from the group consisting of SEQ ID NO: 25, SEQ ID NO: 27, SEQ ID NO: 29 and SEQ ID NO: 31. In certain embodiments, the tuftsin derivative comprises or consists of an amino-acid sequence selected from SEQ ID NO: 25 and SEQ ID NO: 33. In certain embodiments, the tuftsin derivative comprises or consists of the amino-acid sequence of SEQ ID NO: 25. Each possibility represents a separate embodiment of the invention.

The present invention further provides, in another aspect, a pharmaceutical composition comprising any one of the phosphorylcholine-conjugates described above, and further comprises a pharmaceutically acceptable carrier, diluent or excipient.

As used herein, the term "pharmaceutical composition" refers to any composition comprising at least one pharmaceutically active ingredient and at least one other ingredient, as well as any product which results, directly or indirectly, from combination, complexation, or aggregation of any two or more of the ingredients, from dissociation of one or more of the ingredients, or from other types of reactions or interactions of one or more of the ingredients. Accordingly, the term "pharmaceutical composition" as used herein may encompass, inter alia, any composition made by admixing a pharmaceutically active ingredient and one or more pharmaceutically acceptable carriers.

The present invention further provides, in another aspect, a method for treating an autoimmune disease in a subject in need thereof comprising administering to the subject the pharmaceutical composition described above.

As used herein, the terms "treating" or "treatment" are interchangeable and refer to any one or more of preventing the onset of an autoimmune disease, attenuating the progress of said autoimmune disease and inhibiting the progression of an autoimmune disease, among others.

In certain embodiments, treating comprises at least one of preventing the onset of said autoimmune disease, attenuating the progress of said autoimmune disease and inhibiting the progression of said autoimmune disease. In certain embodiments, treating comprises at least one of attenuating the progress of said autoimmune disease and inhibiting the progression of said autoimmune disease. Each possibility represents a separate embodiment of the invention.

In certain embodiments, the subject is at high risk of developing said autoimmune disease. As used herein, the term "high risk subject" is used to mean a human who is considered to be at a higher risk of developing an autoimmune disease compared to the general population.

In certain embodiments, the autoimmune disease is associated with abnormal inflammation.

In certain embodiments, the autoimmune disease is selected from Acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, castleman disease, celiac disease, chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, Crest disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis (temporal arteritis), giant cell myocarditis, Glomerulonephritis, Goodpasture's syndrome, granulomatosis with polyangiitis (GPA) (formerly called Wegener's Granulomatosis), Graves' disease, Guillain-Barre syndrome, Hashimoto's encephalitis, Hashimoto's thyroi ditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), Lupus (SLE), lyme disease, chronic, Meniere's disease, microscopic polyangiitis, mixed connective tissue disease (MCTD), Mooren's ulcer, Mucha-Habermann disease, multiple sclerosis, Myasthenia gravis, Myositis, NarcOlepsy, Neuromyelitis optica (Devic's), neutropenia, Ocular cicatricial pemphigoid, optic neuritis, palindromic rheumatism, PANDAS (Pediatric Autoimmune Neuropsychiatric Disorders Associated with Streptococcus), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, Rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, ulcerative colitis, undifferentiated connective tissue disease (UCTD), Uveitis, Vasculitis, vesiculobullous dermatosis, vitiligo and Wegener's granulomatosis (now termed granulomatosis with polyangiitis (GPA).

In certain embodiments, the autoimmune disease is selected from the group consisting of rheumatoid arthritis, lupus, colitis, multiple sclerosis, pemphigus vulgaris, antiphospholipid syndrome, psoriasis, autoimmune hepatitis, sarcoidosis, inflammatory bowel disease, crohn's disease and chronic obstructive pulmonary disease. Each possibility represents a separate embodiment of the invention.

In certain embodiments, the autoimmune disease is selected from the group consisting of rheumatoid arthritis, lupus and colitis. In certain embodiments, the autoimmune disease is lupus. In certain embodiments, the autoimmune disease is colitis. In certain embodiments, the autoimmune disease is rheumatoid arthritis. Each possibility represents a separate embodiment of the invention.

In certain embodiments, the pharmaceutical composition is administered in a route of administration selected from the group consisting of oral, intravenous, intramuscular, sublingual, intramucosal, intraperitoneal, nasal, subcutaneous, topical, intradermal and transdermal. In certain embodiments, the pharmaceutical composition is orally administered. Each possibility represents a separate embodiment of the invention.

In certain embodiments, the subject is a mammal. In certain embodiments, the subject is human.

The present invention further provides, in another aspect, a kit comprising a container comprising any one of the phosphorylcholine-conjugates described above.

The term "kit" is typically meant a collection or array of certain equipment and chemicals (e.g. conjugates, buffers, etc.).

In certain embodiments, the kit described above further comprises a second container comprising a pharmaceutically acceptable carrier, diluent or excipient. In certain embodiments, the kit described above further comprises instructions for preparing a pharmaceutical composition from the contents of said first and said second containers.

According to some embodiments, the TD-PC-conjugates of the present invention are produced synthetically to ensure the stability and reproducibility of these compounds, while maintaining or even enhancing their activity. According to some embodiments, TD-PC-conjugates are useful as stimulators of a subject immune system towards the Th2 phenotype.

As used herein, the terms "immunomodulation", "immunomodulation activity", "immunomodulatory activity" or "modulating the immune response" with reference to the TD-PC-conjugates of the present invention refer to the ability of the conjugates to elicit at least one of: reducing the ability of lymphocytes (both B- and T-) to proliferate in response to antigen; inducing generation of T and/or B regulatory (suppressor) cells; and affecting macrophages and dendritic cell functions. Affecting macrophages and dendritic cell functions includes but is not limited to, stimulating clearance of apoptotic cells and inducing tolerogenic dendritic cells; inhibiting the ability of macrophages to produce pro-inflammatory cytokines such as IL-12, TNF-α and IL-6; modulating dendritic cell maturation to preferentially elicit Th2-like responses; and inducing spleen cells to produce the anti-inflammatory cytokine, IL-10 and to bias antibody responses in a Th2/anti-inflammatory direction. The immunomodulatory activity of the TD-PC-conjugates may be also referred to herein as "anti-inflammatory" activity.

The tuftsin-derived (TD) carrier moiety may be immunogenic or non-immunogenic.

As used herein, the term "immunogenic carrier" refers to a variety of molecules or substances that are capable of inducing an immune response against the PC molecule.

In the Gram-positive bacterium *Streptococcus pneumonia* PC is attached directly to sugar residues, generally considered to be N-acetylgalactosamine. PC has been detected also in a wide range of Gram-positive bacteria including *Clostridium, Lactococcus, Bacillus* and the Gram-negative bacterium *Haemophilus influenzae*. Eukaryotic organisms in which PC has been detected include many important disease-causing agents such as the protozoa *Leishmania major* and *Trypanosoma cruzi*; a wide range of fungi; the trematode *Schistosoma mansoni*; the tapeworm *Diphyllobothrium latum*; several gastrointestinal nematodes and all species of filarial nematode. In human, PC appears on the inner leaflet of a cell membrane and is exposed to the immune system by apoptotic cells.

The term "non-immunogenic carrier" as used herein refers to a variety of molecules or substances that do not elicit an immune response.

According to some embodiments, the TD-PC-conjugate comprises PC and a tuftsin derivative, linked to one another.

As used herein, the term "linked" refers to attached, connected, bound to, in association with and coupled to, among others.

According to some embodiments, the PC and the tuftsin derivative are linked through a covalent bond.

According to additional embodiments, the synthetic TD-PC-conjugates of the present invention may be synthesized as described in the Example section hereinbelow.

According to other embodiments, the pharmaceutical composition is in the form of solution, suspension, tablets, chewable tablets, capsules, syrups, intranasal sprays, suppositories, transdermal patches, among other types of pharmaceutical compositions. Each possibility is a separate embodiment of the invention.

According to other embodiments, the pharmaceutical composition is a long acting, controlled release, extended release or slow release formulation. Each possibility is a separate embodiment of the invention.

The pharmaceutical compositions of the invention are suitable for use in a variety of drug delivery systems as detailed hereinbelow. Pharmaceutically acceptable carriers suitable for use in the present invention may be found in Remington's Pharmaceutical Sciences, Mack Publishing Company, Philadelphia, Pa., 17th ed. (1985).

According to some embodiments, the method of the invention comprises the steps of (i) determining the risk of a subject for an autoimmune disease; (ii) selecting a subject having a risk for said disease; and (iii) treating said subject having the risk with the PC-conjugate of the invention.

According to some embodiments, the method of the invention comprises the steps of (i) identifying a subject in a risk for an autoimmune disease; and (iii) treating said subject with the PC-conjugate of the invention.

Lupus, or lupus erythematosus, as used herein, refers to a category for a collection of systemic autoimmune diseases. Symptoms of these diseases may affect many different body systems, including joints, skin, kidneys, blood cells, heart, and lungs. Four main types of lupus are known to date: systemic lupus erythematosus, discoid lupus erythematosus, drug-induced lupus erythematosus, and neonatal lupus erythematosus. Of these, systemic lupus erythematosus is the most common and serious form of lupus. The abnormal immune response allows sustained production of pathogenic autoantibodies and immune complexes that cause damage to the various tissues and systems. The abnormal immune response probably depends upon the interaction of multiple hereditary and environmental factors.

The terms "rheumatoid arthritis" and "RA", as used herein are interchangeable and refer to a chronic disease featuring persistent inflammatory synovitis, typically involving peripheral joints in a symmetric distribution. This inflammation may lead to bone erosions, cartilage damage and joint destruction. It is an affliction of about 1% of the population. The prevalence increases with age, and women are affected more frequently than men. The propagation of RA is an immunologically mediated event driven by $CD4^+$ Th1 cells.

The terms "Multiple sclerosis" and "MS", as used herein are interchangeable and typically refer to a chronic relapsing, multifocal inflammatory disorder of the central nervous system that leads to focal demyelination and scarring of the brain. It is a frequent disease affecting about 350,000 Americans, manifesting during early to middle adulthood. MS is an autoimmune disease mediated at least in part by Th1 cells. The lesions of MS resemble those induced by delayed hypersensitivity responses that contain activated T cells and macrophages. Experimental autoimmune encephalomyelitis, also named Experimental Allergic Encephalomyelitis (EAE) is an animal model of brain inflammation. It is an inflammatory demyelinating disease of the central nervous system (CNS). It is mostly used with rodents and is widely studied as an animal model of the human CNS demyelinating diseases, including the diseases multiple sclerosis and acute disseminated encephalomyelitis (ADEM). EAE is also the prototype for T-cell-mediated autoimmune disease in general.

The term "colitis" as used herein refers to any one or more of the following diseases and disorders: inflammatory bowel disease (IBD), Crohn's disease, ulcerative colitis, collagenous colitis, lymphocytic colitis, ischemic colitis, diversion colitis, Behcet's disease and indeterminate colitis, among others.

While the cause of IBD remains undetermined, it is presumed to result from dysregulation of the intestinal mucosal immune system. Inflammatory cells in the mucosa normally have a protective effect against luminal contents. This highly effective chronic inflammation is tightly controlled to limit tissue injury. IBD may result from inappropriately vigorous immune responses to luminal factors. Crohn's disease (CD) appears to be an overly vigorous Th-type inflammation that produces $IFN\gamma$ and $TNF\alpha$. The incidence of Crohn's disease in industrialized societies has increased from the 1950s until the mid-1980s, and now is about 1 to 8 cases per 100,000 persons per year. This suggests that unknown changes in our environment have affected the frequency of Crohn's disease. The nature of ulcerative colitis (UC) is less well defined.

There are several animal models of chronic intestinal inflammation. In fact, mice with genetically engineered gene deletions may develop chronic bowel inflammation similar to IBD. These include mutant mice bearing targeted deletions for IL-2, 1L-10, and MHC class II or TCR genes among others. It was shown in some animal models that a dysregulated immune system itself can mediate intestinal injury. The mucosal inflammation in several animal models generates large amounts of $IFN\gamma$ and $TNF\alpha$, suggesting that excess production of Th1-type cytokines is one common mechanism underlying the pathogenesis of disease. Also, blocking Th1 circuitry prevents the inflammation. CD is a Th1 response. Thus, these models may have direct implications in the immunopathology of this human disease process.

According to some embodiments, the method of the invention is for treating colitis wherein the carrier of the PC-conjugate is a tuftsin derivative.

According to some embodiments, the method of the invention is for treating colitis.

According to some embodiments, the disease or disorder is an autoimmune skin disorder. There are many different types of skin-related autoimmune disorders, including, for example scleroderma, psoriasis, dermatomyositis, epidermolysis bullosa and bullous pemphigoid. Pemphigus vulgaris is a chronic blistering skin disease with skin lesions that are rarely pruritic, but which are often painful. The disease is caused by antibodies directed against both desmoglein 1 and desmoglein 3 resulting in the loss of cohesion between keratinocytes in the epidermis. It is characterized by extensive flaccid blisters and mucocutaneous erosions. Psoriasis occurs when the immune system mistakes the skin cells as a pathogen, and sends out faulty signals that speed up the growth cycle of skin cells. The disorder is a chronic recurring condition that varies in severity from minor localized patches to complete body coverage. Fingernails and toenails are frequently affected (psoriatic nail dystrophy) and may be seen as an isolated symptom. Psoriasis may also cause inflammation of the joints, which is known as psoriatic arthritis.

Thus, the invention provides compositions for parenteral administration that comprise a solution of the agents described above dissolved or suspended in an acceptable carrier, such as an aqueous carrier. A variety of pharmaceutically acceptable aqueous carriers may be used, e.g., water, buffered water, 0.4% saline, 0.3% glycine hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain as pharmaceutically acceptable carriers substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. Each possibility is a separate embodiment of the invention.

The pharmaceutical compositions of the invention may be in the solid state. For solid compositions, conventional nontoxic pharmaceutically acceptable carriers may be used which include, for example, pharmaceutical grades of mannitol, lactose, starch, magnesium stearate, sodium saccharin, talcum, cellulose, glucose, sucrose, magnesium carbonate, and the like. Pharmaceutical formulations suitable for oral administration wherein the excipient is solid are, for example, presented as unit dose formulations such as boluses, capsules or tablets each containing a predetermined amount of the PC-conjugate of the invention as the active compound. A tablet may be made by compression or molding, optionally with one or more accessory ingredients. Compressed tablets may be prepared by compressing in a suitable machine the active compound in a free-flowing form such as a powder or granules optionally mixed with a binder, lubricant, inert diluents, lubricating agent, surface-active agent or dispersing agent. Molded tablets may be made by molding the active compound with inert liquid diluents. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may, for example, be suspended in water before administration, or sprinkled on food. The granules may be packaged, e.g., in a sachet.

For aerosol administration, the pharmaceutical compositions of the invention are, for example, supplied in finely divided form along with a surfactant and optionally a propellant as pharmaceutically acceptable carriers. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Each possibility is a separate embodiment of the invention. Mixed esters, such as mixed or natural glycerides, may be employed. A carrier may also be included, as desired, as with, e.g., lecithin for intranasal delivery.

The pharmaceutical compositions of the invention may be in the form liposome. Liposomes provide another delivery system for the delivery and presentation of the immunomodulatory molecules of the invention. Liposomes are bilayer vesicles composed of phospholipids and other sterols surrounding a typically aqueous center where the PC-conjugate or other products may be encapsulated. The liposome structure is highly versatile with many types range in nanometer to micrometer sizes, from about 25 nm to about 500 µm. Liposomes have been found to be effective in delivering therapeutic agents to dermal and mucosal surfaces. Liposomes may be further modified for targeted delivery by, for example, incorporating specific antibodies into the surface membrane. The average survival time or half-life of the intact liposome structure may be extended with the inclusion of certain polymers, such as polyethylene glycol, allowing for prolonged release in vivo. Liposomes may be unilamellar or multilamellar.

The pharmaceutical compositions of the invention may be in the form of microparticles and nanoparticles. Microparticles and nanoparticles employ small biodegradable spheres which act as depots for drug delivery. The major advantage that polymer microspheres possess over other depot-effecting adjuvants is that they are extremely safe and have been approved by the Food and Drug Administration in the US for use in human medicine as suitable sutures and for use as a biodegradable drug delivery. The rates of copolymer hydrolysis are very well characterized, which in turn allows for the manufacture of microparticles with sustained release of the immunomodulators over prolonged periods of time.

The pharmaceutical compositions of the invention may be parenteral administered as microparticles. Microparticles elicit long-lasting immunity, especially if they incorporate prolonged release characteristics. The rate of release may be modulated by the mixture of polymers and their relative molecular weights, which will hydrolyze over varying periods of time. Without wishing to be bound to theory, the formulation of different sized particles (1 µm to 200 µm) may also contribute to long-lasting immunological responses since large particles must be broken down into smaller particles before being available for macrophage uptake. In this manner a single- injection vaccine could be developed by integrating various particle sizes, thereby prolonging TD-PC-conjugate presentation.

The terms "vaccine composition" and "vaccine" as used herein are interchangeable and refers to a product, the administration of which is intended to elicit an immune response that is capable of preventing and/or lessening the severity of one or more autoimmune diseases or disorders and inflammation among other diseases and disorders.

The invention also provides a kit for the treatment of an autoimmune disease comprising one or more containers filled with the pharmaceutical composition described above. Optionally associated with such container(s) may be a notice in the form described by a governmental agency regulating the manufacture, use or sale of pharmaceuticals or biological products, which notice reflects approval by the agency of manufacture, use or sale for human administration.

According to some embodiments, the present invention provides a kit for the treatment of an autoimmune disease or disorder, the kit comprising a first container comprising a phosphorylcholine-conjugate as described above; a second container comprising a pharmaceutically acceptable carriers, diluents or excipients; and, optionally, a third container comprising an adjuvant.

The TD-PC-conjugates of the invention are useful in vaccines and in immunization protocols for prevention, treatment and progress inhibition of autoimmune diseases, particularly inflammatory diseases.

According to some embodiments, the TD-PC-conjugates of the present invention, when administered to a mammal, elicit the mammal's immunomodulation activity. A variety of models known to those skilled in the art may be used to establish the immunomodulation ability of the conjugates of the invention. Cell cultures may be used to test the effect of the PC-conjugates on cell proliferation, cytokine profile, development of tolerogenic dendritic cells and development of T regulatory cell. For example, commercial kits for following pro- and anti-inflammatory cytokine, including, but not limited to IL-1, IL-2, IFNγ, IL-4, IL-10, IL-15, IL-17 and TNFα may be used. Animal models, as are known to a person skilled in the art and as exemplified herein below, may be used to test the activity of the PC-conjugates of the invention in treating, preventing or reducing the progression of autoimmune diseases.

According to some embodiments, the immunomodulation capability of the TD-PC-conjugates of the present invention are exemplified hereinbelow in animal models of autoimmune diseases, including collagen induced arthritis (CIA), colitis and systemic lupus erythematosus (SLE).

The examples hereinbelow are presented in order to more fully illustrate some embodiments of the invention. They should, in no way be construed, however, as limiting the broad scope of the invention. One skilled in the art may readily devise many variations and modifications of the principles disclosed herein without departing from the scope of the invention.

EXAMPLES

Example 1

The Effect of PC-conjugates on the Development of Systemic Lupus Erythematosus (SLE)

Phospholipids are non-immunogenic. Therefore, phosphorylcholine (PC) is commonly used as a conjugate to different carriers. The carriers may serve as immunomodulatory molecules. The following PC-conjugates were used in the current study: PC-Ovalbumin (PC-OVA; Biosearch Technologies, Inc.) and 2-methacryloyloxyethyl-PC (MPC). In MPC, the PC appears as a moiety on the helminthes. Specifically, MPC is PC-moiety on polymer (2-methacryloyloxyethyl) core defined as MPC. MPC was purchased from NOF Inc. The potential of PC-conjugates to immunomodulate lupus was studied in NZBxNZW/F1 mice which develop lupus on a genetic background.

Mice: female NZBxNZW/F1 mice were obtained from Harlan Olac, and supplied by Jackson Laboratory (Bar Harbor, USA) at the age of 8-10 weeks. The mice were maintained at the Sheba animal facilities, Sheba Medical Center, Israel. All animals were cared for as approved by the Ethical Review Committee of the Israeli Ministry of Health and Sciences animal guidelines.

The serological and clinical manifestation of lupus nephritis in NZBxNZW/F1 mice was assessed as previously described (Shoenfeld Y et al., Int. Immunol. 2002, 14(11): 1303-1311). Briefly, antibodies specific for PC were measured by ELISA as described hereinbelow. Antibodies specific for dsDNA were detected by ELISA as previously described by us (Shoenfeld et al., 2002, ibid). Proteinuria was measured by a standard semi-quantitative test using an Albustix kit (Bayer Diagnostic). Renal immune complex deposits (ICD) were determined as previously described (Shoenfeld et al., 2002, ibid). The intensity of the ICD was graded as follows: 0, no ICD; 1, low intensity; 2, moderate intensity; and 3, high intensity of ICD. ICD analysis was performed by two subjects unaware whether or not each mouse is a treatment mouse or a control mouse.

The results demonstrate the inhibitory effect of PC-OVA and MPC treatments on the development of lupus nephritis in the NZBxNZW/F1 lupus mice. The inhibitory effect was manifested by postponed proteinuria and decreased immune complex deposits on the glomerular basement membrane. The results are based on treatment at an early stage of the disease starting at week 8 of age. PC-OVA, MPC or PBS were given 3 times a week 3 µg/0.1ml per mouse subcutaneously, n=20 per group. The mice were bled every 2 weeks for measurement of PC and dsDNA specific antibodies. Proteinuria was assessed every 2 weeks.

Treatment with PC-OVA conjugate (FIG. 1, squares) was immunogenic and the mice developed elevated titers of anti-PC antibodies ($p<0.001$) in comparison to PBS (FIG. 1, diamonds) and MPC (FIG. 1, triangles) treated group, whereas MPC (poly PC on polymeric core) was non-immunogenic and did not cause generation of anti-PC antibodies ($p>0.05$). Data of the anti-PC antibodies are presented at sera dilution of 1:400. The results are given as O.D. at 405 nm. The presence of PC specific antibodies in the mice sera was detected by ELISA to PC-KLH (PC-Keyhole limpet hemocyanin), where binding to KLH served as a control reference. No response to KLH was observed. PC-OVA and MPC did not have any effect on anti-dsDNA antibodies generation in all time points (data not shown).

Figure 2:
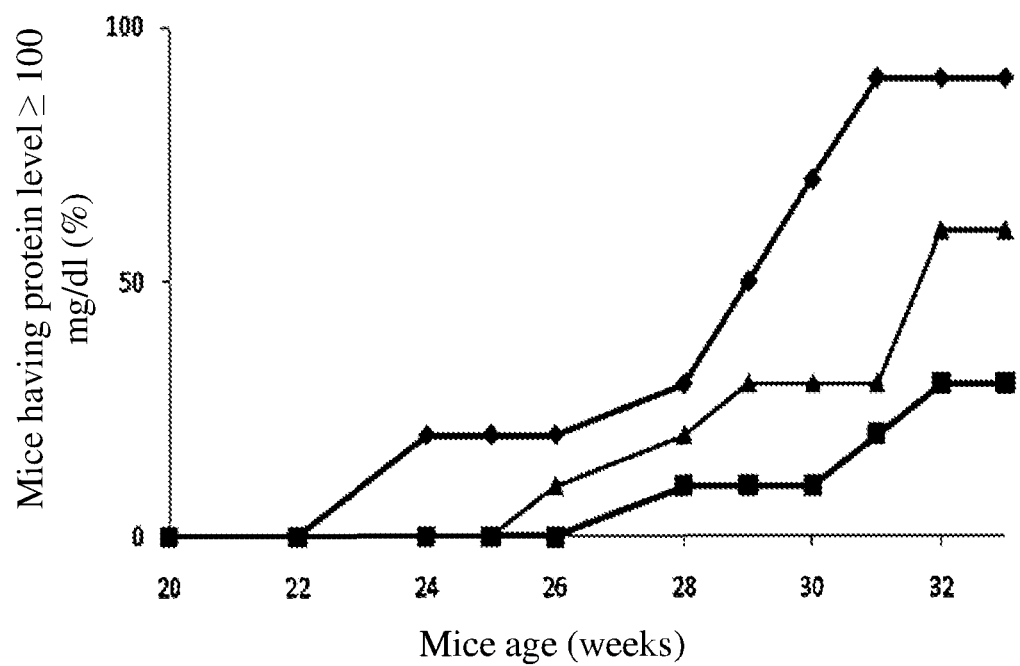
FIG. 2 shows the progression of proteinuria in lupus mice treated with PC-OVA (square), MPC (triangle) or PBS (control; diamond) as the percentage of protein levels of at least 100 mg/dl ($p<0.02$) in the urine.

No effect of PC-OVA and MPC treatment was documented in anti-dsDNA antibodies generation as illustrated in FIG. 1. Proteinuria (defined as at least 100 mg/dl protein in the urine) in lupus mice treated with PC-OVA (FIG. 2, square) or MPC (FIG. 2, triangle) was postponed significantly ($p<0.02$) in comparison to treatment with PBS (FIG. 2, diamond) at 30 to 33 weeks of age.

Figure 3A:
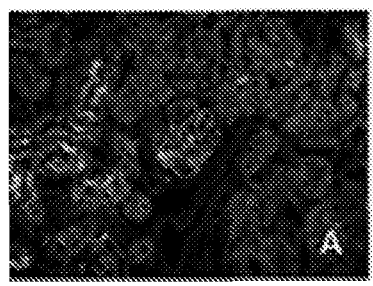
FIG. 3A shows kidney sections of lupus mice treated with PC-OVA probed with anti-mouse IgG-FITC Fc specific antibodies.
Figure 3B:
FIG. 3B shows kidney sections of lupus mice treated with PC-OVA probed with anti-mouse IgG-FITC Fc specific antibodies stained with Periodic acid-Schiff (PAS).
Figure 4A:
FIG. 4A shows kidney sections of lupus mice treated with MPC probed with anti-mouse IgG-FITC Fc specific antibodies.
Figure 4B:
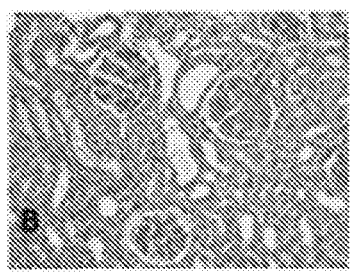
FIG. 4B show kidney sections of lupus mice treated with MPC probed with anti-mouse IgG-FITC Fc specific antibodies stained with Periodic acid-Schiff (PAS).
Figure 5A:
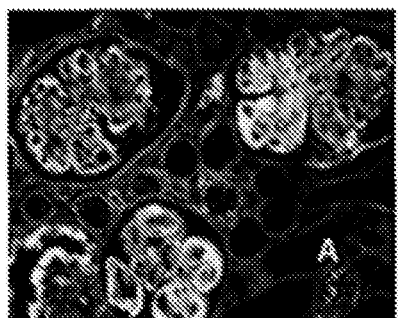
FIG. 5A shows kidney sections of control lupus mice treated with PBS probed with anti-mouse IgG-FITC Fc specific antibodies.
Figure 5B:
FIG. 5B and FIG. 5C show kidney sections of control lupus mice treated with PBS probed with anti-mouse IgG-FITC Fc specific antibodies stained with Periodic acid-Schiff (PAS).
Figure 5C:
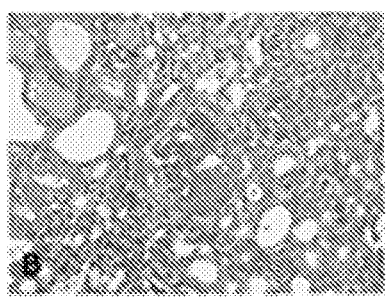

Kidney sections from lupus mice treated with PC-OVA (FIGS. 3A-3B), MPC (FIGS. 4A-4B) and PBS (FIGS. 5A-5C) were analyzed for glomerulonephritis. Two staining procedures were applied (i) histological staining (PAS); and (ii) immunohistological staining of immune complex deposits in the mesangium of the kidney using anti-mouse-Fc-FITC conjugate. As illustrated in FIGS. 5A-5C, mice treated with PBS showed severe (stage VI) glomerulonephritis exemplified by strong immune complex deposits (5A), diffused proliferating glomerulonephritis (5B) and crescent necrotizing glomerulonephritis (5C). However, at the same time point of 34 weeks lupus mice treated with MPC (FIGS. 4A-4B) and PC-OVA (FIGS. 3A-3B), exhibited only early stage (stage II) of glomerulonephritis.

Figure 6:
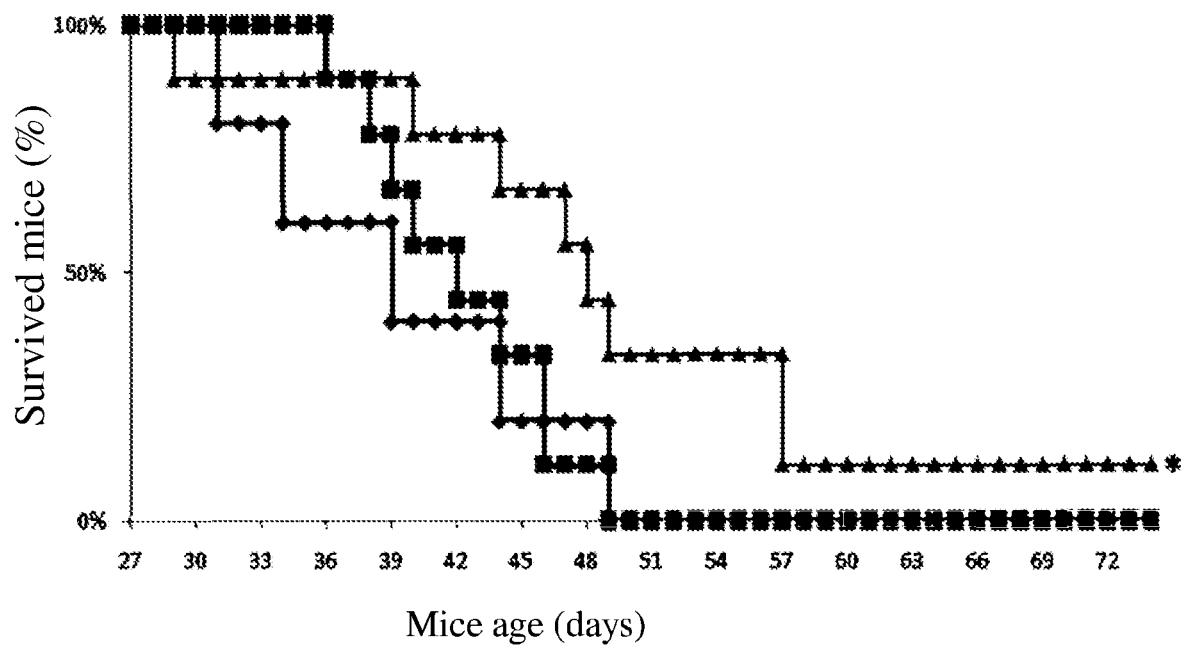
FIG. 6 is a Kaplan-Meier graph demonstrating survival of lupus mice treated with PC-OVA (triangle; *=$p<0.01$), MPC (square; $p<0.04$) or PBS (control; diamond).

A Kaplan-Meier analysis indicates that the survival time of lupus mice treated with PC-OVA (FIG. 6, triangle) was significantly longer (FIG. 6 *=$p<0.01$) compared to PBS treated mice (FIG. 6, diamond). The survival time of MPC treated mice (FIG. 6, square) showed only tendency of significance ($p<0.04$).

Example 2

The Effect of PC-tuftsin on Development of Proteinuria In Vivo

Phospholipids are non-immunogenic, thus, PC was conjugated to tuftsin (threonine-lysine-proline-arginine, TKPR; SEQ ID NO: 17) which may serve as an immunomodulatory molecule. In autoimmune models, such as EAE and lupus, PC and PC conjugated to keyhole limpet hemocyanin (KLH) or bovine serum albumin (BSA) had an inhibitory effect on disease progression (Dagan S et al., J. Biol. Response Mod. 1987, 6(6):625-636). PC conjugated to tuftsin was synthesized based on Michaelson Chemistry. The PC derivative, 4-aminophenylphosphorylcholine, used for the conjugate construction, was purchased from Biosearch Technologies.

The effect of PC-tuftsin (TPC) on proteinuria was determined in a mouse model for lupus, specifically, female NZBXW/F1 mice that develop lupus on a genetic background. Proteinuria levels were measured using Multistix (Bayer Diagnostics). This type of measurement is typically used in the clinic for assessing manifestation of lupus nephritis. Lupus nephritis is an inflammation of the kidney caused by systemic lupus erythematosus (SLE).

The mice, from age of 14 weeks, received subcutaneously PC-tuftsin at the concentration of 50 µg/0.1ml per mouse (treatment; n=10) or PBS (control; n=10), three times a week. Proteinuria was defined as having a protein level of above 100 mg/dl in the urine.

Figure 7:
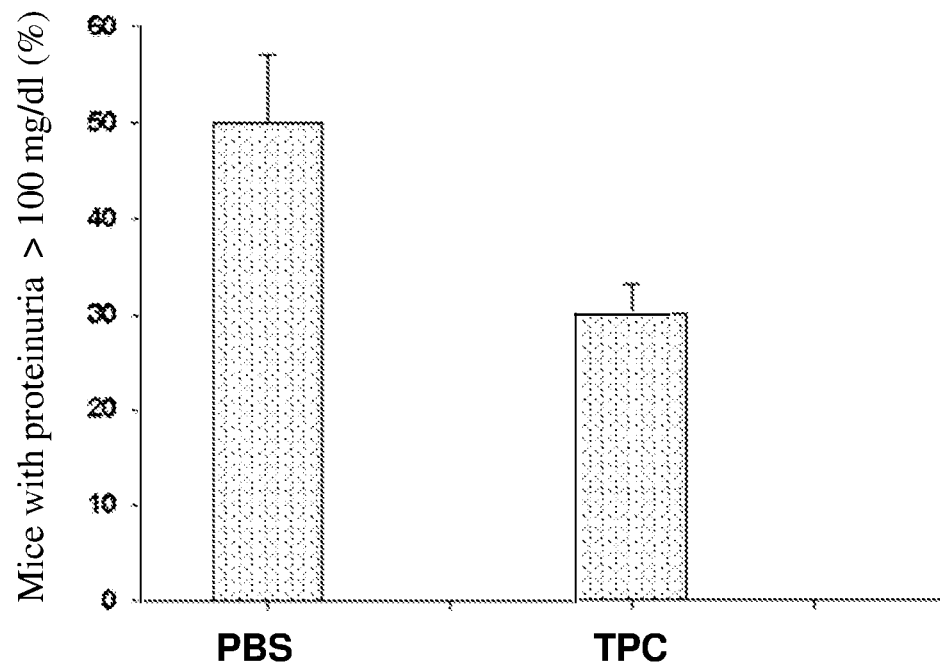
FIG. 7 shows the percentage of lupus mice with proteinuria (protein level above 100 mg/dl) treated with PC-tuftsin (TPC) or PBS (control), $p<0.02$.

The results demonstrate the inhibitory effect of PC-tuftsin treatment on the development of glomerulonephritis. As shown in FIG. 7, a significant attenuation (p<0.02) in proteinuria was exhibited in the group of mice treated with PC-tuftsin (TPC) in comparison with the control group, i.e. mice which received only the carrier (PBS).

Example 3

The Effect of PC-tuftsin on the Morphology of Kidneys In Vivo

The effect of PC-tuftsin on the morphology of kidneys was determined in a lupus mouse model as in Examples 2. Kidney section obtained from kidneys of mice sacrificed after treatments were paraffin embedded. PAS staining was used to detect pathology of nephritis. Immunofluorescence staining was used for detecting immune complex deposits. The latter was implemented by incubating the paraffin embedded sections with FITC-conjugated-anti-mouse-IgG. Evaluation was performed by a pathologist.

Mice, from age of 14 weeks, received subcutaneously PC-tuftsin at the concentration of 50 µg/0.1ml per mouse (treatment; n=10) or PBS (control; n=10), three times a week.

Figure 8A:
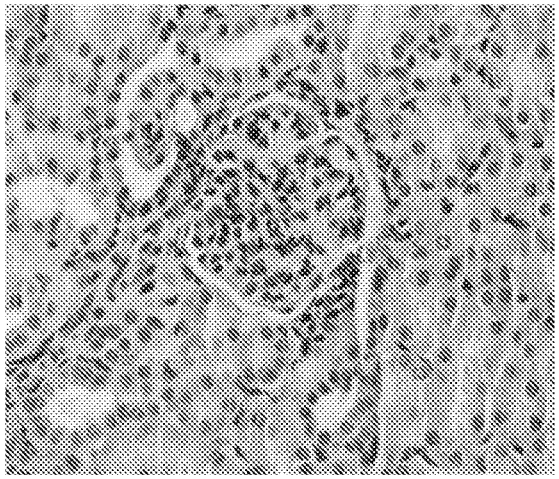
FIG. 8A shows PAS stained kidney sections of lupus mice treated with PBS (control).
Figure 8B:
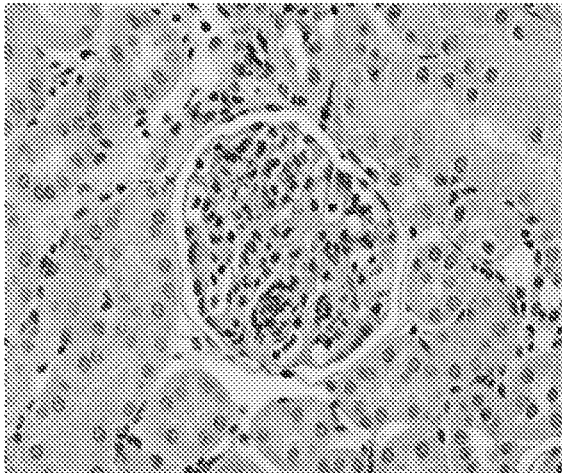
FIG. 8B shows PAS stained kidney sections of lupus mice treated with PC-tuftsin.

The results demonstrate a significant inhibitory effect of PC-tuftsin on the development of glomerulonephritis. Specifically, as illustrated in FIGS. 8A-8B, mice treated with PC-tuftsin did not display any pathology of nephritis, a normal glomeruli is exemplified (FIG. 8B; x60). Whereas the control group, i.e. mice which received only the carrier (PBS), presented a severe glomerulonephritis, strong destruction of the glomeruli, as well as infiltration of lymphocytes (FIG. 8A; x60).

Figure 9A:
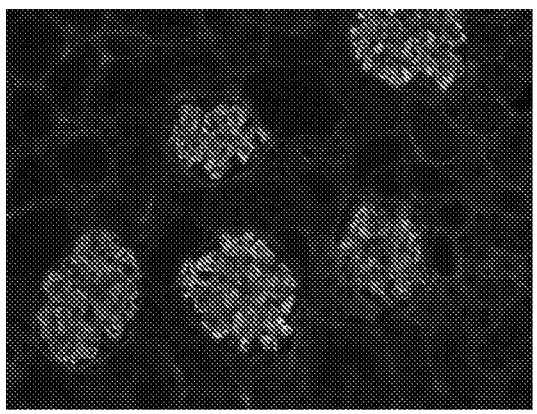
FIG. 9A shows kidney sections of lupus mice treated with PBS (control) probed with anti-mouse IgG-FITC Fc specific antibodies.
Figure 9B:
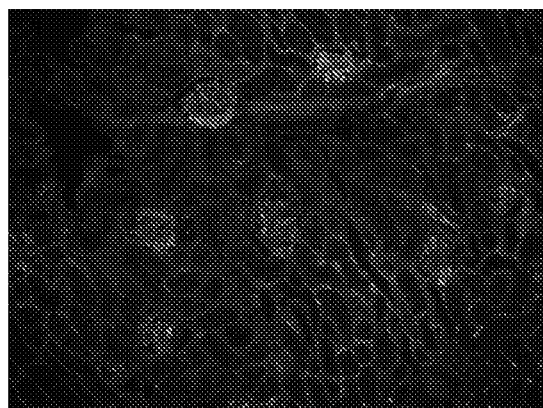
FIG. 9B shows kidney sections of lupus mice treated with PC-tuftsin probed with anti-mouse IgG-FITC Fc specific antibodies.

As shown in FIGS. 9A-9B, in lupus mice treated with PC-tuftsin, very mild immune complex deposits were exhibited in the glomeruli (FIG. 9B; x40) as compared to the control group (PBS), which present severe immune complex deposits (FIG. 9A; x20).

Example 4

The Effect of PC-tuftsin on the Immune System In Vivo

The effect of PC-tuftsin on the immune system was determined in the lupus mouse model as in Examples 2. Cytokines analyses and T regulatory cell profiling were measured; these types of studies are typically used in the clinic for assessing manifestation of lupus nephritis.

Mice, from age of 14 weeks, received subcutaneously PC-tuftsin at the concentration of 50 µg/0.1 ml per mouse (treatment; n=10) or PBS (control; n=10), three times a week. In the cytokines studies, the relative mRNA expression levels of pro-inflammatory cytokine IFNγ and anti-inflammatory cytokine TGFβ were analyzed by real time RT-PCR using LightCycler (Roche). Total RNA was isolated from splenocytes and was reverse-transcribed into cDNA by using Moloney Murine Leukemia Virus Reverse Transcriptase (Promega). The resulting cDNA was subjected to real-time RT-PCR in the presence of specific primers, according to the manufacturer's instructions (Table 2). The relative expression levels of IFNγ and TGFβ were normalized to β-actin levels.

TABLE 2

RT-PCR primers (forward and reverse respectively)

| Primer | Sequence (5' to 3') | SEQ. ID NO: |
|---|---|---|
| IFNγ | gaacgctacacactgc | 1 |
| IFNγ | ctggacctgtgggttg | 2 |
| IL-β | ccccaactggtaaatca | 3 |
| IL-β | ccgaggactaaggagtg | 4 |
| IL-10 | aacctcgtttgtacctct | 5 |
| IL-10 | caccatagcaaagggc | 6 |
| IL-17a | gggcaagggatgctctctag | 7 |
| IL-17a | ctgaagctgctgcagagctg | 8 |
| TNF-α | acgtcgtagcaaaccac | 9 |
| TNF-α | agatagcaaatcggctg | 10 |
| TGF-β | gaaccccattgctgt | 11 |
| TGF-β | gccctgtattccgtct | 12 |
| Foxp3 | taccacaatatgcgaccc | 13 |
| Foxp3 | ctcaaattcatctacggtcc | 14 |
| β-actin | gtgacgttgacatccg | 15 |
| β-actin | cagtaacagtccgcct | 16 |

Figure 10:
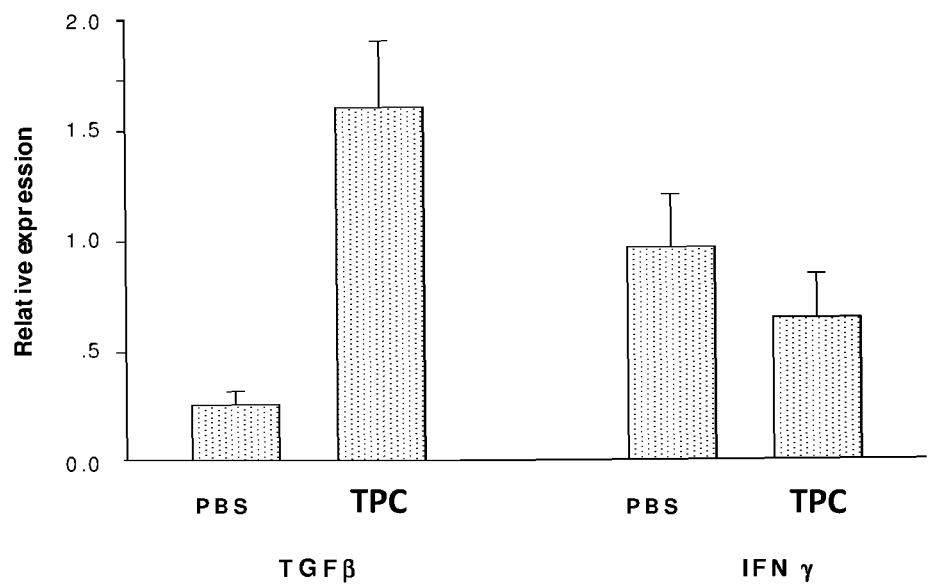
FIG. 10 shows relative mRNA expression levels of anti-inflammatory cytokine TGFβ ($p<0.001$) and pro-inflammatory cytokine IFNγ ($p<0.03$; relative to (3-actin) in the splenocytes of lupus mice treated with PC-tuftsin (TPC) or PBS.

The results demonstrate that PC-tuftsin (TPC) exerts a significant inhibitory effect on the development of glomerulonephritis. As shown in FIG. 10, the splenocytes relative mRNA expression of anti-inflammatory cytokine TGFβ in mice treated with PC-tuftsin was significantly enhanced in comparison to the TGFβ mRNA derived from the PBS treated mice (p<0.001). In contrast, the splenocytes relative mRNA expression level of pro-inflammatory cytokine IFNγ in mice treated with PC-tuftsin (TPC) was significantly reduced, i.e. ameliorated in comparison to the IFNγ mRNA of the PBS control group (p<0.03). The results indicate that PC-tuftsin inhibited development of inflammation associated with nephritis.

Splenocytes protein level of anti-inflammatory cytokines TGFβ, and IL-10 and pro-inflammatory cytokines IFNγ, and IL-17 were quantified by DuoSet (R&D Systems), according to the manufacturer's instructions. Briefly, spleens from mice treated with PC-tuftsin or PBS were harvested, splenocytes were isolated (5×10$^6$/ml) and incubated for 72 hours and thereafter assessed for contents of secreted cytokines.

Figure 11:
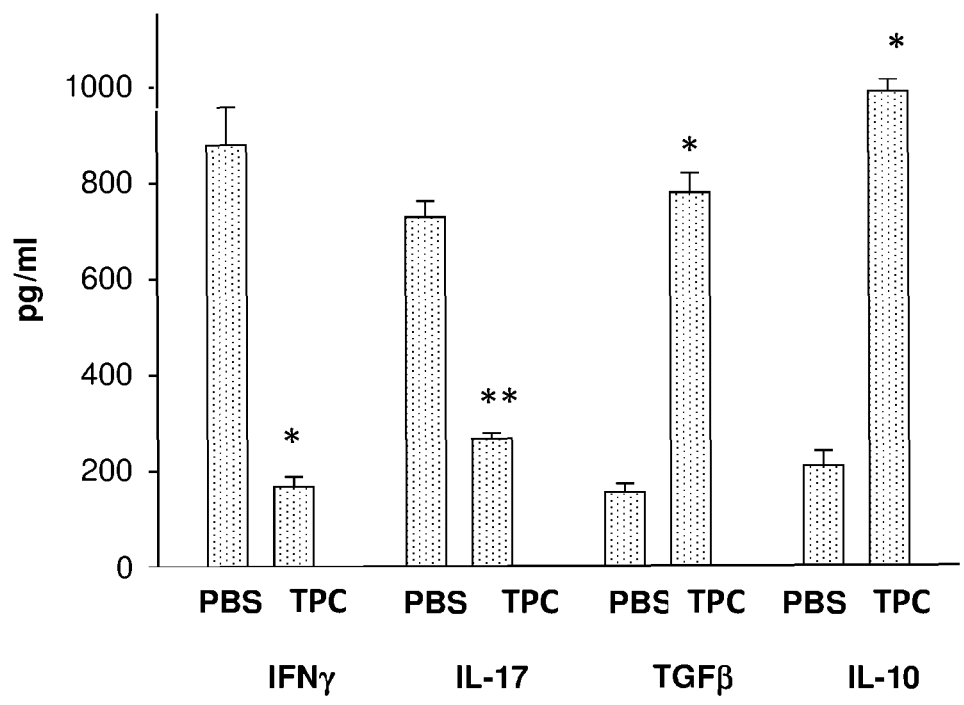
FIG. 11 shows protein level (in units of pg/ml) of anti-inflammatory cytokines TGFβ and IL-10 and pro-inflammatory cytokines IFNγ and IL-17 in the splenocytes of lupus mice treated with PC-tuftsin (TPC) or PBS (control) .*=$p<0.001$, **=$p<0.02$.

The results demonstrate a significant inhibitory effect exerted by PC-tuftsin on the development of glomerulonephritis. As shown in FIG. 11, mice treated with PC-tuftsin (TPC) exhibited 5.1 and 4.8 increase in the protein levels of anti-inflammatory cytokines, TGFβ and IL-10, respectively, in comparison to PBS treatment (p<0.001). At the same time, the concentrations of pro-inflammatory cytokines IFNγ and IL-17 in PC-tuftsin (TPC) treated mice reduced by 5.2 and 2.7 fold, respectively as compared to control group (p<0.001, p<0.02, respectively). These results further indicate that PC-tuftsin treatment results with a significant inhibition of pro-inflammatory cytokines and enhanced expression of anti-inflammatory cytokines, thereby reduces, and even prevents, the occurrence of nephritis.

Finally, a T regulatory cell (Tregs) profiling assay was performed in isolated splenocytes incubated with the following antibodies: anti-CD4+FITC, anti-CD25+APC and anti-FOXP3+PE (eBioscience) and analyzed by FACS. Forward and side scatter gates adjusted to include all cells and to exclude debris (Becton Dickinson). Cells were gated on CD4+cells, and for intracellular staining, the cells were incubated with a fixation solution, washed and resuspended in permeabilization solution (Serotec). Isotype control was used as reference.

Figure 12:
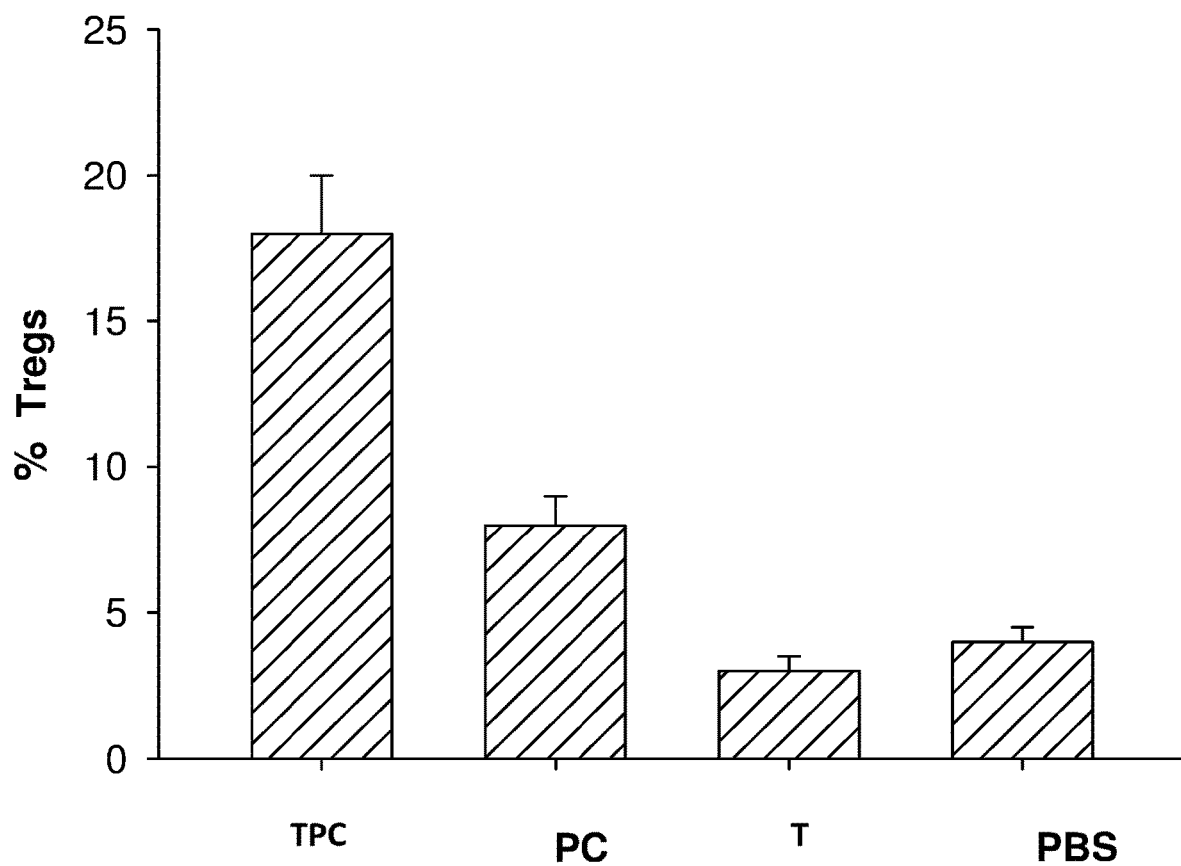
FIG. 12 shows FACS analysis of T regulatory cells levels (Tregs—$CD4^+$, $CD25^+$, $FOXP3^+$) in lupus mice treated with PC-tuftsin (TPC; $p<0.02$), phosphorylcholine (PC; $p<0.01$), tuftsin (T; $p<0.01$) or PBS ($p<0.01$).

Here too, the results demonstrate a significant inhibitory effect of PC-tuftsin treatment on the development of glomerulonephritis. As shown in FIG. 12 mice treated with PC-tuftsin (TPC) presented an enhancement of 18±2 percent in the Tregs, CD4+CD25+FOXP3+ expression level ($p<0.02$), whereas with PBS treated mice an increase of only 4±0.6 percent was observed ($p<0.01$). Notably, phosphorylcholine (PC) or tuftsin (T) did not cause any significant elevation in Tregs level, ($p<0.01$). Moreover, the relative amount of Tregs obtained with PC-tuftsin is higher than the sum of relative Tregs obtained from each of PC and tuftsin. Thus, the PC-tuftsin exhibits a synergistic therapeutic effect.

Example 5

Synthesis of a Tuftsin-derived-phosphorylcholine (TD-PC) Conjugate

Tuftsin was extended at its C-terminal thereby forming Thr-Lys-Pro-Arg-Glv-Tyr (TD; SEQ ID NO: 25). TD-PC was synthesized manually following solid phase peptide technology. The peptide was coupled to diazotized 4-aminophenyphosphorylchloride to form an azo bond between the tuftsin derivative (SEQ ID NO: 25) and PC. The conjugate TD-PC was characterized by mass spectra, amino acid analysis as well as by High-performance liquid chromatography (HPLC).

Example 6

The Effect of PC-tuftsin Derivative on Colitis Development In Vivo

The effect of PC-tuftsin derivative (SEQ ID NO: 25) on colitis development was determined in a mouse model subjected to induction of acute colitis by dextran sulfate sodium (DSS) treatment. Specifically, induction of colitis was carried out in male C57BL/6 mice ("colitis mice") by supplementing the drinking water (2.5% wt/v) for five days with DSS (mol. wt. 36,000-50,000).

Two groups of mice were fed daily via oral ingestion using a feeding-needle, with PC-tuftsin derivative at a concentration of 500p.g/0.1ml per mouse (treatment; n=10), or PBS (control; n=10). These compounds were given during 11 days starting two days before DSS administration. A third group of mice (n=10) were not induced with colitis, i.e. did not receive DSS, nor any treatment. All the mice groups had an identical average body weight (27-29 gr).

Figure 13:
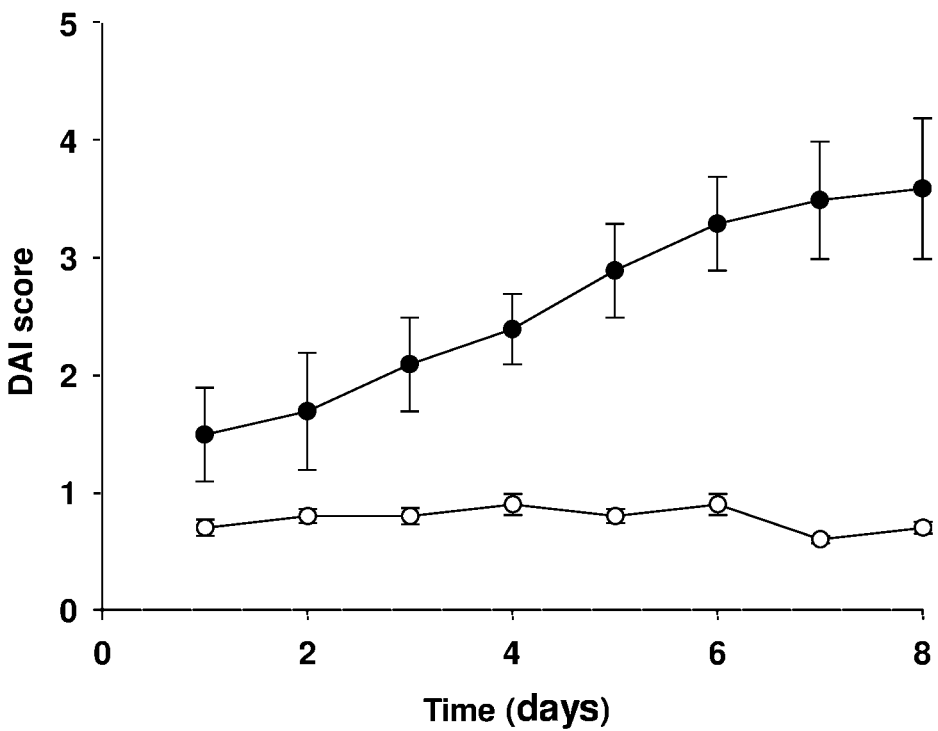
FIG. 13 shows progression over time as a function of daily disease activity (DAI; $p<0.02$) in mice subjected to DSS induction of inflammatory bowel disease ("IBD mice") following treatment with PC-tuftsin derivative (TD-PC) as set forth in SEQ ID NO: 25 (empty circle) and PBS (solid circle).

Assessment of colitis development was performed by monitoring body weight, rectal bleeding, stool consistency, and survival every second day. Intestinal bleeding was followed by Hemoccult test and observation of bleeding signs on the anus or gross bleeding. The daily disease activity index (DAI) was calculated by grading on a scale of zero to four the following parameters: change in weight (0, <1%; 1, 1-5%; 2, 5-10%; 3, 10-15%; and 4, >15%), intestinal bleeding (0, negative; 4, positive), and stool consistency (0, normal; 2, loose stools; 4, diarrhea). The combined scores were then divided by three to obtain the final disease activity index. Ten days following disease induction, mice were sacrificed and the large intestine was collected and evaluated for colon length and microscopic colonic damage. For microscopic scoring, the proximal, medial, and distal portions of the colon and the cecum were fixed in 10% phosphate-buffered formalin. Paraffin-embedded sections were stained with H&E. The degree of histological damage and inflammation was graded in a blinded fashion by an expert pathologist The results demonstrate an amelioration effect of PC-tuftsin derivative on the development of DSS induced colitis, As shown in FIG. 13, the DAI score of colitis mice treated with PC-tuftsin derivative (empty circle) was around 0.9 ($p<0.02$) at the last day of the experiment, day 8, which was significantly lower than the DAI of the control group (PBS, solid circle). The latter gradually increased with time reaching the value of 2.6 after 5 days.

Figure 14:
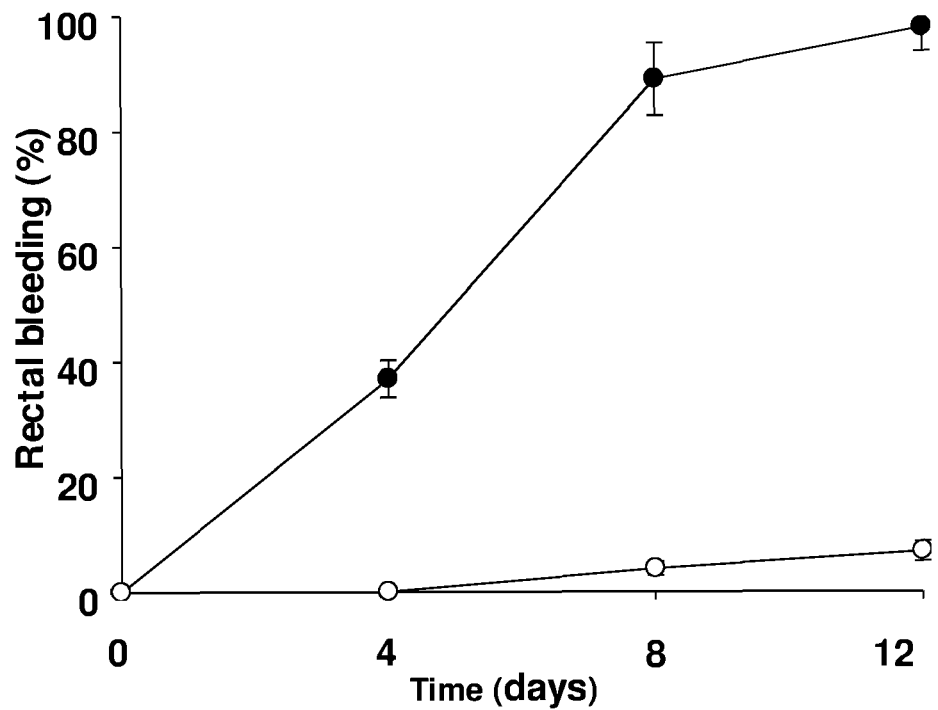
FIG. 14 shows rectal bleeding in IBD mice following treatment with PC-tuftsin derivative as set forth in SEQ ID NO: 25 (empty circle) and PBS (solid circle) ($p<0.001$).
Figure 15:
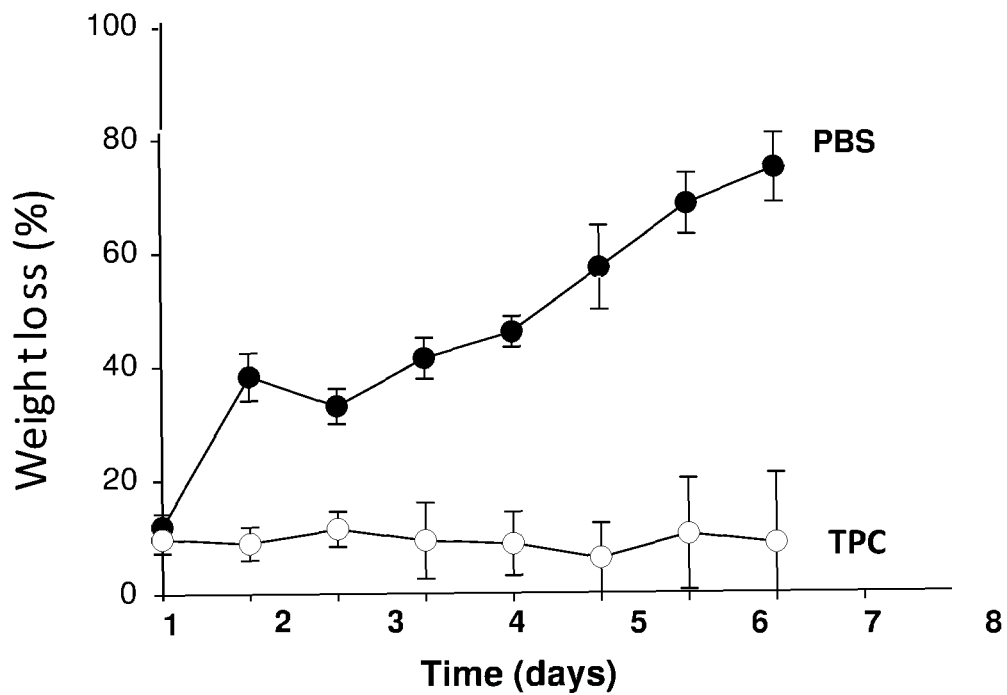
FIG. 15 shows weight loss in IBD mice following treatment with PC-tuftsin derivative as set forth in SEQ ID NO: 25 (TD-PC, empty circle) and PBS (solid circle) relative to t=0 ($p<0.001$).
Figure 16:
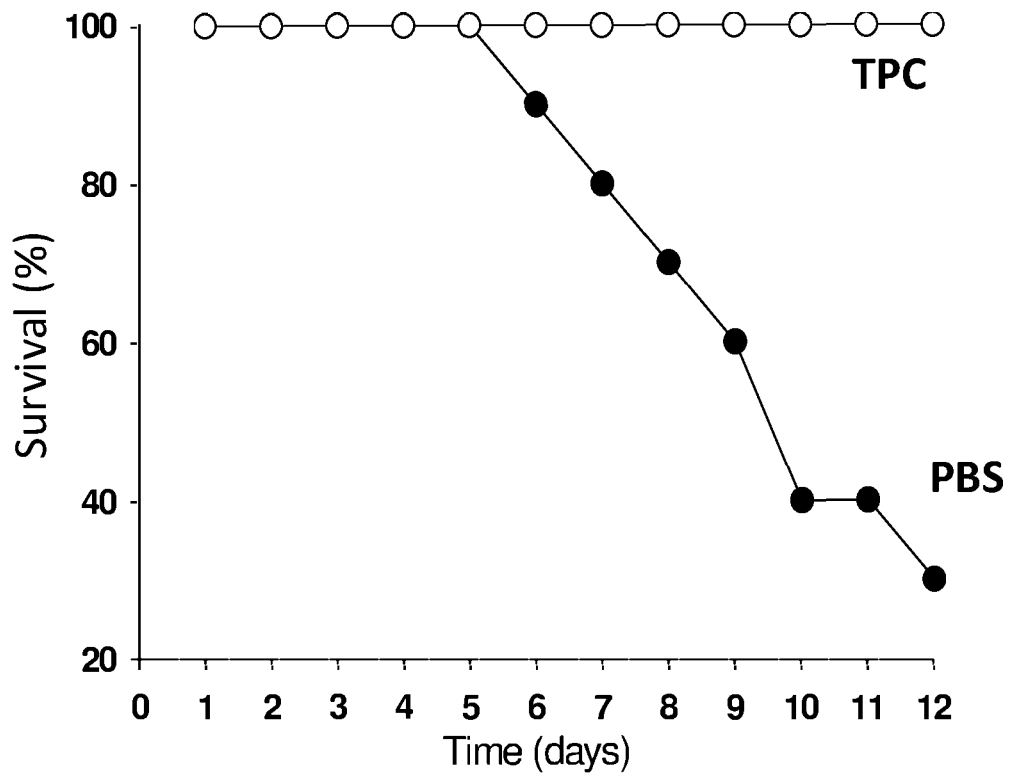
FIG. 16 shows survival of IBD mice following treatment with PC-tuftsin derivative (TD-PC) as set forth in SEQ ID NO: 25 (empty circle) and PBS (solid circle).

Furthermore, as illustrated in FIGS. 14-15, mice treated with PC-tuftsin derivative (empty circle) exhibited significantly low rectal bleeding (FIG. 14; $p<0.001$) and loss of weight (FIG. 15; $p<0.001$) in comparison with the control (PBS treated, solid circle) mice. Finally, as illustrated in FIG. 16, mice treated with PC-tuftsin derivative (empty circle) exhibited significantly higher survival. After 5 days, a drop in the survival was exhibited with the PBS treated mice (solid circles), whereas 100% of the mice treated with PC-tuftsin (empty circle) were still alive, even after day 12.

Figure 17:
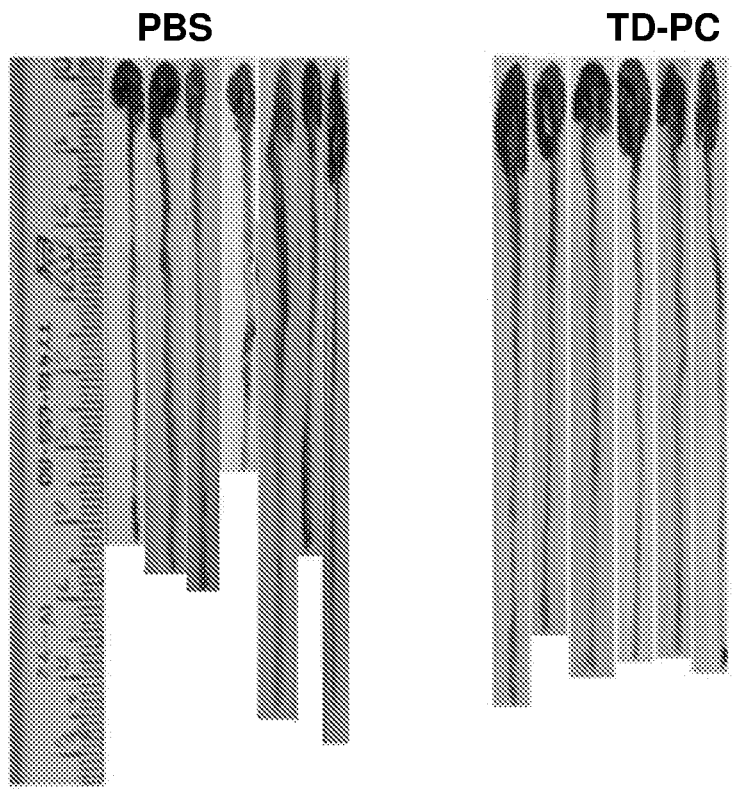
FIG. 17 shows colons of IBD mice following treatment with PC-tuftsin derivative (SEQ ID NO: 25; TD-PC) or PBS.
Figure 18:
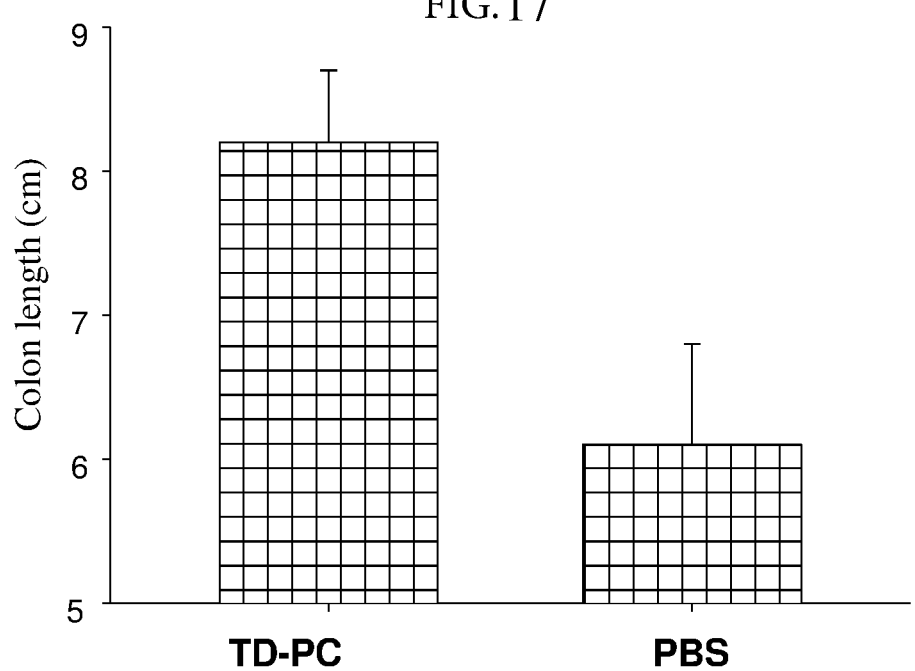
FIG. 18 shows colon length analysis ($p<0.02$) in IBD mice following treatment with PC-tuftsin derivative (TD-PC) or PBS.
Figure 19A:
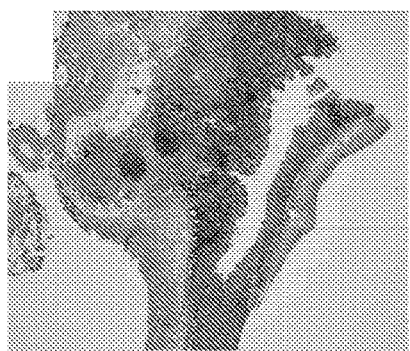
FIG. 19A and FIG. 19D show H&E stained colon sections of IBD mice treated with PBS (control).
Figure 19B:
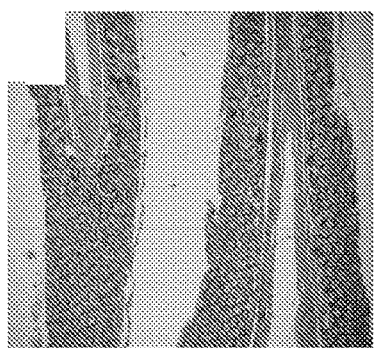
FIG. 19B and FIG. 19E show H&E stained colon sections of IBD mice treated with PC-tuftsin derivative.
Figure 19C:
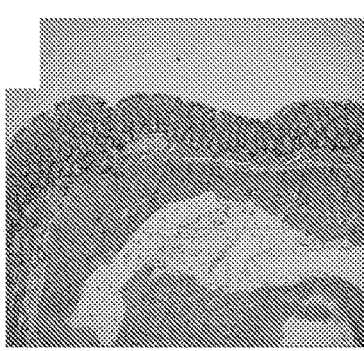
FIG. 19C and FIG. 19F show H&E stained colon sections from a mouse not subjected to DSS induction of IBD.
Figure 19D:
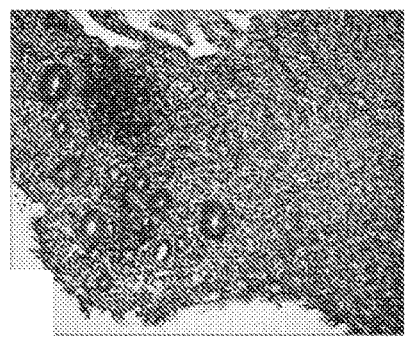
Figure 19E:
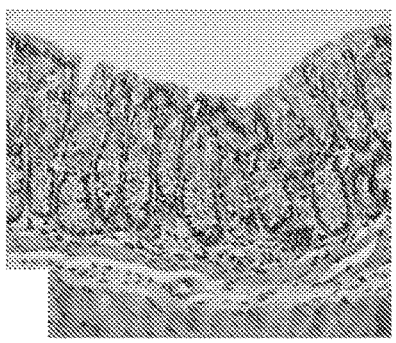
Figure 19F:
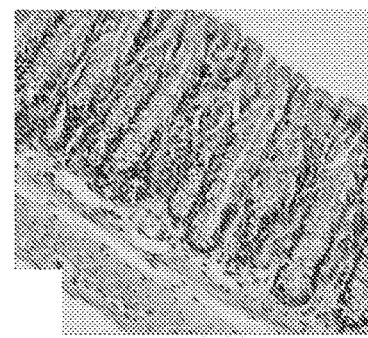

As exemplified in FIGS. 17-18, the colon length of mice treated with PC-tuftsin (TD-PC) was eight cm, in comparison with the control (PBS treated) mice, which shortened from eight cm to five-six cm ($p<0.02$).

Finally, as shown in FIG. 19, panels A-F, histological analyses of colon section from the colons of all three mice groups revealed that PC-tuftsin derivative (TD-PC) treatment (FIG. 19-panel B x20, panel E x60) attenuated colon destruction as oppose to the control treatments, namely, PBS treatment (FIG. 19-panel A x10, panel D x40) and healthy mice, i.e. mice not subjected to DSS induction of colitis (FIG. 19 - panel C x20, panel G x60). No difference was noted in the structure of the colon epithelia in healthy mice (FIG. 19, panel C, panel F) nor in colitis mice treated with TD-PC (FIG. 19, panel B, panel E), whereas a strong infiltration of cells and zoom out of the glands were seen in colitis mice treated with PBS (FIG. 19, panel A, panel D).

Example 7

Cytokines Expression in the Colon

Figure 20:
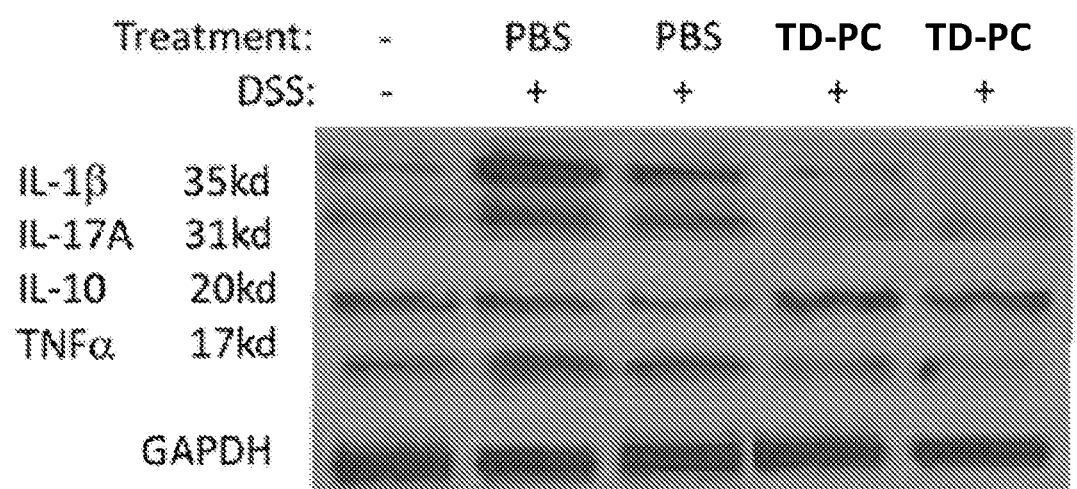
FIG. 20 shows immunoblot analysis of cytokines expression (TNFα, IL-17, IL-1β and IL-10) in the colons of mice following TD-PC or PBS treatments.

The expression of the proinflammatory cytokines (TNFα, IL-17, IL-1β) and anti-inflammatory cytokine IL-10 was analyzed by immunoblot in colon lysates. The expression of TNFα, IL-17 and IL-1β was suppressed in cell lysates taken from TD-PC-treated mice, suggesting that TD-PC (SEQ ID NO: 25 conjugated to PC) attenuated the expression of the pro-inflammatory cytokines. Significant increased IL-10 expression was documented, suggesting that TD-PC enhanced anti-inflammatory cytokine expression in the colon (FIG. 20).

Example 8

The Effect of TD-PC on Proteinuria Onset

Figure 21:
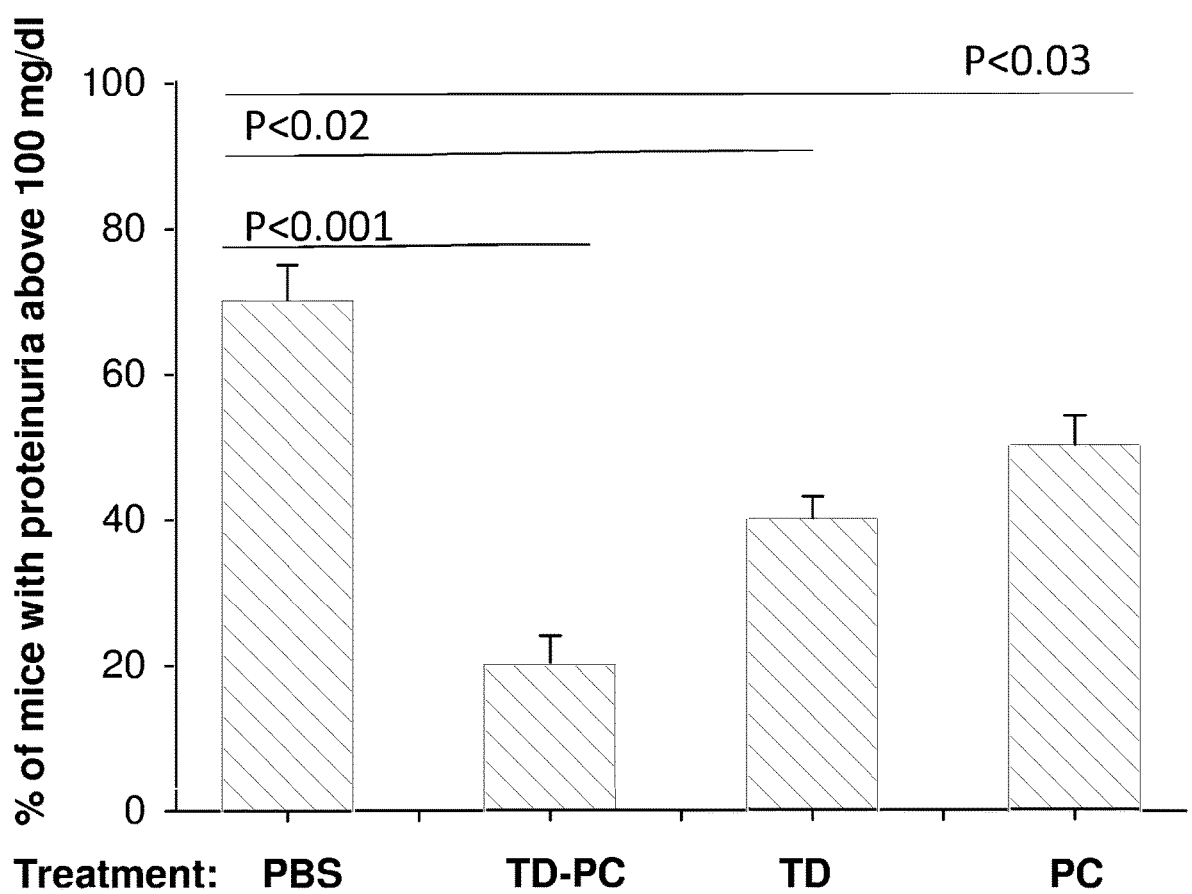
FIG. 21 shows the presence of proteinuria in NZBxW/F1 lupus control mice (PBS) or in mice treated with the TD-PC conjugate (TD-PC), the tuftsin derivative (TD) and phosphorylcholine (PC).

To examine the potential protective effect of TD-PC (SEQ ID NO: 25 conjugated to PC), female NZBxW/F1 lupus prone mice received subcutaneous injections (s.c) of the TD-PC conjugate, phosphorylcholine (PC), tuftsin derivative (SEQ ID NO: 25) or PBS (control) via a prophylactic protocol starting at week 14, before the clinical onset of lupus (n ¼ 15 per group). As illustrated in FIG. 21, at the age of 30 weeks, 72% of the mice treated with PBS developed proteinuria whereas only 21% of the TD-PC treatment group had proteinuria above 100 mg/dl. The TD-PC-treated mice showed a significant reduced onset of proteinuria as compared with control mice that received PBS, tuftsin derivative (SEQ ID NO: 25) or PC, all which when given separately served as controls for TD-PC ($p<0.001$, $p<0.02$, $p<0.03$ respectively). Without being bound by any theory or mechanism, it is concluded that TD-PC reduced the appearance of immune complex (IC) deposits in the mesangium of the TD-PC treated mice to class-II nephritis. In contrast, treatment with phosphorylcholine or PBS did not diminish the development of strong mesangial damage defined as class-IV. Tuftsin derivative (SEQ ID NO: 25) alone had a moderate but not significant effect on IC deposition.

Example 9

TD-PC Prolong of the Survival time of Lupus Mice

Figure 22:
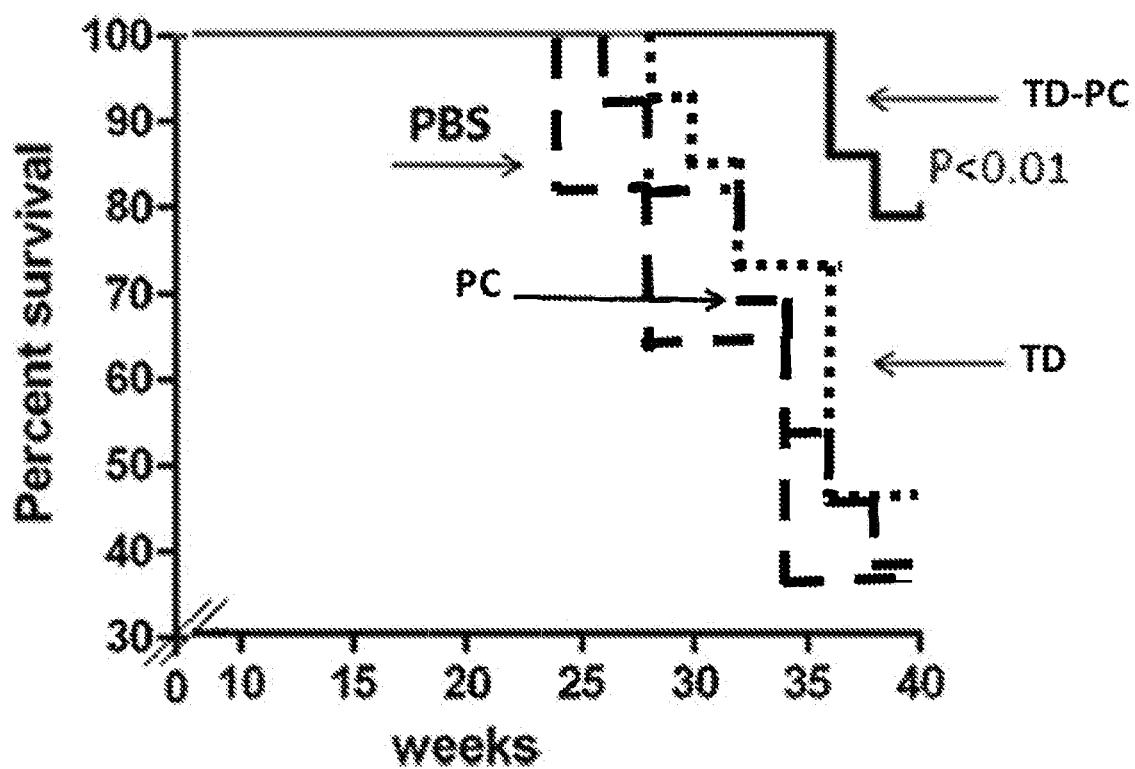
FIG. 22 is a Kaplan-Meier survival analysis of mice treated with TD-PC, tuftsin, PC or PBS.

A main complication of lupus nephritis is a short survival time due to severe kidney failure. Therefore, the survival time of mice treated either with TD-PC or with PC, tuftsin derivative (SEQ ID NO: 25) or PBS (control) was analyzed. As depicted in FIG. 22, a significant difference in survival time between the TD-PC treated mice and the control groups, between weeks 24th up to 40th week was observed. Additionally, a significant difference in the percentage of death number in mice was documented between PBS injected mice in comparison to PC, tuftsin derivative (SEQ ID NO: 25) and TD-PC treated mice already at week 24.

Example 10

TD-PC Therapy and Titers of Circulating Anti-dsDNA Antibodies

Figure 23:
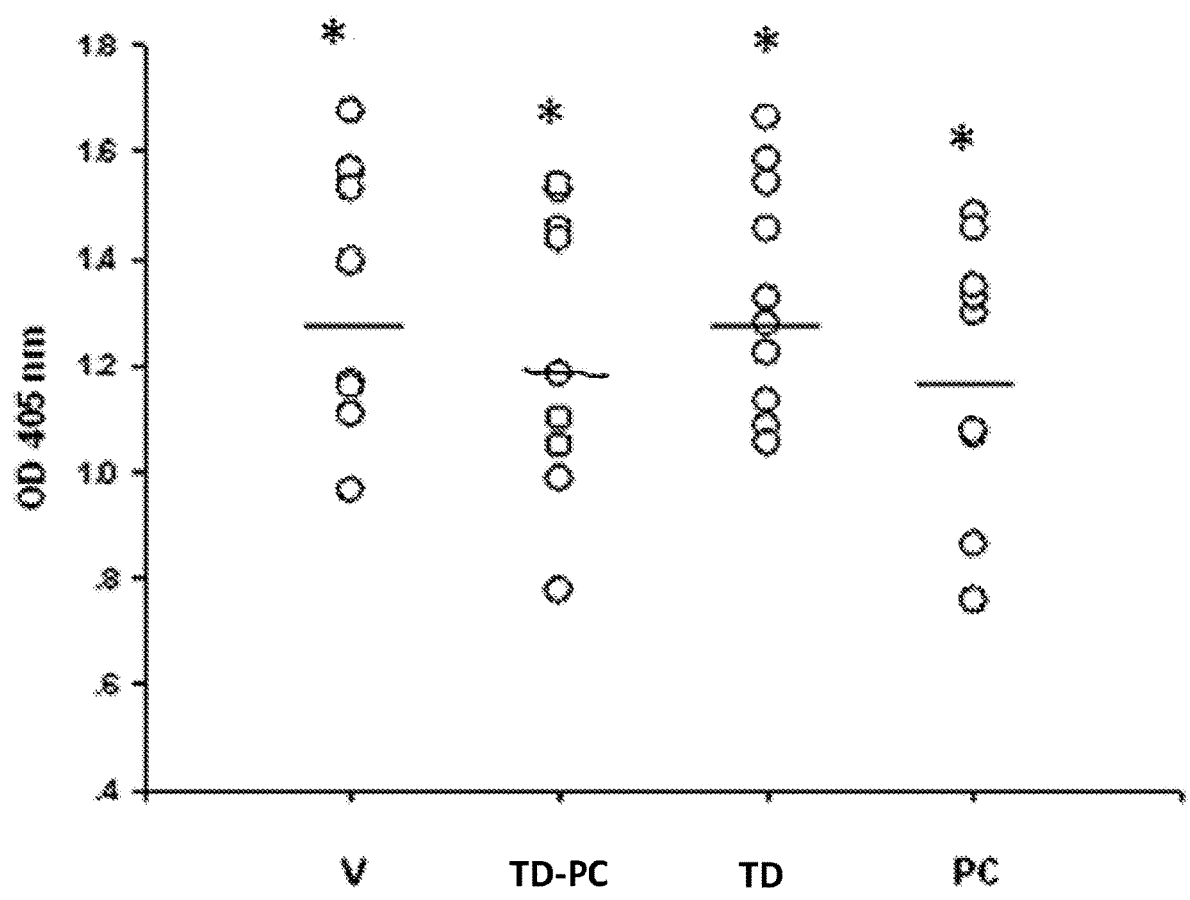
FIG. 23 shows titers of circulating anti-dsDNA antibodies in the sera of mice treated with TD-PC (TD-PC), the tuftsin derivative (TD), phosphorylcholine (PC) or PBS (V), obtained by ELISA at a dilution of 1:800 (n=10 per group).

Titers of circulating anti-dsDNA antibodies in the sera of control and treated mice were monitored during the development of lupus, and their levels were measured every 3 weeks. No statistically significant change was noticed between the group of mice treated with TD-PC (SEQ ID NO: 25 conjugated to PC), tuftsin derivative (TD; SEQ ID NO: 25), PC or PBS ($p>0.05$, FIG. 23). FIG. 23 presents the anti dsDNA antibodies titers in the sera at the age 30 weeks at a dilution of 1:800. A follow-up of anti-dsDNA antibodies over time (16-40 weeks) did not show any significant change between the different groups of mice ($p>0.05$; data not shown).

Example 11

Cytokines Profile Under Treatment of Lupus with TD-PC

Figure 24A:
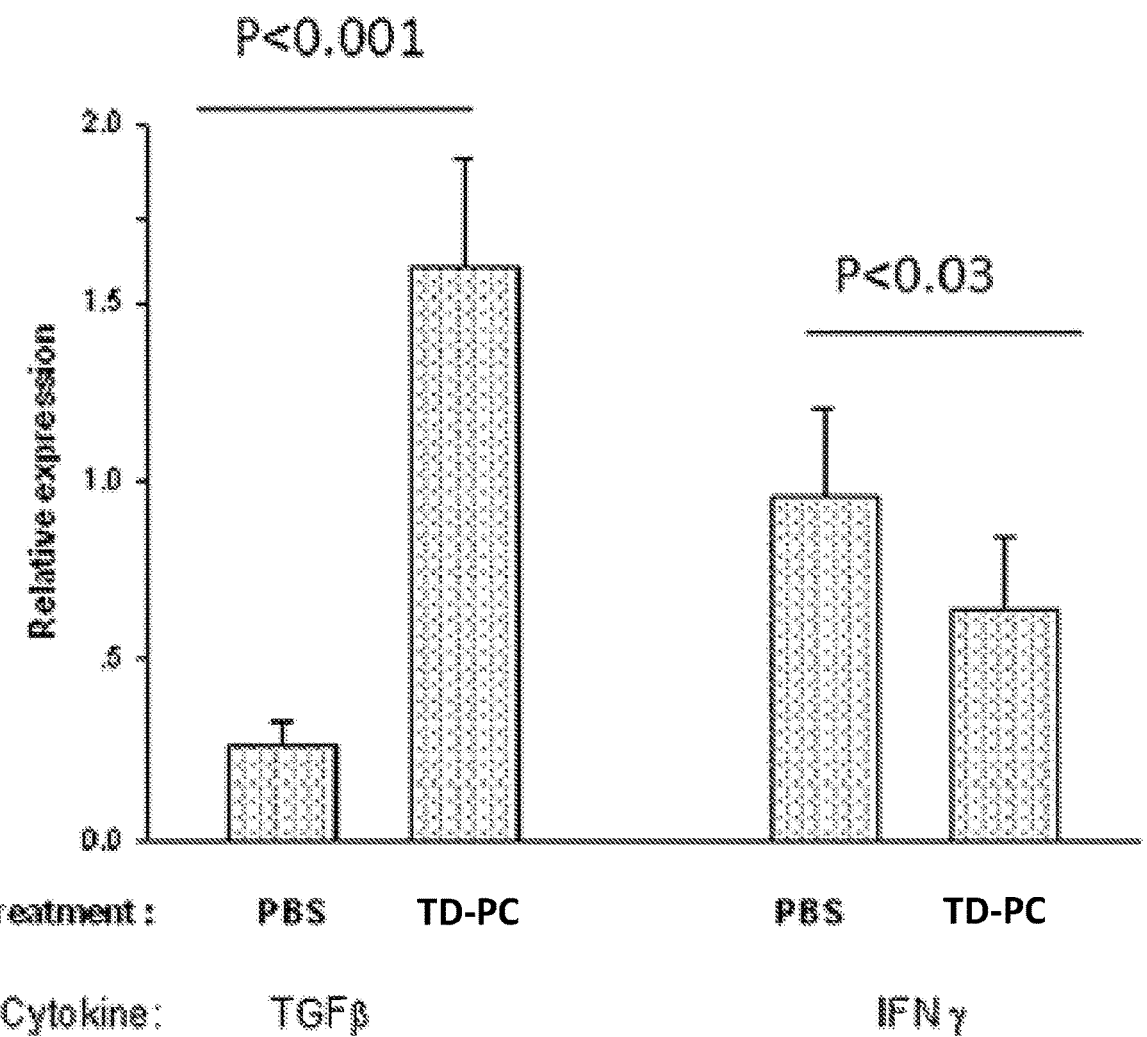
FIG. 24A shows the relative expression of IFNγ and TGFβ mRNAs in spleen cells derived from TD-PC or PBS (control) treated mice.

Cytokines were shown to play a major role in the pathogenesis of lupus. NZBXW/F1 female mice having lupus were treated with TD-PC (SEQ ID NO: 25 conjugated to PC) or the corresponding control treatments. Mice were sacrificed at week 30, and their splenocytes were studied in-vitro for the expression of pro-inflammatory cytokines (IFN-γ, IL-17) and anti-inflammatory (TGF(β, IL-10) cytokines using RT-PCR. It was found that TD-PC inhibited the mRNA expression of the pro-inflammatory cytokine IFNγ in comparison to the mRNA expressed in PBS treated mice ($p<0.03$; FIG. 24A). In contrast, TD-PC increased the mRNA expression of the anti-inflammatory cytokine TGFβ in the ($p<0.001$) compared to the mRNA expressed by splenocytes derived from PBS-treated mice (FIG. 24A).

Figure 24B:
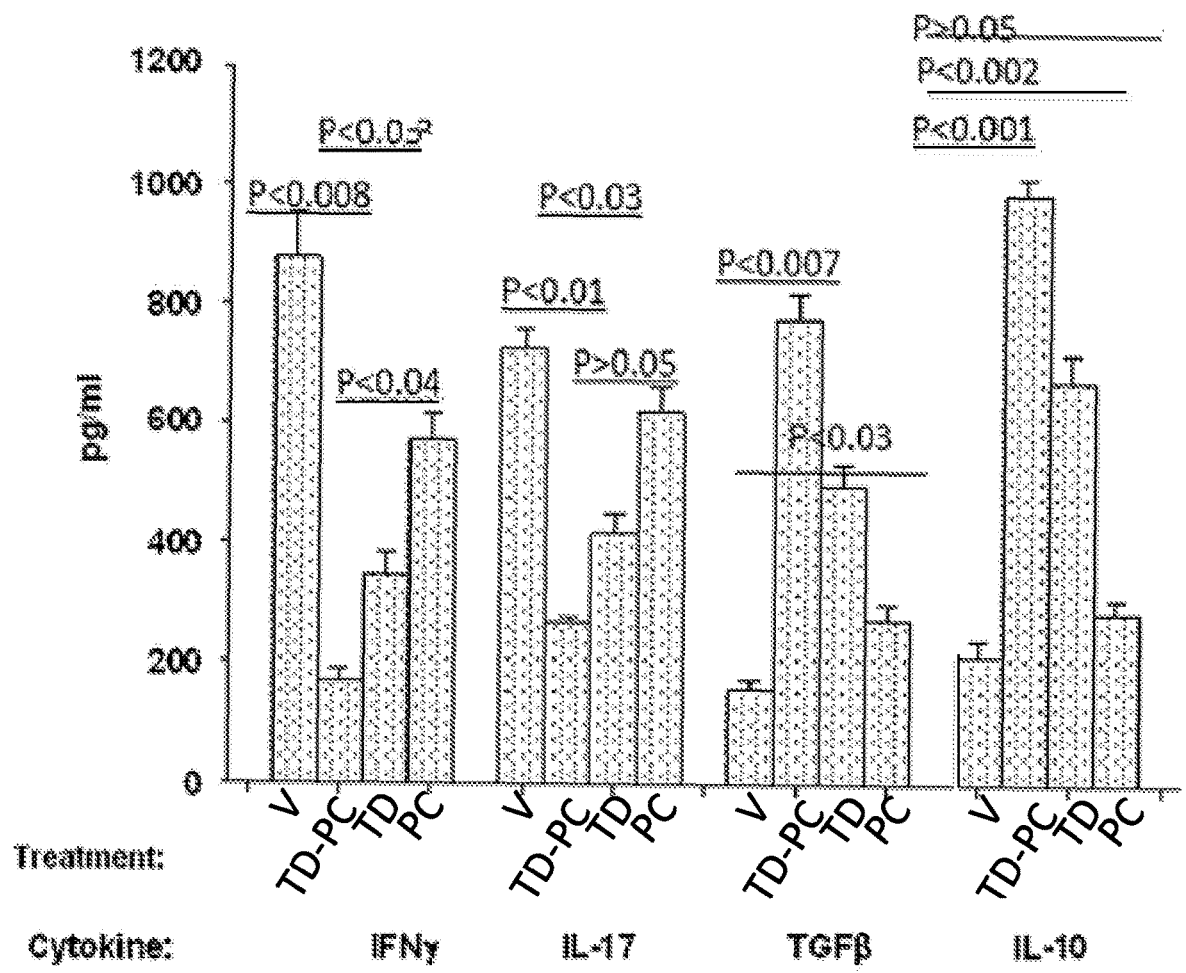
FIG. 24B shows the level of pro-inflammatory cytokines (IFNγ, IL-17) and anti-inflammatory cytokines (IL-10, TGFβ) in the culture fluids of splenocytes originated from mice treated with TD-PC (TD-PC), the tuftsin derivative (TD), phosphorylcholine (PC) or PBS (V).

Striking inhibition of pro-inflammatory cytokines (IFNβ, IL-17) secretion in-vitro by spleen cells originated from TD-PC treated mice is demonstrated in FIG. 24B. However, a prominent increase in anti-inflammatory cytokines (TGFβ, IL-10) secretion in-vitro by splenocytes derived from TD-PC treated mice is illustrated in FIG. 24B. TD-PC treatment reduced splenocyte secretion of IFNγ from lupus TD-PC treated mice by 5.2 times, compared to IFNγ secretion in spleen cells from PBS subjected mice ($p<0.008$; FIG. 24B). IFNγ secretion upon tuftsin derivative (SEQ ID NO: 25) or PC treatments was reduced by 2.5 and 1.5 times respectively ($p<0.03$ and $p<0.04$, respectively). A significant decline was observed in the levels of IL-17 secretion from splenocytes, in vitro, from TD-PC treated mice, ($p<0.01$), compared to control (PBS) mice. Less significant inhibition of IL-17 secretion was induced by tuftsin derivative (SEQ ID NO: 25; $p<0.03$) and to a lower extent by PC ($p<0.04$). TD-PC significantly upregulated the production of the anti-inflammatory cytokine TGFP splenocytes in-vitro ($p<0.007$), when compared to splenocyte secretion in control (PBS) mice. Tuftsin derivative (SEQ ID NO: 25) moderately enhanced the secretion of TGFβ, while PC had a minimal effect on this cytokine expression, ($p<0.05$). TD-PC remarkably increased IL-10 concentration in the culture fluid of splenocytes derived from TD-PC treated mice in comparison to splenocytes from control (PBS) mice ($p<0.001$). Treatment with tuftsin derivative (SEQ ID NO: 25) also increased IL-10 secretion by splenocytes in-vitro but less significant than treatment with TD-PC ($p<0.01$). Splenocytes from mice treated with PC did not have any effect on IL-10 secretion in-vitro.

Example 12

The Effect of TD-PC on the Expansion of Treg Cells

Figure 25A:
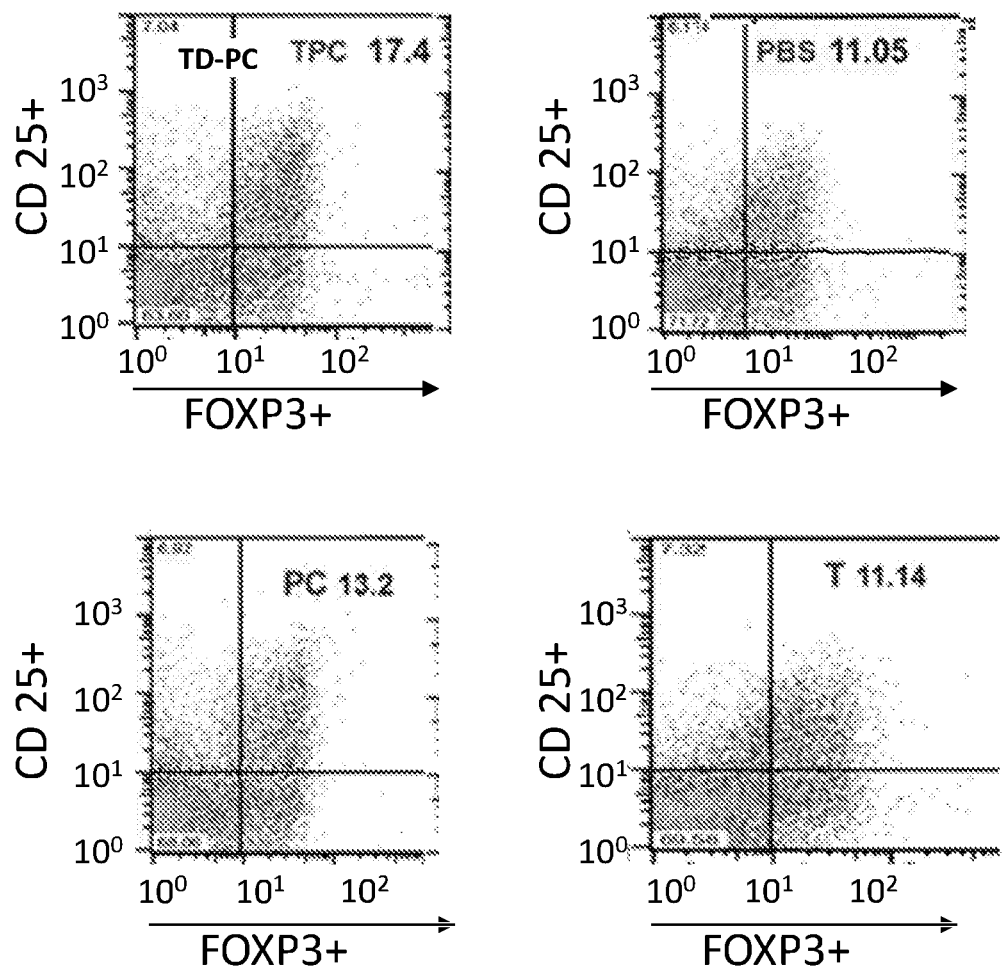
FIG. 25A shows FACS scans corresponding to the expansion of Tregs in mice treated with TD-PC (TD-PC), the tuftsin derivative (TD), phosphorylcholine (PC) or control (PBS).
Figure 25B:
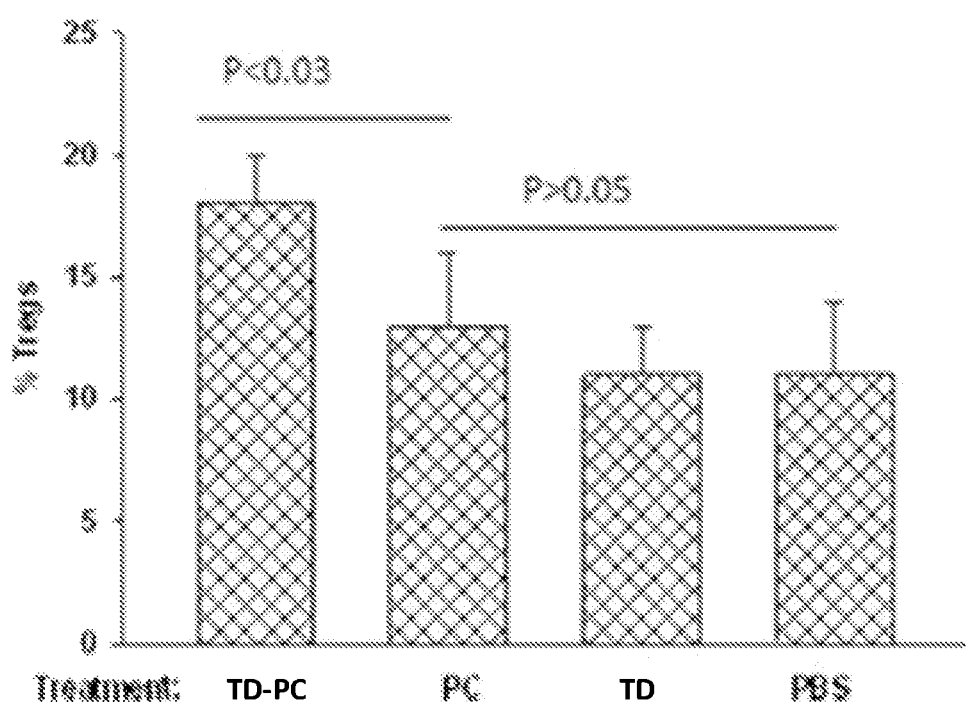
FIG. 25B shows a quantitative analysis corresponding to the FACS scans represented in FIG. 25A.

The percentage of CD4+CD25+FOXP3+ Tregs phenotype subset in spleen cells following treatment with TD-PC, tuftsin derivative (SEQ ID NO: 25), PC or PBS, is elucidated in FIGS. 25A-25B. A marked increase in Tregs phenotype was observed in the TD-PC treated group of mice when compared to Tregs levels in spleen cells of mice treated with tuftsin derivative (SEQ ID NO: 25), PC or PBS (18%, 8%, 3% and 4% respectively). Representative data of FACS scans gating on CD4+ T cells are presented in FIG. 25A. Statistics of several FACS analyses (N=15) is provided in FIG. 25B. The results indicate that TD-PC promoted significantly the Tregs phenotype expansion ($p<0.03$) compared to treatments/controls. Treatment with tuftsin derivative (SEQ ID NO: 25) and PC did not lead to Tregs expansion ($p>0.05$).

Example 13

TD-PC Reduces Arthritis in Mice with CIA

Figure 26A:
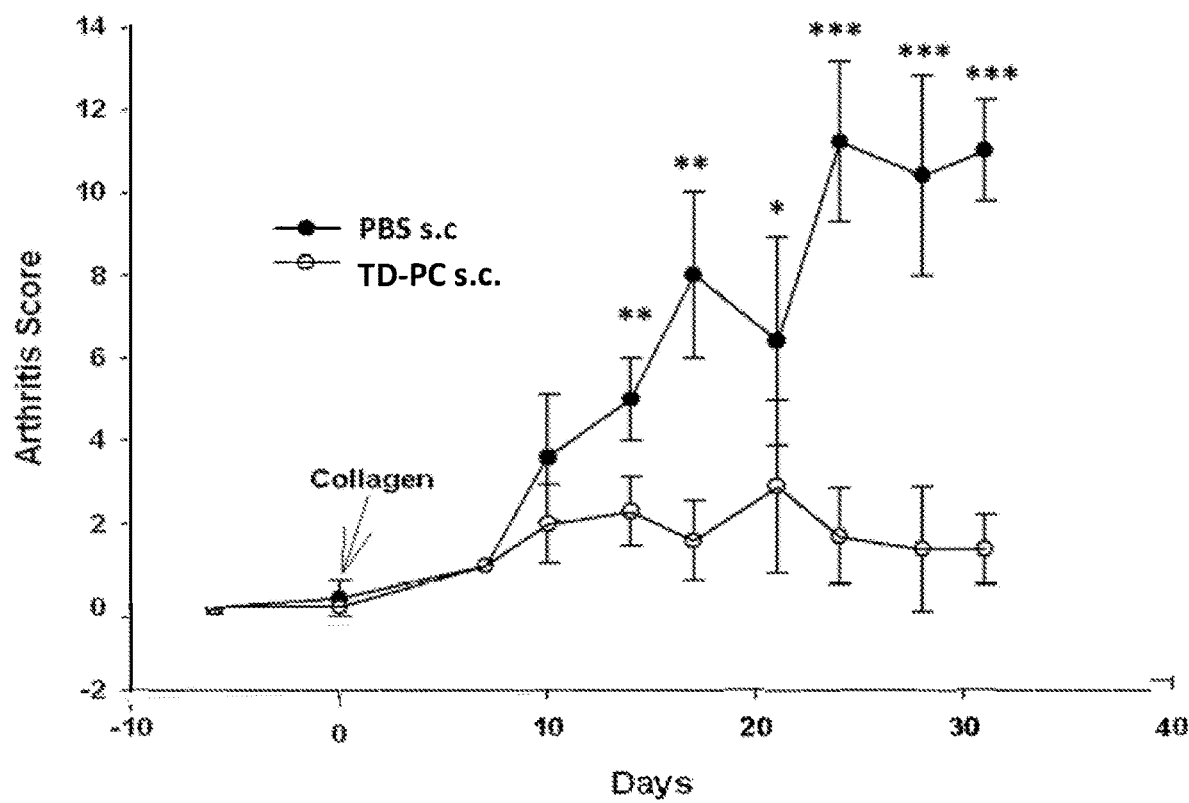
FIG. 26A shows the arthritis score in mice following subcutaneous (s.c.) treatment with TD-PC or vehicle (PBS). *$p<0.05$, $p<0.01$, *$p<0.001$.
Figure 26B:
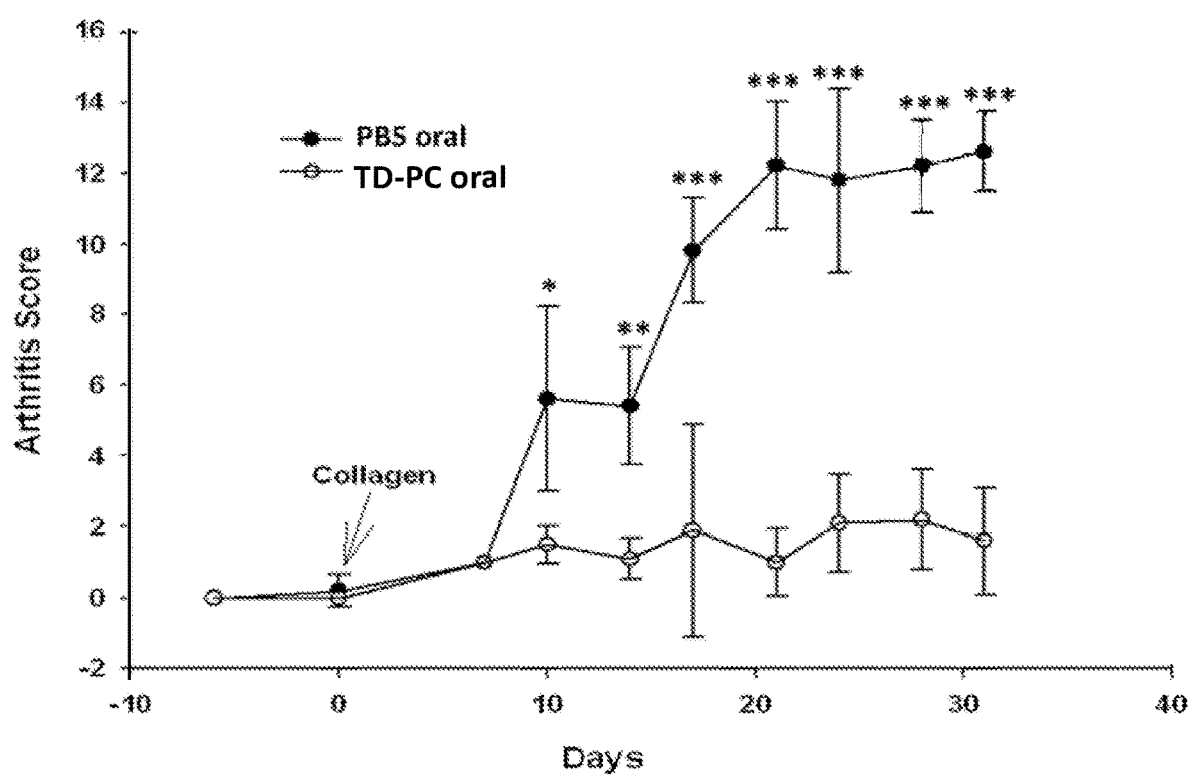
FIG. 26B shows the arthritis score in mice following treatment per os (oral) with TD-PC or vehicle (PBS). *$p<0.05$, $p<0.01$, *$p<0.001$.
Figure 26C:
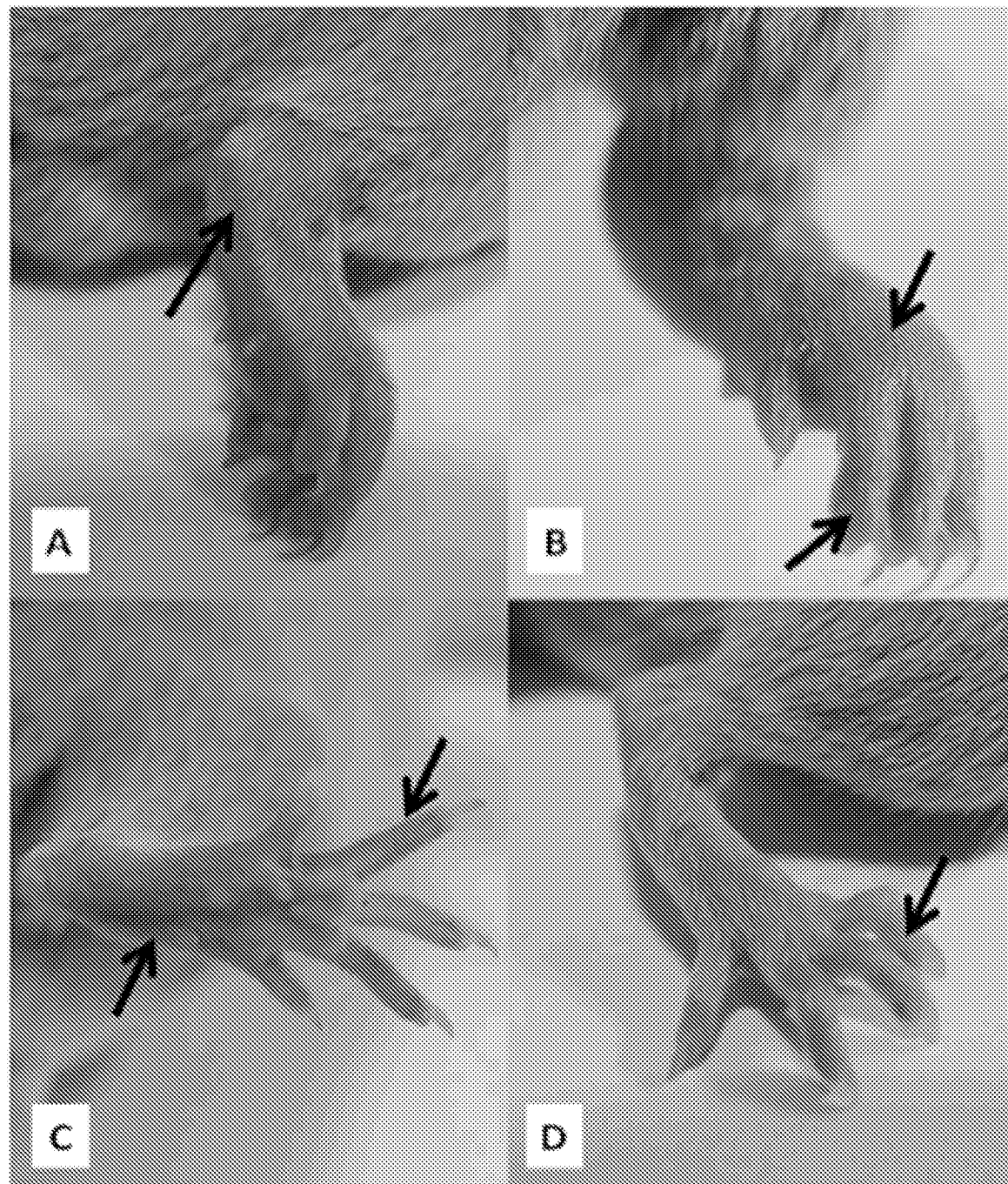
FIG. 26C are representative photos of joints of control mice treated with vehicle (PBS) per os (panel A) or subcutaneously (panel B), and of mice treated with TD-PC per os (panel C) or subcutaneously (panel D).

The main characteristic of rheumatoid arthritis is joint deformation due to high inflammation. The TD-PC effect on arthritis score in CIA mice was monitored. CIA mice were treated with TD-PC, orally or s.c. Control mice were treated with PBS orally or s.c. As detailed in FIGS. 26A and 26B, significantly lower arthritis score was observed in TD-PC treated mice compared to control mice (p<0.05). Arthritis score was lower in both groups of TD-PC treatment (oral and s.c.) starting two weeks after disease induction—day 14, until the mice were sacrificed—day 31. At day 31, TD-PC treated groups had a mean arthritis score of 1.5 (ranged from 0 to 4), while the control groups had mean arthritis score of 11.8 (ranged from 10 to 14; P<0.001). TD-PC s.c treated mice had a mean arthritis score of 1.410.84 whereas, PBS s.c treated mice had a mean arthritis score of 11±1.22 (p<0.001). Moreover, TD-PC oral treated mice had a mean arthritis score of 1.6±1.5 while, PBS oral treated mice had mean arthritis score of 12.6±1.14 (p<0.001). Representative pictures of mice joints are shown in FIG. 26C, demonstrating significant differences in inflammation between the TD-PC treated mice (lower panels C and D) in comparison to the control mice (upper panels A and B). Control mice developed edema and erythema at the ankle and towards the entire leg while TD-PC treated mice exhibited milder symptoms.

Example 14

TD-PC Effect on Titers of Anti-collagen Antibodies in Mice Sera

Figure 27:
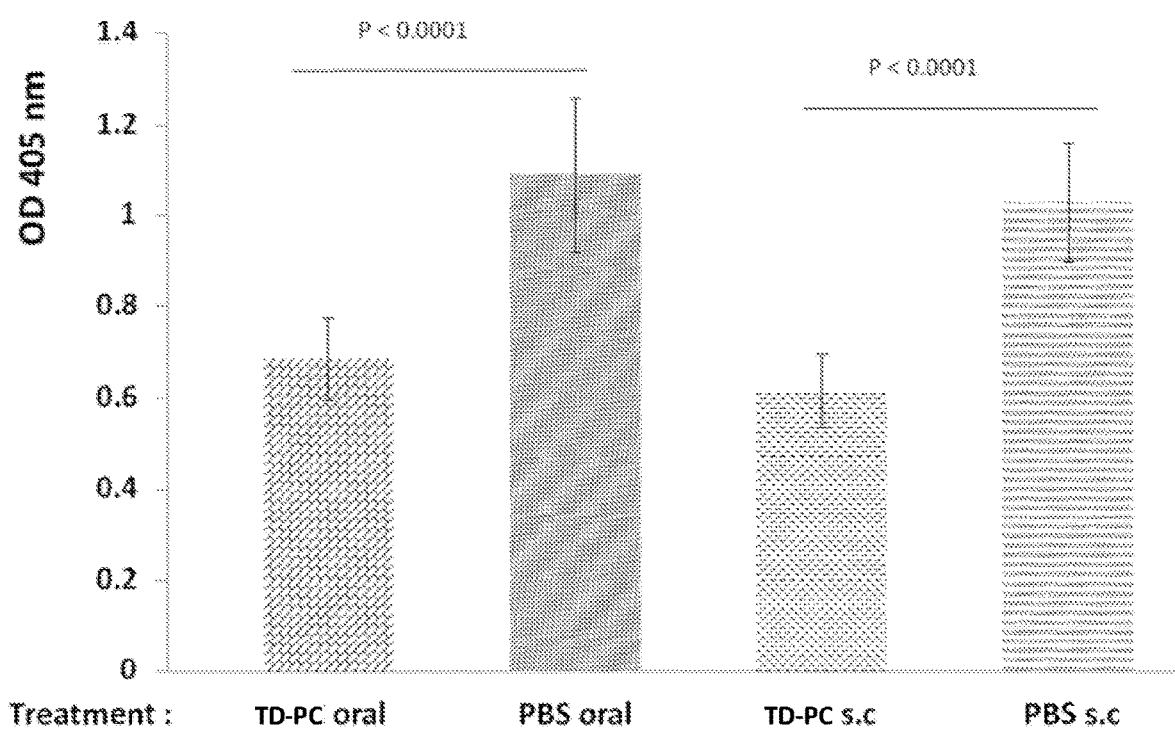
FIG. 27 shows the level of circulating anti-collagen antibodies in the sera of mice treated with TD-PC per os (oral), PBS per os (oral), TD-PC subcutaneously (s.c.) and PBS subcutaneously (s.c.).

Titers of anti-collagen type II antibodies in mice sera at a dilution of 1:200 (OD at 405nm) were measured at day 30 after disease induction while arthritis was fully manifested (FIG. 27). A statistically significant difference was documented between the TD-PC s.c and oral treated mice in comparison to PBS s.c and oral treated mice (p<0.001). The mean OD level of the anti-collagen type II antibodies in the mice treated with TD-PC per os was 0.685±0.09 while the corresponding mean OD level in control mice treated with PBS per os was 1.09±0.17. Furthermore, the mean OD level of the anti-collagen type II antibodies in mice treated with TD-PC s.c was 0.615±0.08, whereas the corresponding mean OD level mice treated with PBS s.c was 1.03±0.13 (p<0.001).

Example 15

TD-PC immunomodulation of cytokines expression

Figure 28A:
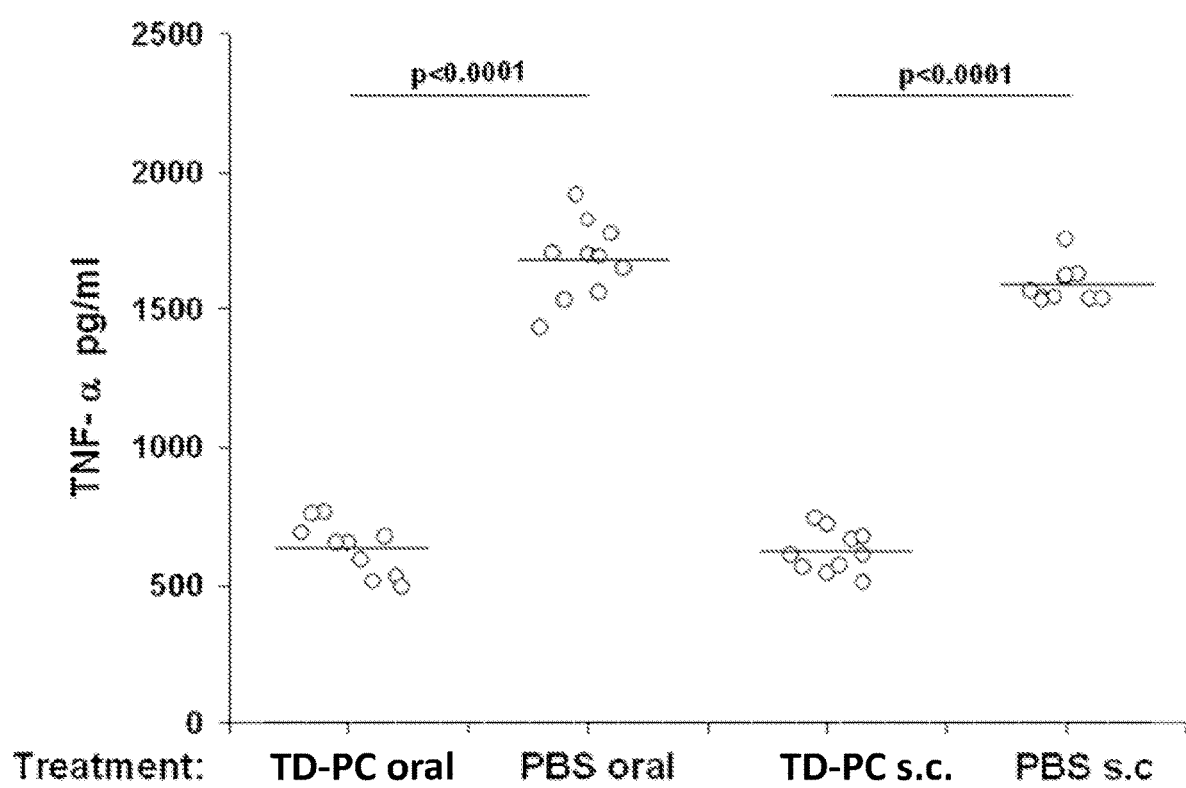
FIG. 28A shows the expression of the cytokine TNFα in the culture fluids of splenocytes originated from mice treated with TD-PC or PBS, orally or subcutaneously (s.c.).
Figure 28B:
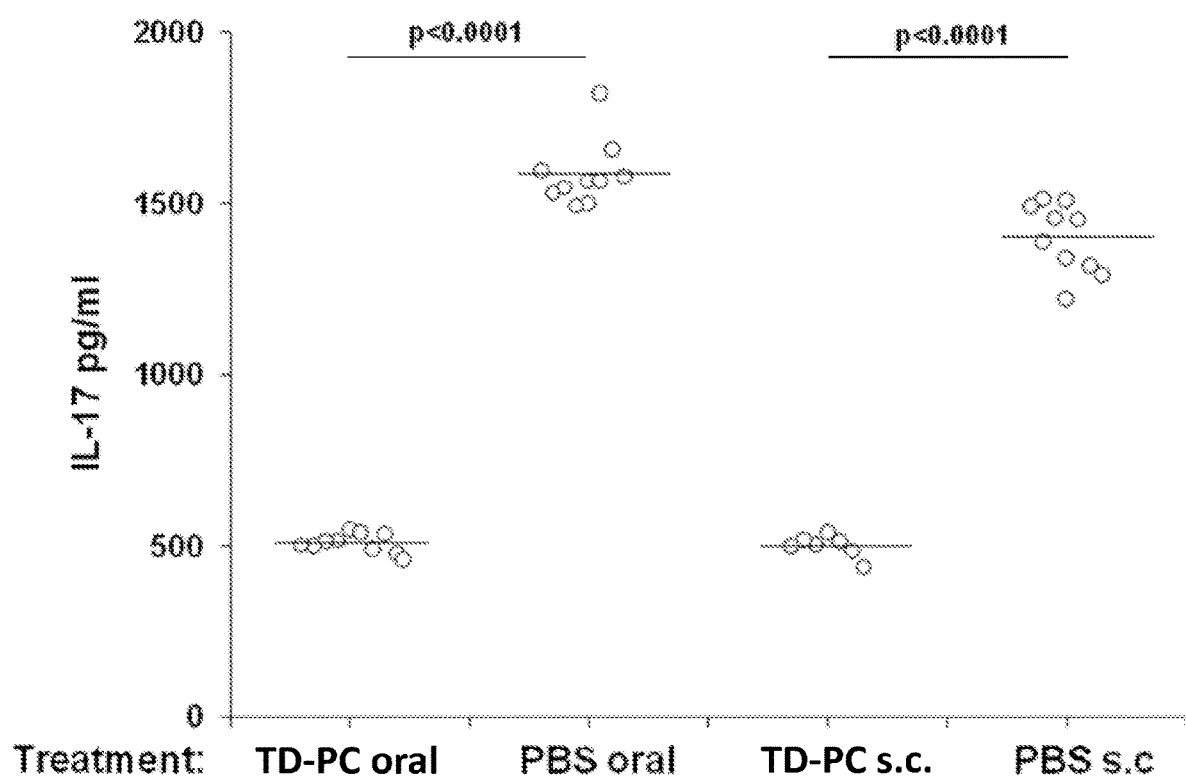
FIG. 28B shows the expression of the cytokine IL-17 in the culture fluids of splenocytes originated from mice treated with TD-PC or PBS, orally or subcutaneously (s.c.).
Figure 28C:
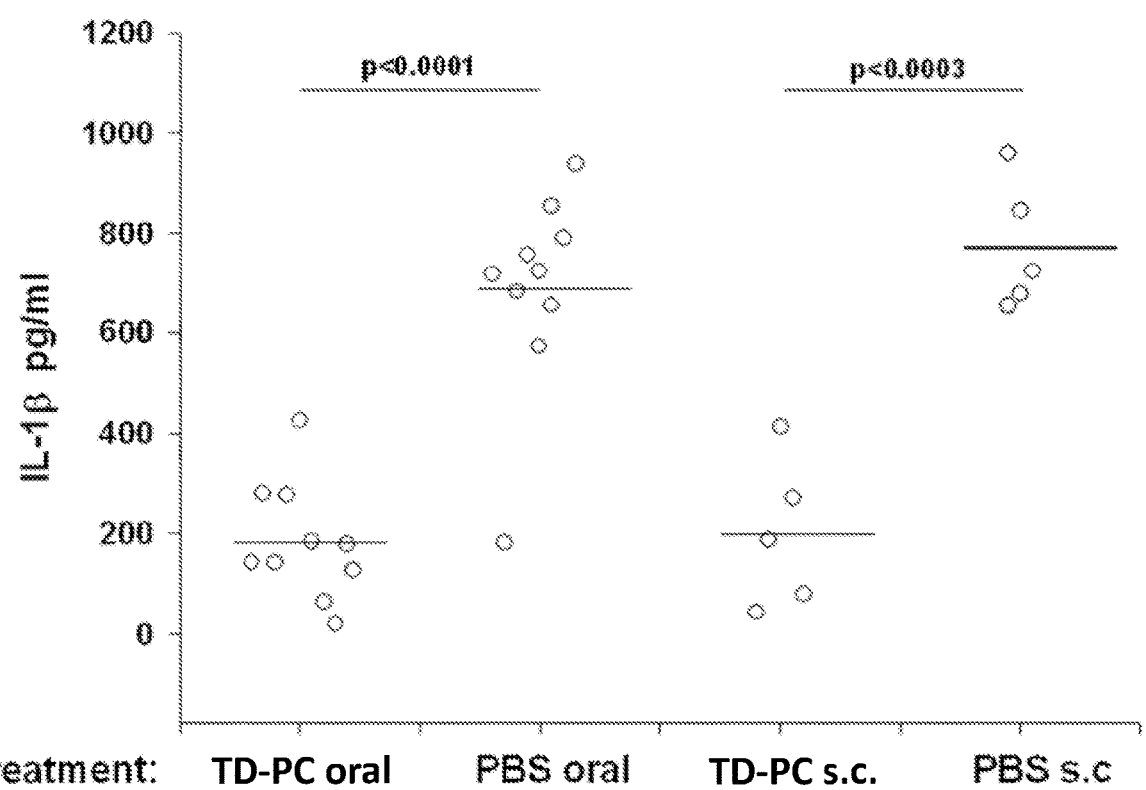
FIG. 28C shows the expression of the cytokine m-1β in the culture fluids of splenocytes originated from mice treated with TD-PC or PBS, orally or subcutaneously (s.c.).

Cytokines play a major role in synovial inflammation while the major ones are IL-17, TNFα and IL-1. Secretion of pro-inflammatory (TNFα, IL-β, IL-17) and anti-inflammatory cytokines (IL-10) by splenocytes derived from CIA mice treated with TD-PC or PBS (control), in-vitro, was evaluated. As depicted in FIGS. 28A-C and presented in Table 3, the level of pro-inflammatory cytokines in TD-PC treated mice (oral and s.c) was significantly lower compared to control mice (p<0.0001).

Figure 28D:
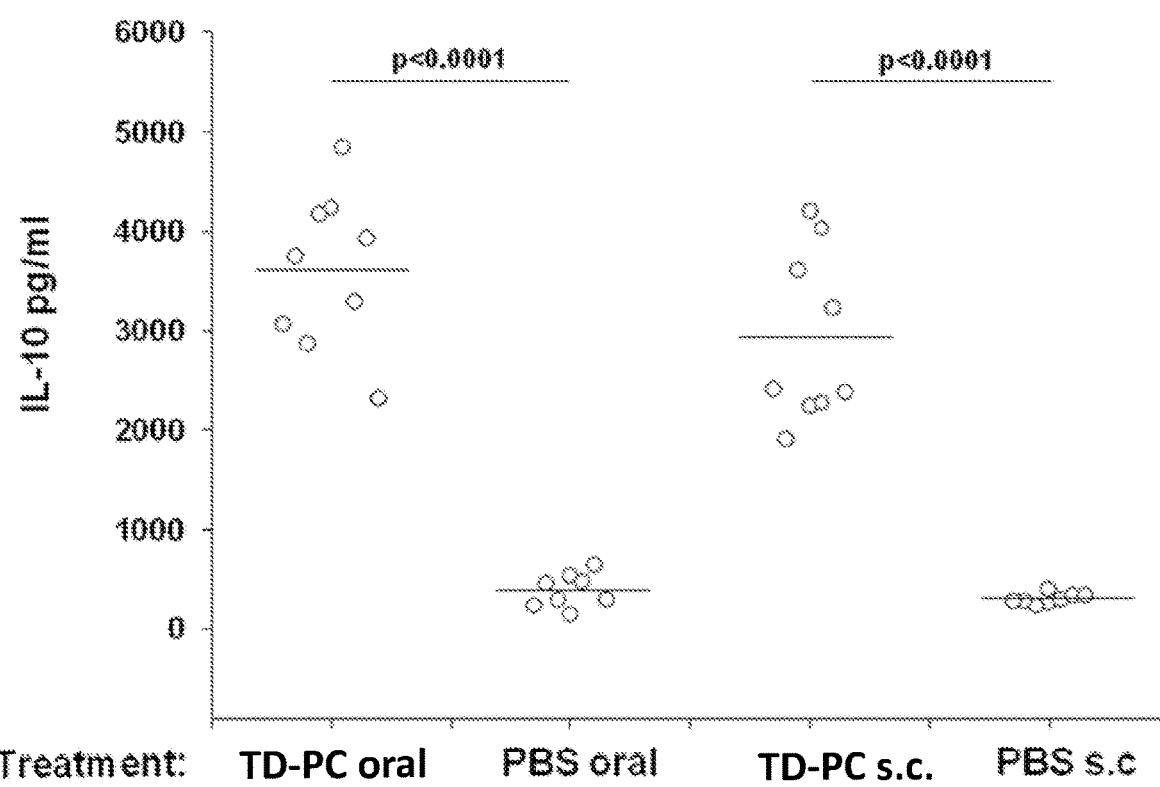
FIG. 28D shows the expression of the cytokine IL-10 in the culture fluids of splenocytes originated from mice treated with TD-PC or PBS, orally or subcutaneously (s.c.).

Furthermore, TD-PC increased the level of anti-inflammatory cytokine IL-10 in a significant manner compared to control mice (p<0.0001; FIG. 28D and Table 3).

TABLE 3

| Cytokine | TD-PC (pg/ml) | | PBS (pg/ml) | |
| --- | --- | --- | --- | --- |
| | oral | s.c. | oral | s.c. |
| TNFα | 633 | 621 | 1677 | 1586 |
| IL-17 | 505 | 497 | 1585 | 1395 |

TABLE 3-continued

| Cytokine | TD-PC (pg/ml) | | PBS (pg/ml) | |
| --- | --- | --- | --- | --- |
| | oral | s.c. | oral | s.c. |
| IL-1β | 183 | 198 | 686 | 770 |
| IL-10 | 3605 | 2917 | 384 | 302 |

Example 16

The Effect of TD-PC on the Expansion of Treg Cells

Figure 29A:
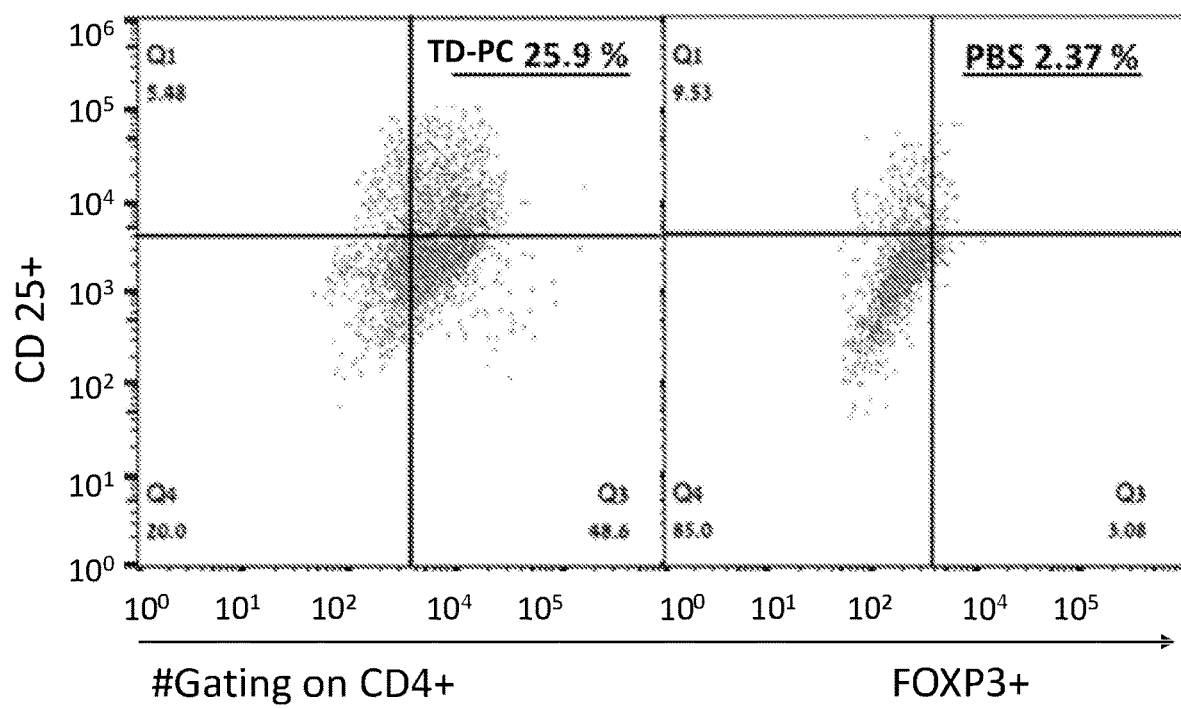
FIG. 29A shows representative FACS scans associated with Treg cells expansion in isolated splenocytes derived from mice treated with TD-PC or control (PBS) mice.
Figure 29B:
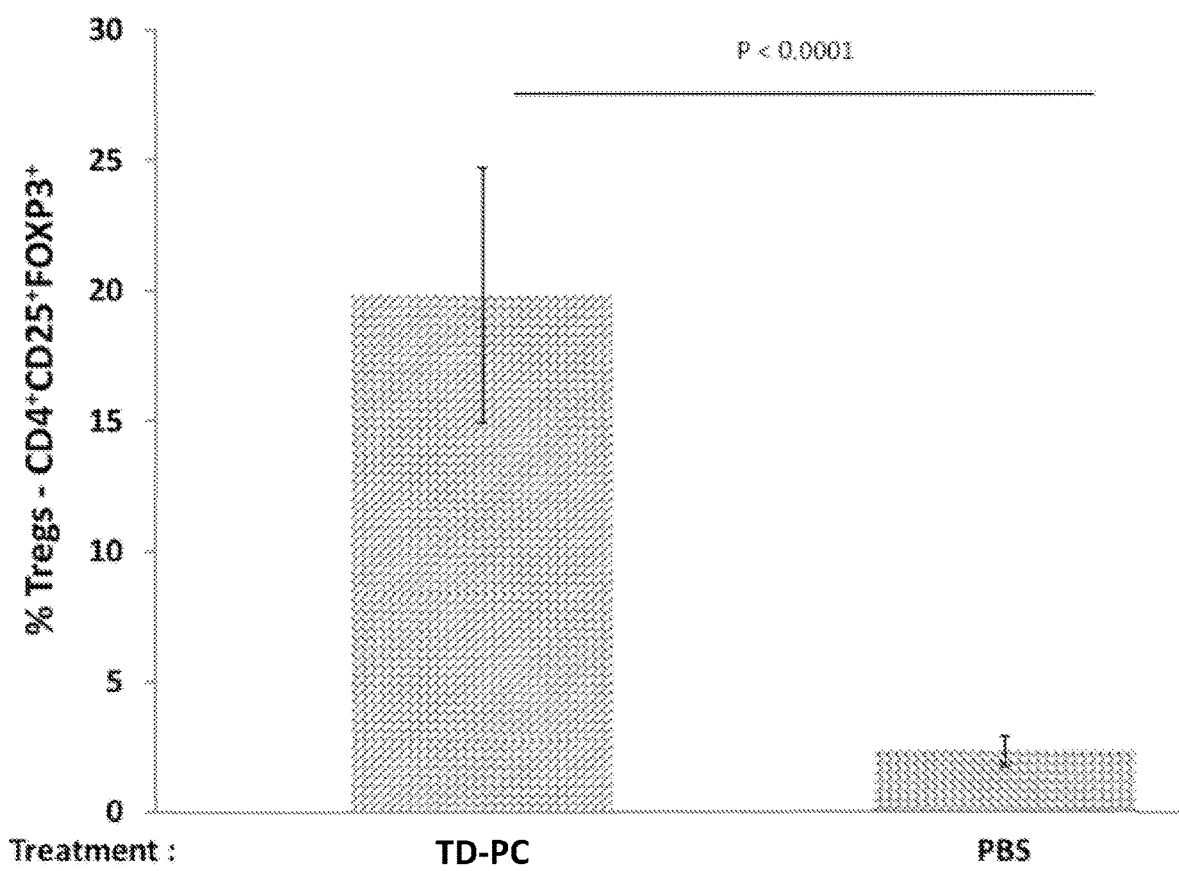
FIG. 29B shows quantitative analysis corresponding to the FACS scans represented in FIG. 29A.

The frequency of CD4+CD25+FOXP3+ Treg cells subset in isolated mice splenocytes, following treatment with TD-PC or control (PBS) is elucidated in FIGS. 29A-29B. A striking increase of Treg cells was observed in isolated splenocytes derived from TD-PC treated mice compared to control indicating that TD-PC treatment significantly promoted the Treg phenotype expansion (p<0.001). Representative data of the CD4+CD25+FOXP3+ levels in splenocytes derived from TD-PC and PBS treated mice gating on CD4+ T cells are presented in FIG. 29A and the corresponding statistics is presented in FIG. 29B.

Example 17

The Effect of TD-PC on Breg Cells Expansion in Splenocytes

Figure 30A:
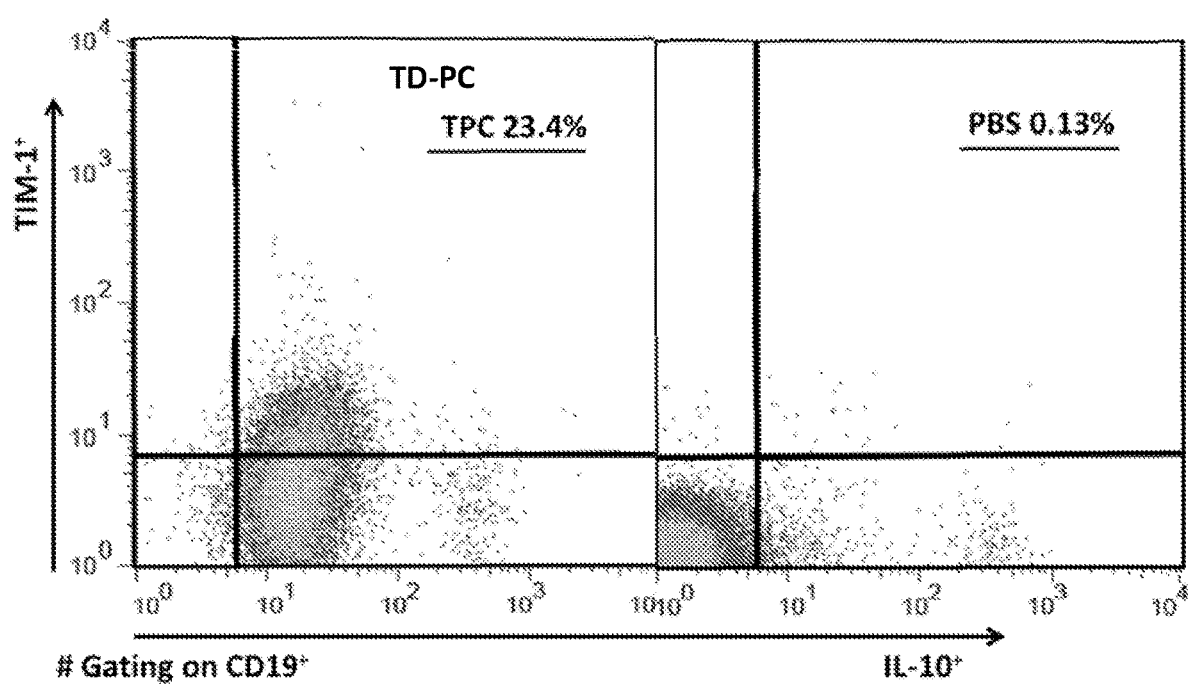
FIG. 30A and FIG. 30B show representative FACS scans associated with Breg cells expansion in isolated splenocytes derived from mice treated with TD-PC or control (PBS) mice.
Figure 30B:
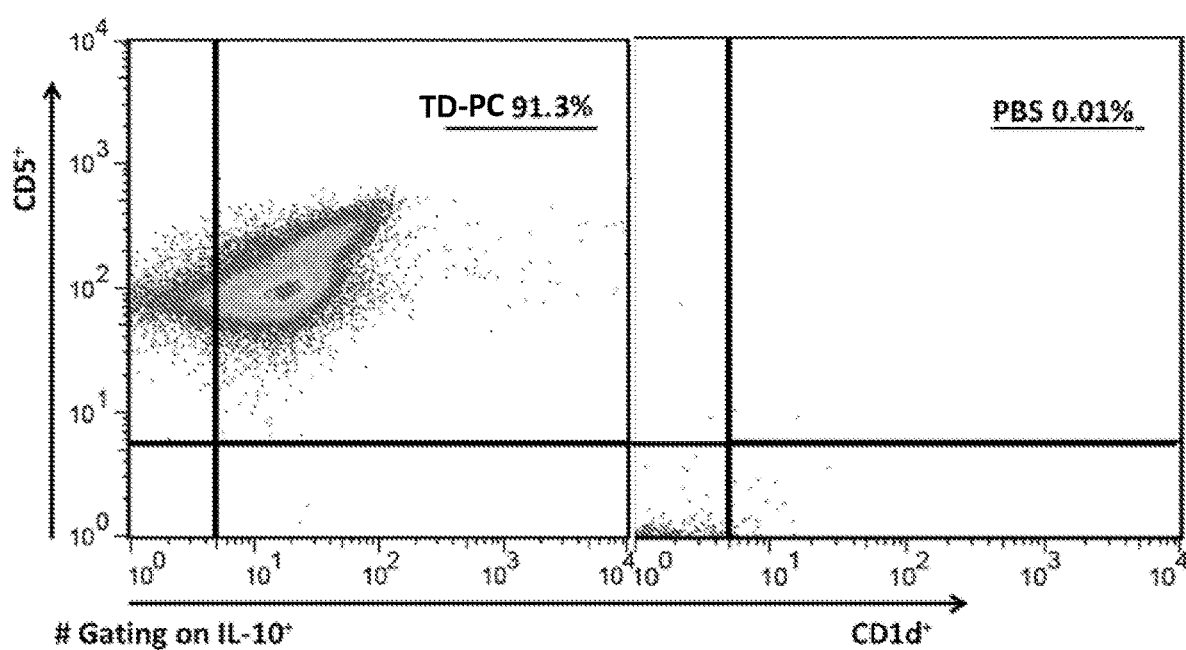
Figure 30C:
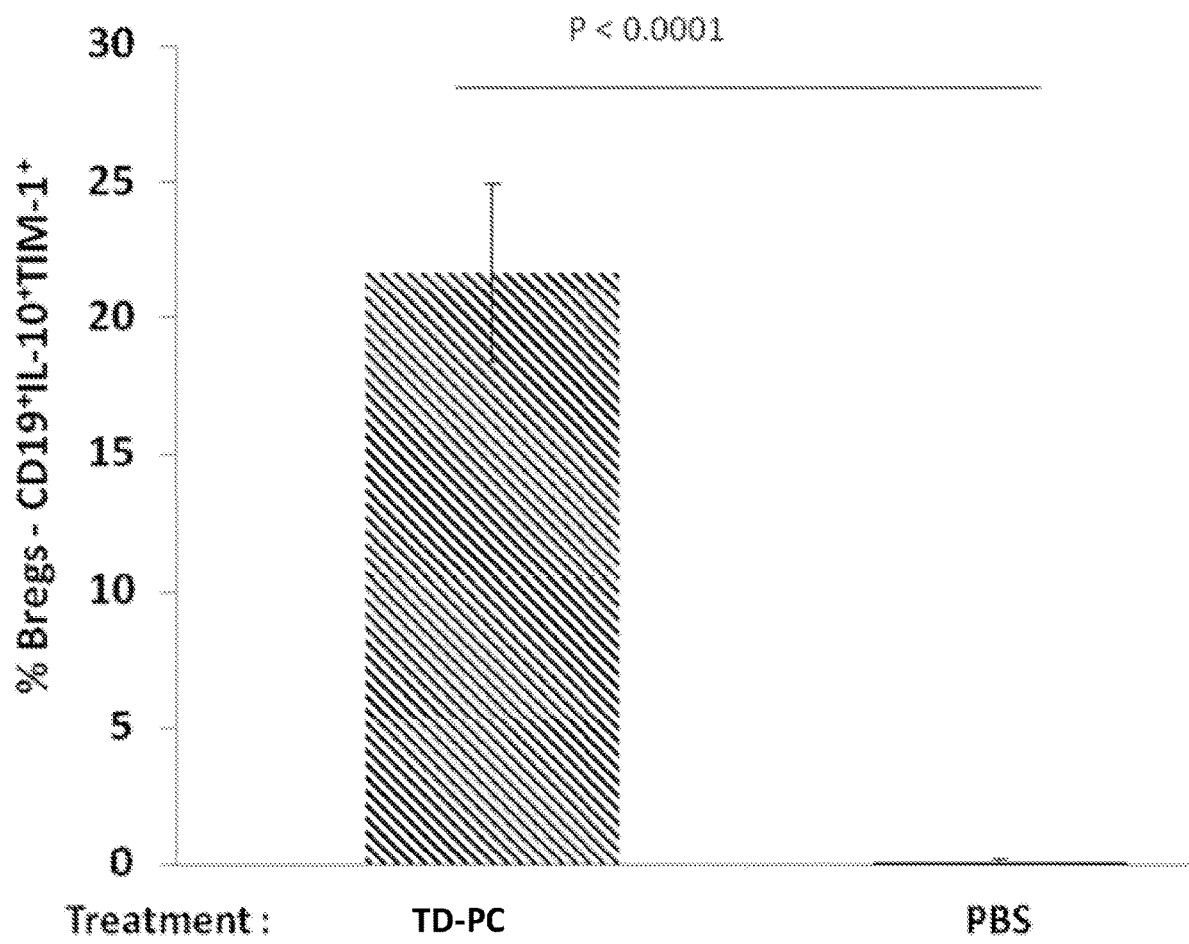
FIG. 30C and FIG. 30D show analyses corresponding to FIG. 30A and FIG. 30B, respectively.
Figure 30D:
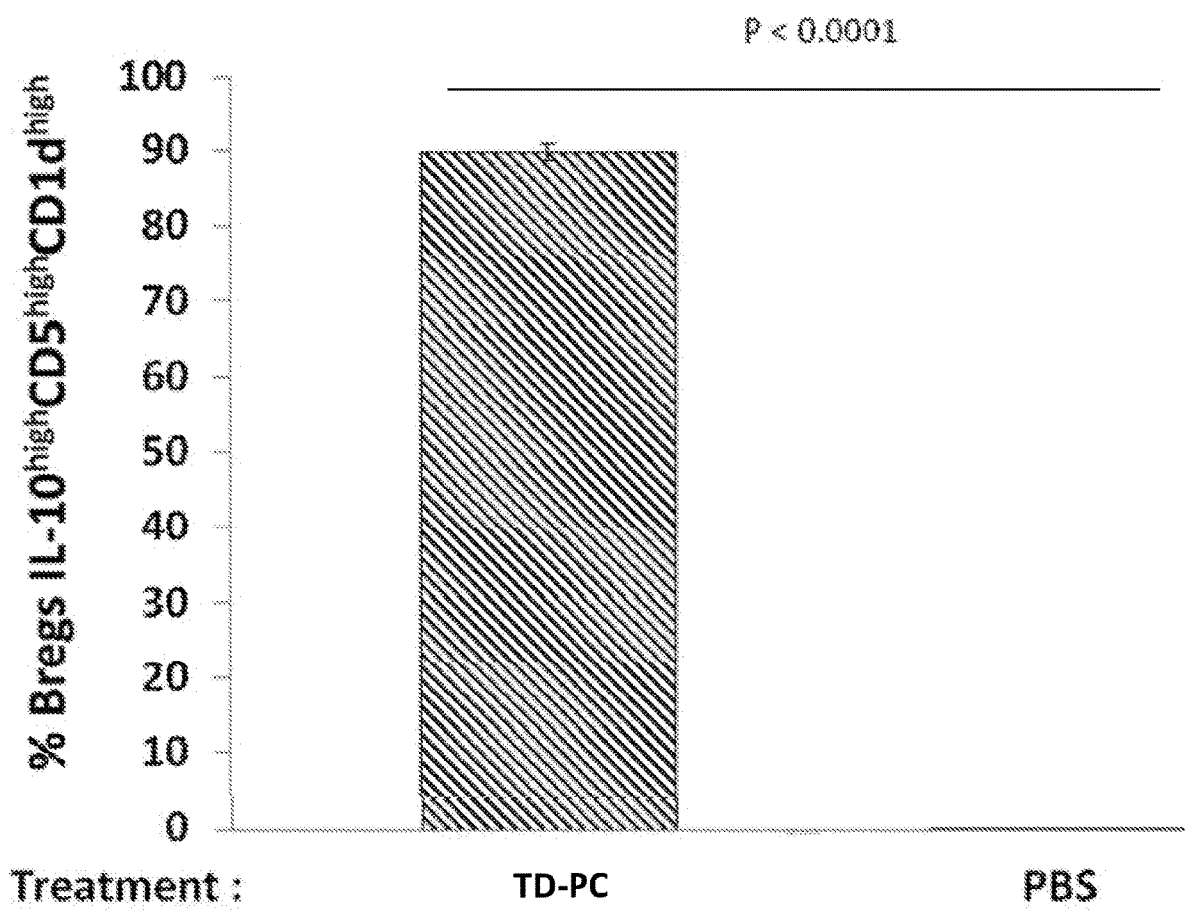

The mean percentage of Breg cells in isolated splenocytes following treatment with TD-PC or PBS was measured within two main subsets CD19+IL-10+ TIM-1+ (representative data: FIG. 30A, statistics: FIG. 30C, n=15) and IL-10$^{high}$CD5$^{high}$CD1d$^{high}$ (representative data: FIG. 30B, statistics: FIG. 30D, n=15). As depicted in FIGS. 30A-D, both subsets demonstrated that TD-PC significantly stimulated the Breg phenotype expansion in isolated mice splenocytes (p<0.0001) compared to control (PBS treated) mice.

Example 18

TD-PC Stopped Arthritis Progression in Mice with CIA

Figure 31A:
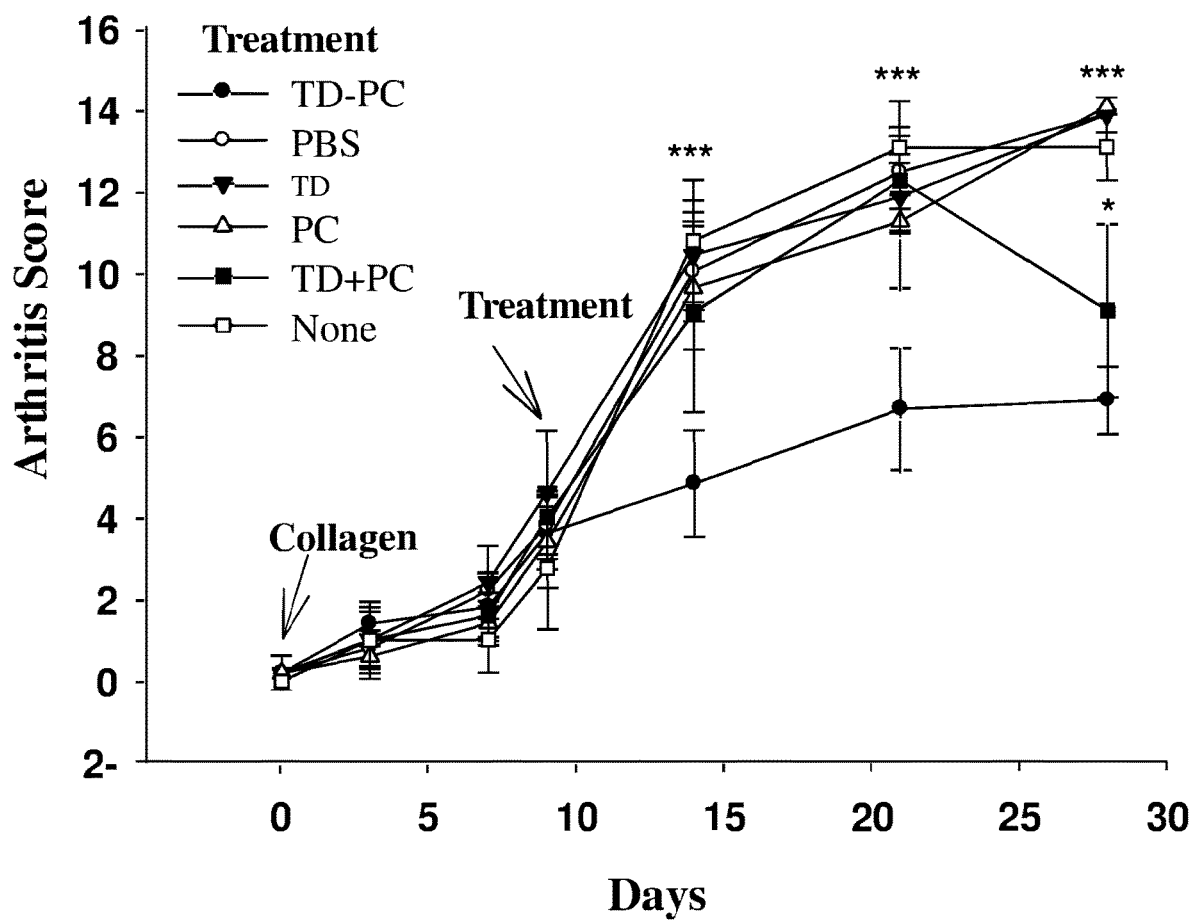
FIG. 31A shows arthritis score in DBA/1 CIA control untreated mice (PBS) or mice treated with TD-PC conjugate (TD-PC), the tuftsin derivative (TD), phosphorylcholine (PC) and the tuftsin derivative combined with phosphorylcholine (TD+PC).
Figure 31B:
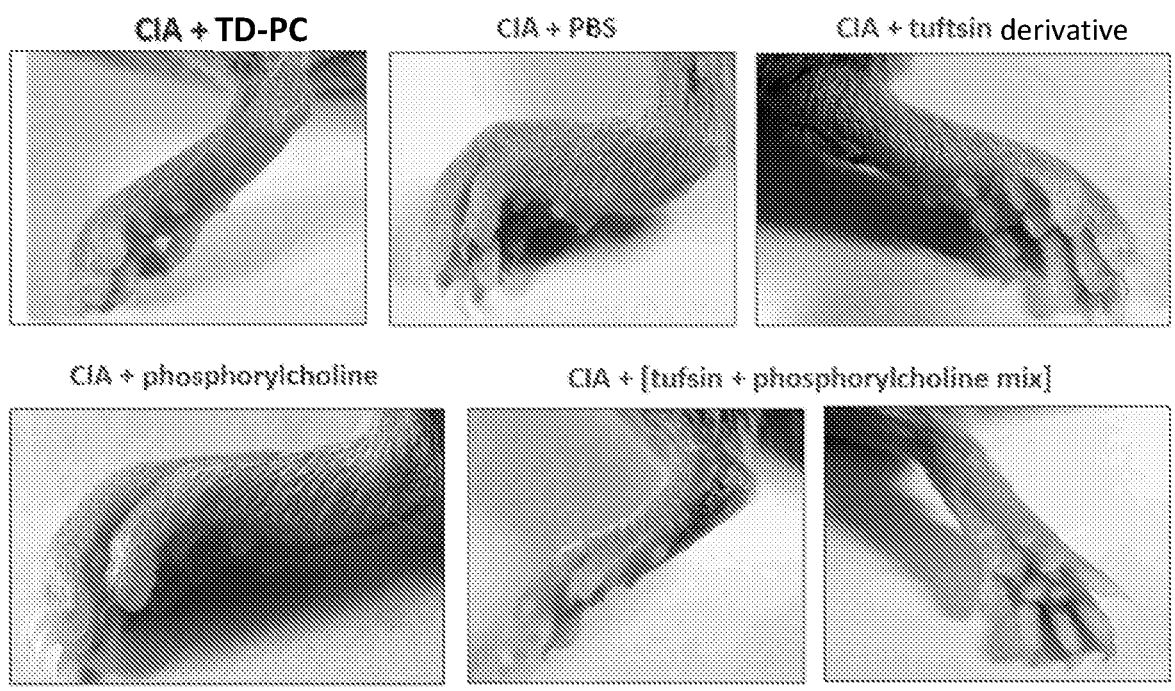
FIG. 31B are photos of representative joints of control CIA mice (PBS) and CIA mice treated with TD-PC (TD-PC), tuftsin, phosphorylcholine or a mix of the tuftsin derivative with phosphorylcholine (TD+PC).

Rheumatoid Arthritis is a progressive joint deformation disease caused by severe inflammation. CIA mice were subjected to subcutaneous injections of TD-PC, tuftsin derivative (SEQ ID NO: 25), PC, a mix of TD and PC, or PBS, 3 times a week. Untreated mice (None) did not receive any treatment. Treatment started as day 16 after disease induction when disease symptoms were already notable. As shown in FIG. 31A, at time 0 (treatment initiation) average arthritis score was relatively equal between all groups (TD-PC (SEQ ID NO: 25 conjugated to PC)—3.6±0.9; PBS—3.8±0.8; TD (SEQ ID NO: 25)—4.6±1.5; PC—3.4±1.1; TD+PC mix—4±0; None—2.75±1.5). A significant lower arthritis score was observed in TD-PC treated mice compared to mice treated with PBS, TD and PC and untreated mice (p<0.0001) or compared to TD+PC treated mice (p<0.05). The significant reduction in arthritis score was illustrious from day 7 after treatment administration and lasted until day 35 (the day mice were sacrificed). At day 35, the TD-PC treated mice had a mean arthritis score of 6.8±0.8 while control (PBS oral) mice had mean arthritis score of 13.8±0.45 (p<0.0001). Moreover, mice treated with the tuftsin derivative (SEQ ID NO: 25) had a mean arthritis score of 13.8±0.45, PC treated mice had a mean arthritis score of 14±0 and untreated mice had a mean arthritis score of 13±0.8 (p<0.0001). Furthermore, mice treated with a mix of TD+PC had a mean arthritis score of 9±2.2 (p<0.05). Representative pictures of mice joints are shown in FIG. 31B, demonstrating the less visible inflammation in the TD-PC treated mice in comparison with the PBS, TD, PC and TD+PC treated mice. TD-PC treated mice exhibited milder arthritis symptoms compared to other groups of mice.

Example 19

TD-PC Immunomodulation of Cytokines Expression

Figure 32A:
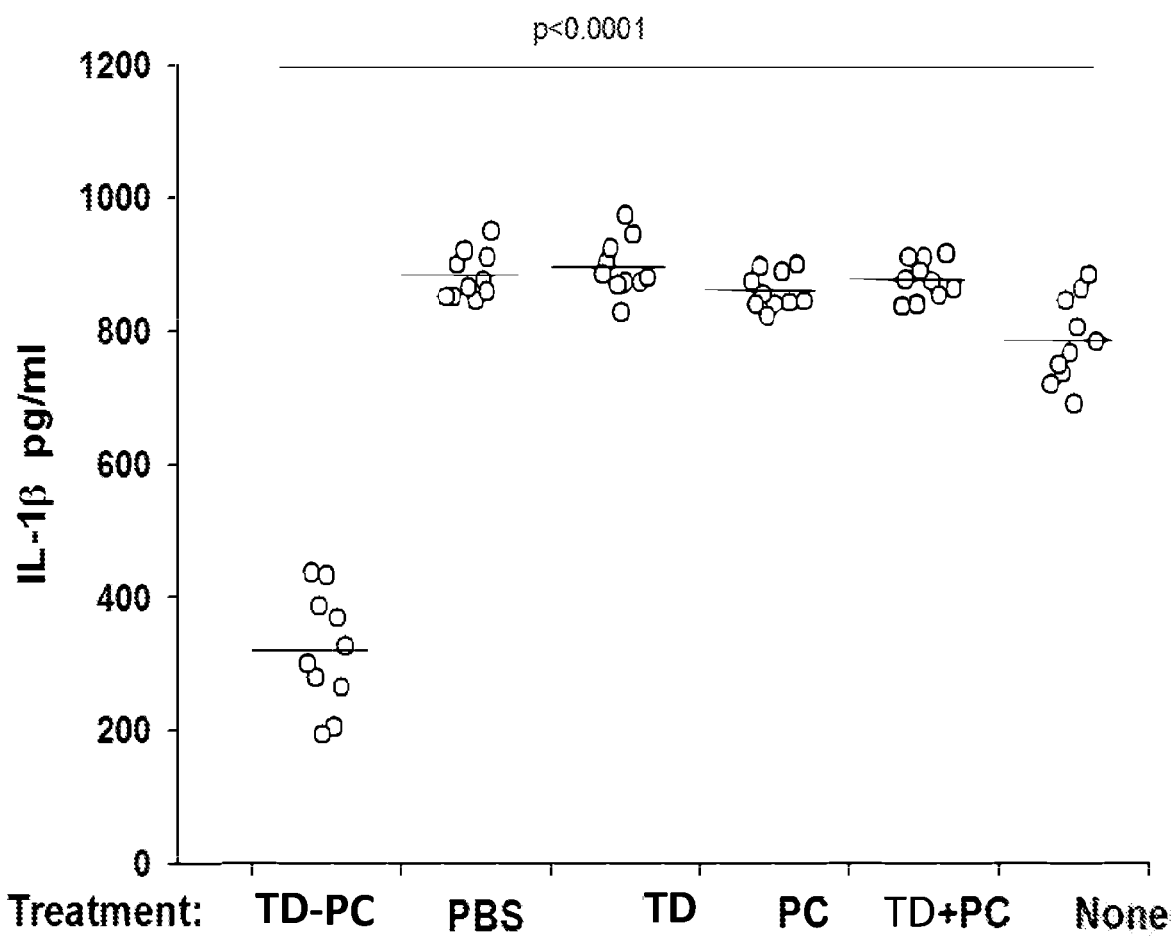
FIG. 32A, FIG. 32B, FIG. 32C, FIG. 32D and FIG. 32E show expression levels of the cytokines IL-1β; IL-17; IL-6; TNF-α; and IL-10, respectively, in the culture fluids of splenocytes originated from untreated mice, control mice (PBS) and mice treated with TD-PC, the tuftsin derivative (TD), phosphorylcholine (PC) or a mix of the tuftsin derivative with phosphorylcholine (TD+PC).
Figure 32B:
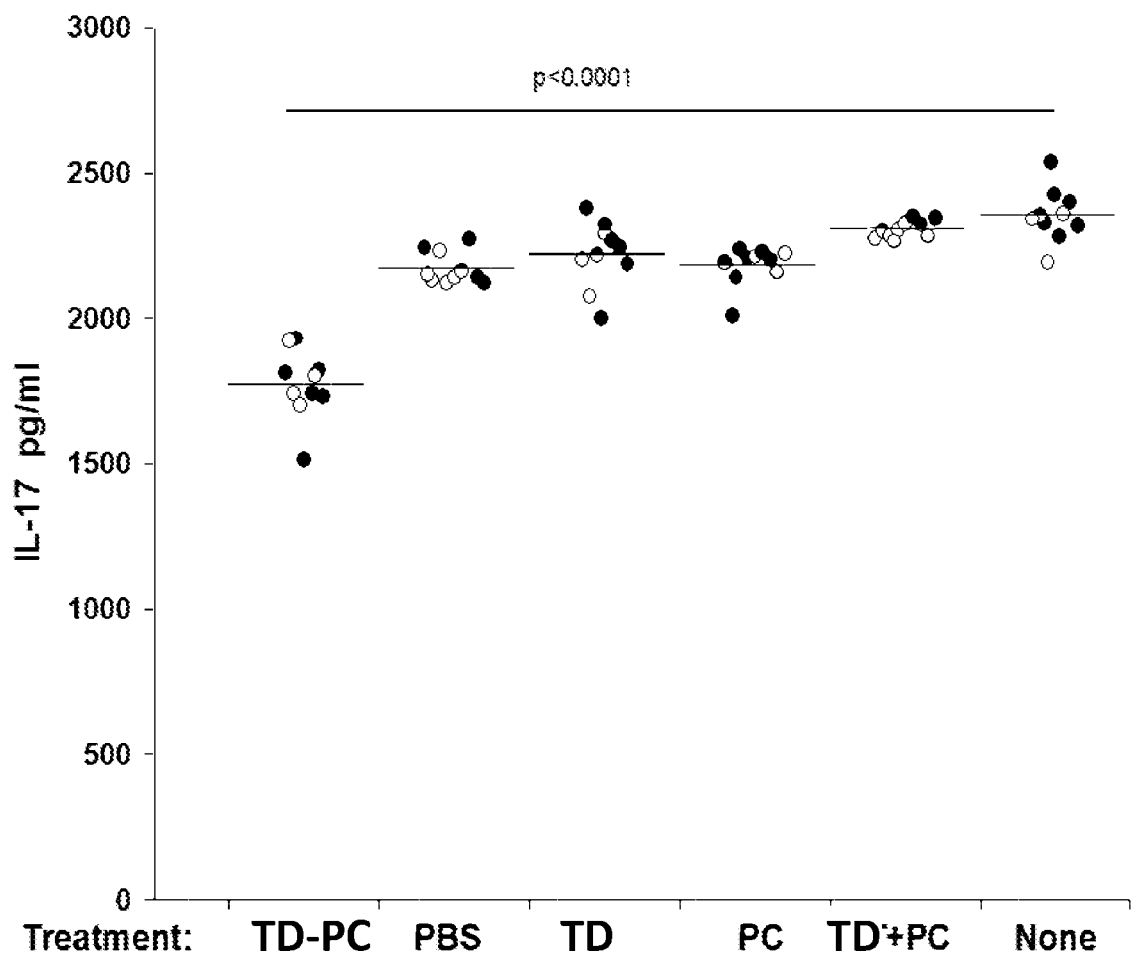
Figure 32C:
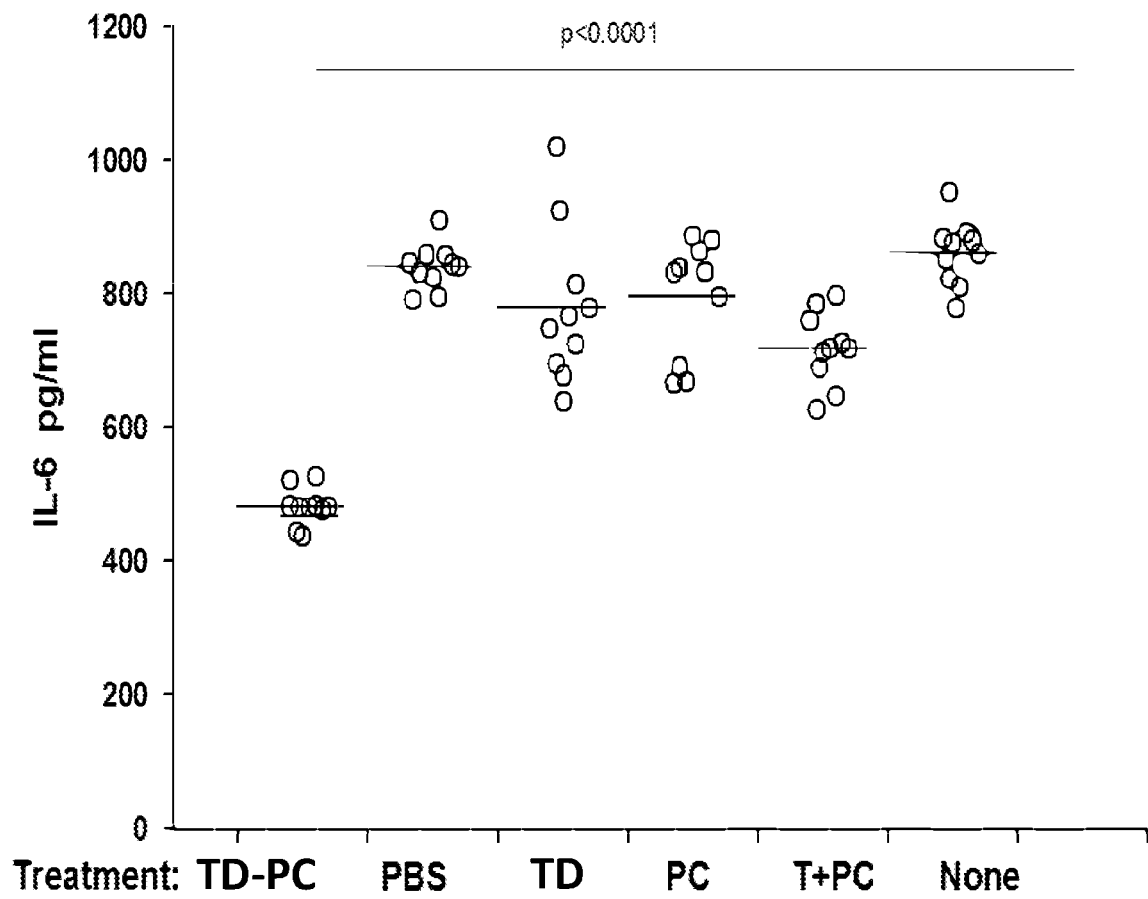
Figure 32D:
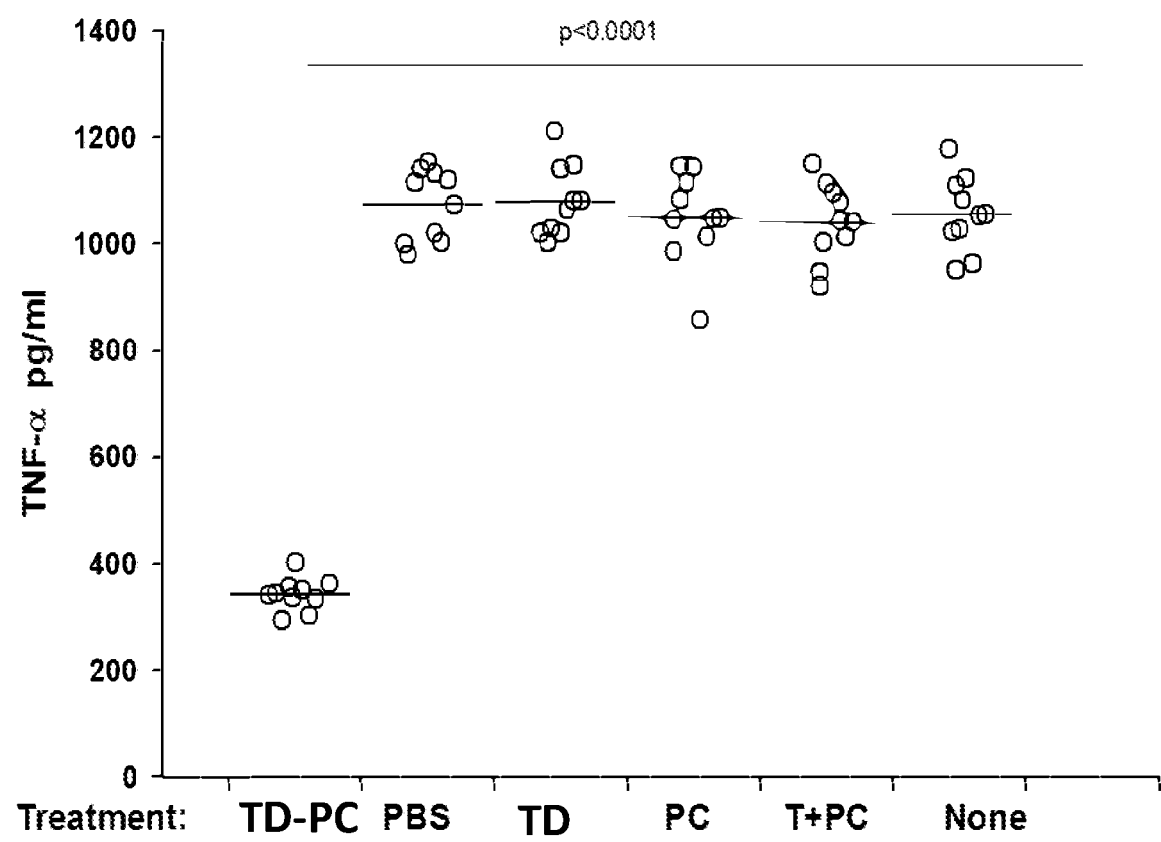
Figure 32E:
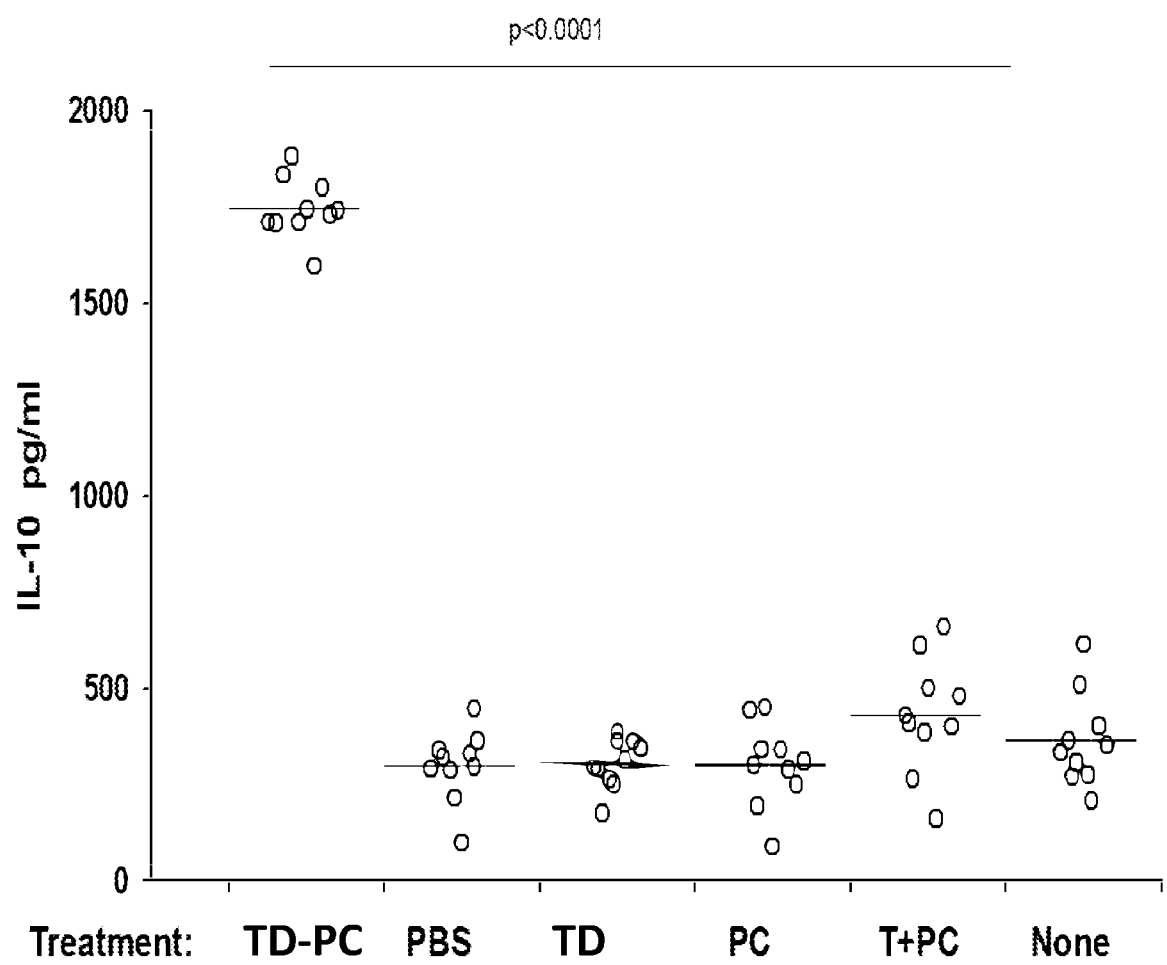

Secretion, in-vitro, of pro-inflammatory and anti-inflammatory cytokines by splenocytes derived from CIA mice treated with TD-PC, PBS, TD, PC, TD+PC or untreated mice was evaluated (FIGS. 32A-32D). The following cytokines secretions were examined: pro-inflammatory IL-1β (FIG. 32A), IL-17 (FIG. 32B), IL-6 (FIG. 32C), TNF-α (FIG. 32D) and anti-inflammatory IL-10 (FIG. 32E). The results indicate that TD-PC treatment inhibited the production of pro-inflammatory cytokines in comparison to controls (PBS, TD (SEQ ID NO: 25), PC and TD+PC treatments or no treatment; p<0.0001).

Mice treated with TD-PC had mean IL-1β level of 320 (pg/ml), mean IL-17 level of 1770 (pg/ml), mean IL-6 level of 480 (pg/ml) and mean TNF-α level of 342 (pg/ml). While, mice treated with PBS had mean IL-1β level of 883 (pg/ml), mean IL-17 level of 2170 (pg/ml), mean IL-6 level of 840 (pg/ml) and mean TNF-α level of 1073 (pg/ml). Moreover, TD (SEQ ID NO: 25) treated mice had mean IL-1β level of 896 (pg/ml), mean IL-17 level of 2217 (pg/ml), mean EL-6 level of 778 (pg/ml) and mean TNF-αlevel of 1079 (pg/ml). PC treated mice had mean IL-1β level of 860 (pg/ml), mean IL-17 level of 2179 (pg/ml), mean IL-6 level of 795 (pg/ml) and mean TNF-α level of 1048 (pg/ml). TD+PC treated mice had mean 1L-1β level of 877 (pg/ml), mean IL-17 level of 2304 (pg/ml), mean IL-6 level of 717 (pg/ml) and mean TNF-α level of 1039 (pg/ml). Untreated mice had mean IL-1β3 level of 785 (pg/ml), mean IL-17 level of 2352 (pg/ml), mean IL-6 level of 860 (pg/ml) and mean TNF-α level of 1055 (pg/ml).

TD-PC significantly increased the level of anti-inflammatory cytokine 1L-10 in comparison to control (PBS) mice (p<0.001; FIG. 32E).

Mice treated with TD-PC had mean IL-10 level of 1745 (pg/ml) where, mice treated with PBS had mean IL-10 level of 298 (pg/ml). Furthermore, TD treated mice had mean IL-10 level of 304 (pg/ml). PC treated mice had mean IL-10 level of 300 (pg/ml). TD+PC treated mice had mean IL-10 level of 429 (pg/ml) and untreated mice had mean IL-10 level of 363 (pg/ml).

Example 20

The Effect of TD-PC on Expansion of Treg Cells in Splenocytes

Figure 33A:
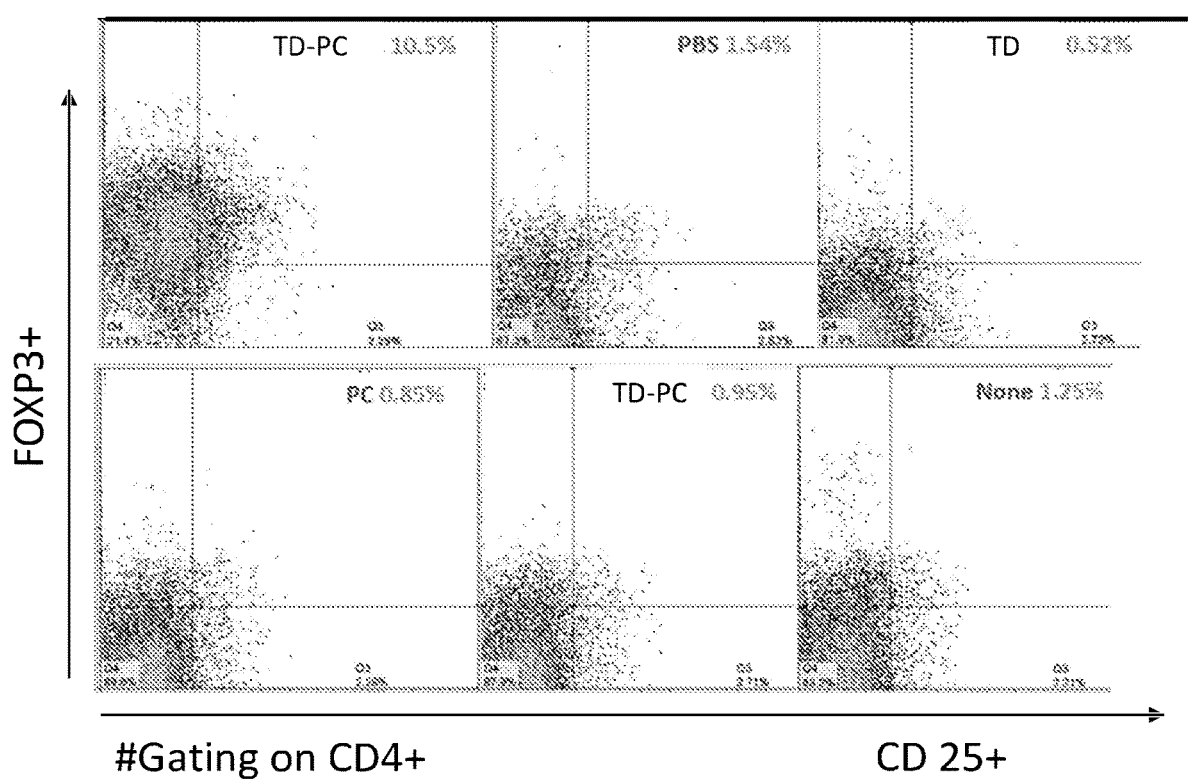
FIG. 33A shows representative FACS scans associated with Treg cells expansion in isolated splenocytes of derived from untreated mice (None), control mice (PBS) and mice treated with TD-PC (TD-PC), the tuftsin derivative (TD), phosphorylcholine (PC) and a mix of the tuftsin derivative with phosphorylcholine (TD+PC).
Figure 33B:
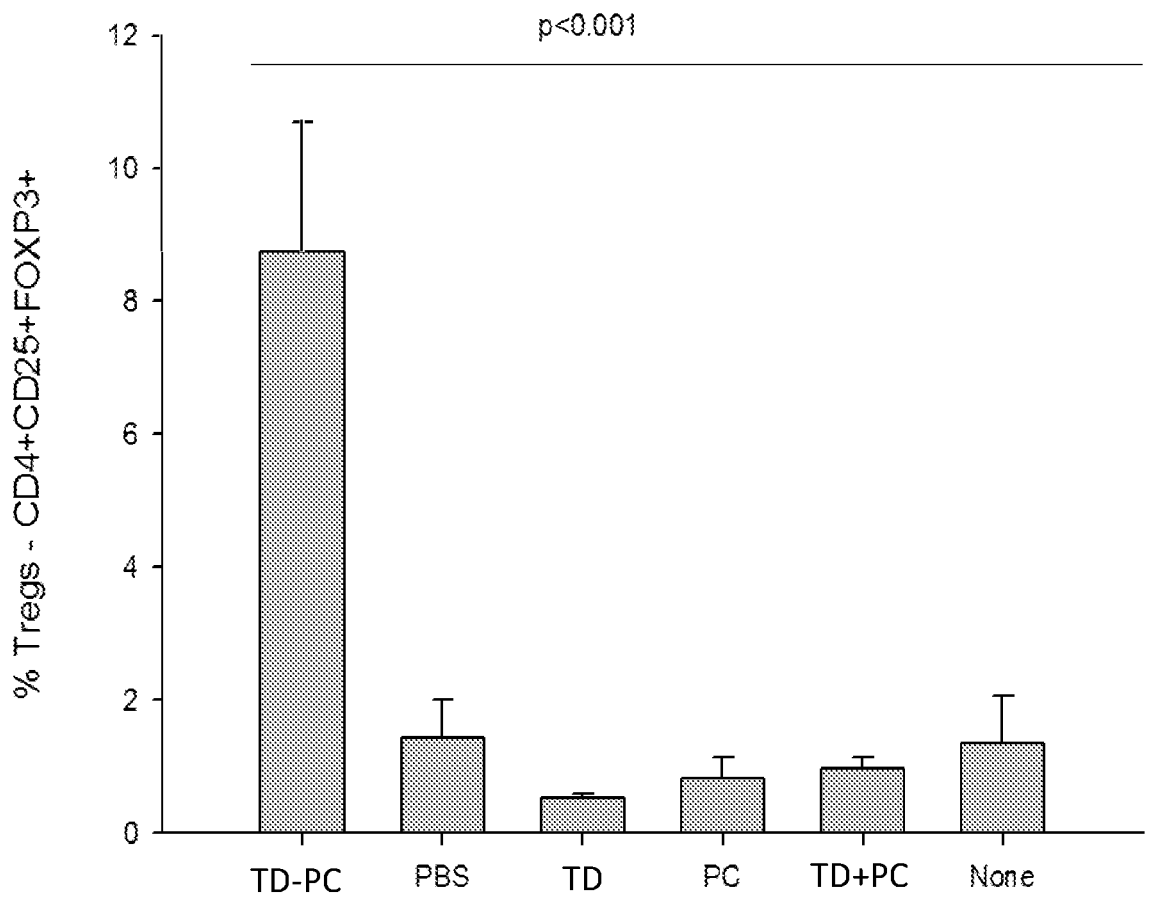
FIG. 33B shows an analysis corresponding to FIG. 33A.

The frequency of CD4+CD25+FOXP3+ Treg cells subset in isolated splenocytes from mice treated with TPC, PBS, TD (SEQ ID NO: 25), PC, TD+PC or untreated is elucidated in FIGS. 33A and 33B. A remarkable increase was observed in the mean percentage of the Treg cells measured in isolated splenocytes derived from TD-PC treated mice (8.75%) compared to the various controls (PBS, TD, PC and TD+PC treated mice and untreated mice −1.4%, 0.52%, 0.81%, 0.97% and 1.33%, respectfully). As illustrated in FIG. 33A, TD-PC treatment significantly promoted the Treg phenotype expansion (p<0.001) when compared with other treated groups of mice. Representative data of the CD4+CD25+ FOXP3+ levels in splenocytes derived from TD-PC, PBS, TD (SEQ ID NO: 25), PC and TD+PC treated mice and the untreated group, gating on CD4+ T cells are presented in FIG. 33B.

Example 21

The Effect of TD-PC on Expansion of Breg Cells in Splenocytes

Figure 34A:
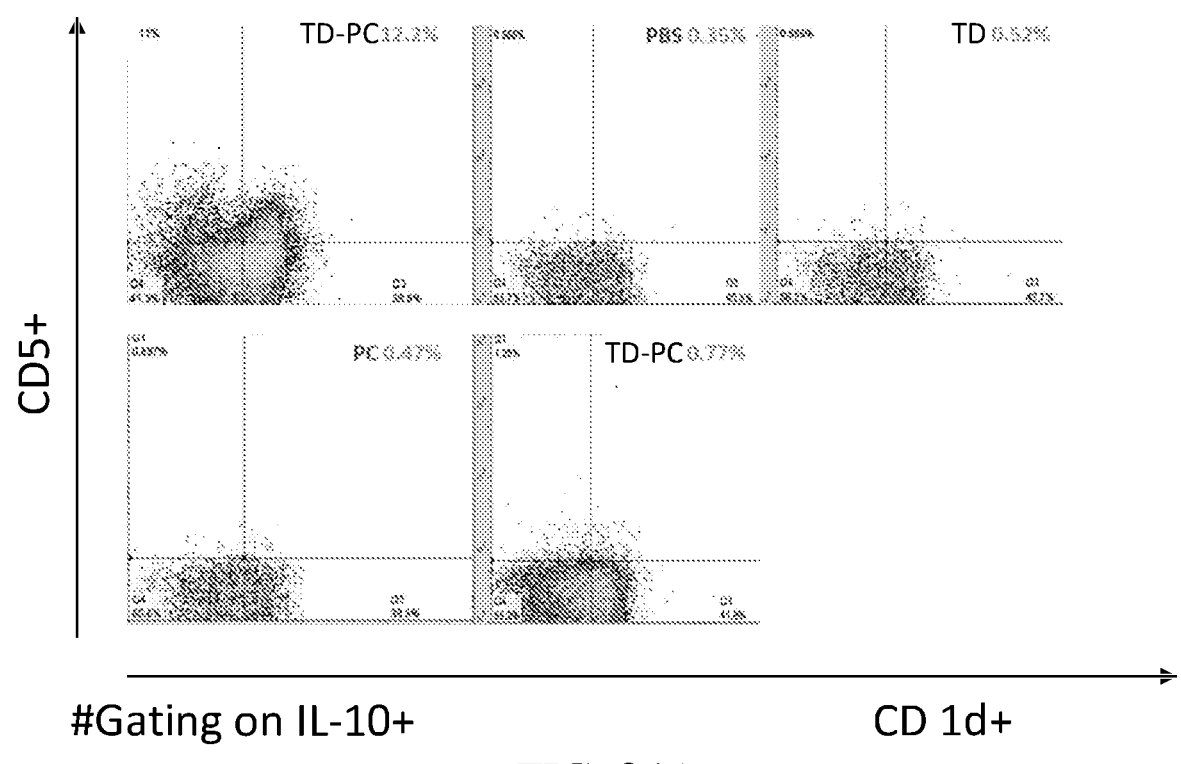
FIG. 34A shows representative FACS scans associated with Breg cells expansion in isolated splenocytes derived from control mice (PBS) or mice treated with TD-PC, the tuftsin derivative (TD), phosphorylcholine (PC) and a mix of the tuftsin derivative with phosphorylcholine (TD+PC).
Figure 34B:
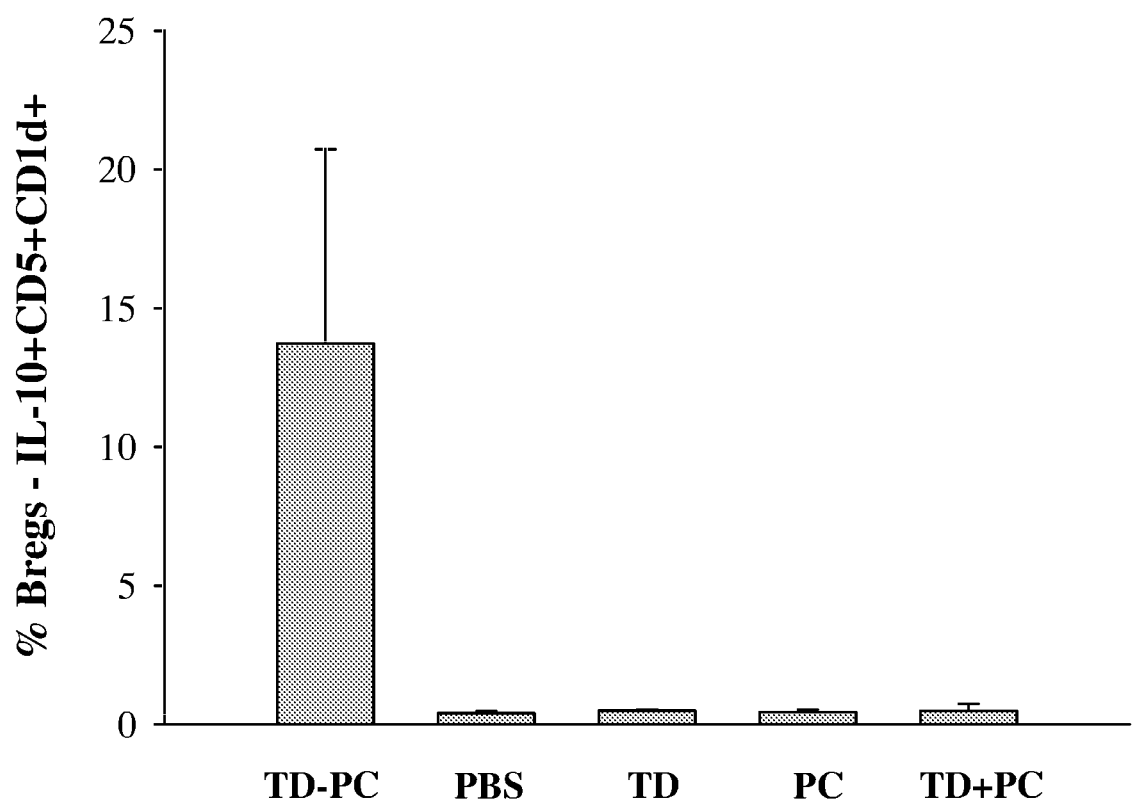
FIG. 34B shows quantitative analysis corresponding to FIG. 34A.

The mean percentage of Breg cells in isolated splenocytes following treatment with TD-PC, PBS, TD (SEQ ID NO: 25), PC, TD+PC and None was measured within IL-10+ CD25+CD1d+ subset. As depicted in FIG. 34A-34B, TD-PC significantly stimulated the Breg phenotype expansion in isolated mice splenocytes (p<0.001) with respect to PBS, TD, PC, TD+PC and treated groups of mice. As demonstrated in FIG. 34B, the mean percentage of IL-10+CD25+ CD1d+ Breg cells of TD-PC treated mice was higher 13.73% while PBS, TD (SEQ ID NO: 25), PC and TD+PC treated groups had mean percentage of 0.4%, 0,5%, 0.44% and 0,48% respectfully. Representative data of IL-10+ CD25+CD1d+ levels in splenocytes derived from TD-PC, PBS, TD (SEQ ID NO: 25), PC and TD+PC treated mice gating on IL-10+B cells, are presented in FIG. 34A.

Example 22

TD-PC Induces Macrophages to Secret Anti-inflammatory Cytokines

The relative expression of the anti-inflammatory cytokine IL-10 was analyzed in human macrophages treated with TD-PC (TD-PC), and PC-Ovalbumin (OVA-PC). Specifically, THP-1 cells (a monocytic cell line established from human monocytic leukemia) were induced to differentiation into adherent macrophage-like phenotype (M0) by culturing the cells ($10^5$ cells/ml) in the presence of phorbol 12-myristate 13-acetate (PMA; 80 nM) and VD3 (100 nM). For inducing differentiation from M0 to M1 (M1 polarized macrophages) the cells were further incubated with LPS (1 µg/ml), IFNγ (20 ng/ml). For shifting from M1 to M2 macrophages (M2 polarized macrophages) the cells were washed and further incubated with IL-4 (10 ng/ml) and IL-13 (10 ng/ml) for 72 hours.

Figure 35:
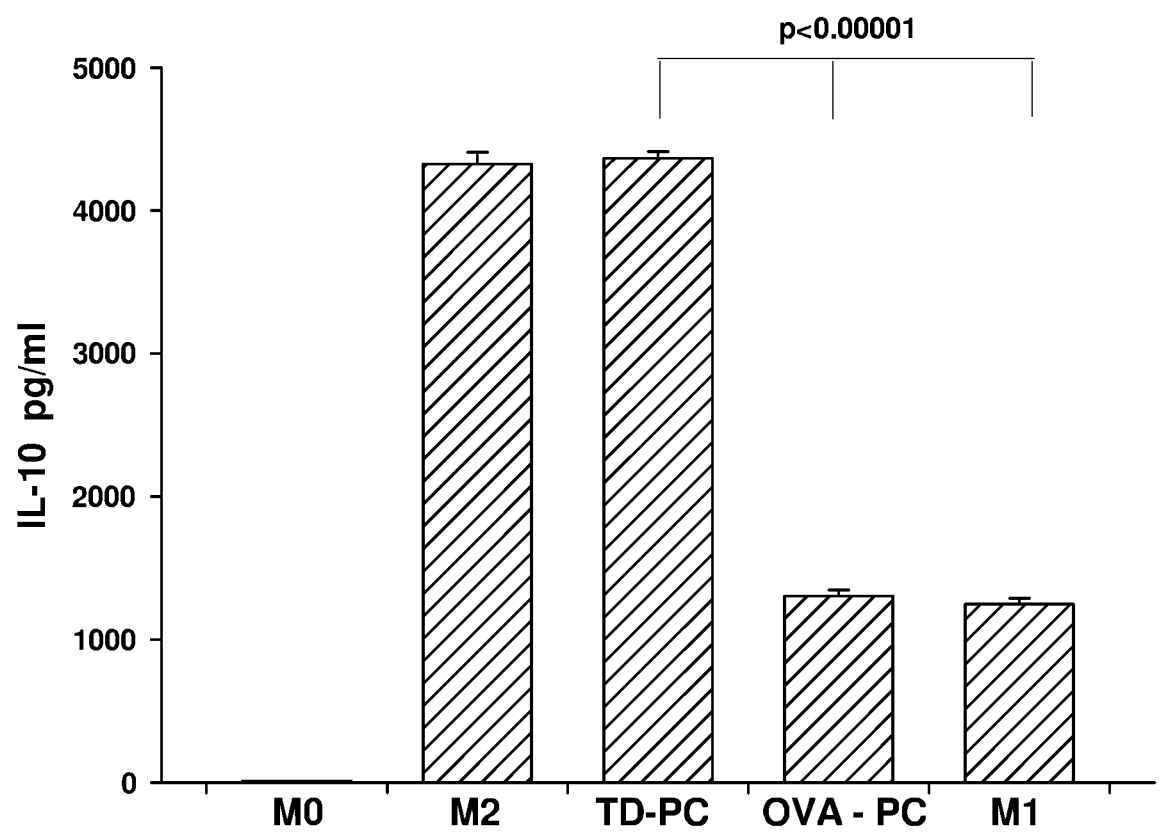
FIG. 35 shows relative secretion levels of anti-inflammatory IL-10 cytokine from macrophages treated with TD-PC relative to PC-Ovalbumin (OVA-PC; $p<0.00001$).

In order to determine whether TD-PC, TD, PC or PC-OVA can induce a shift form M1 cells to M2 macrophages secreting anti-inflammatory cytokine IL-10, M1 polarized macrophages were incubated with each molecule or conjugate at 5 µg/ml for 72 hrs. As shown in FIG. 35, TD-PC induce a significant shift of M1 macrophages to M2 macrophage in comparison to OVA-PC (p<0.00001). The results suggest that TD-PC is advantageous over OVA-PC in inducing a shift from pro-inflammatory macrophages to macrophages secreting anti-inflammatory cytokine IL-10.

Example 23

TD-PC Shifts the Microbiome Profile

Figure 36A:
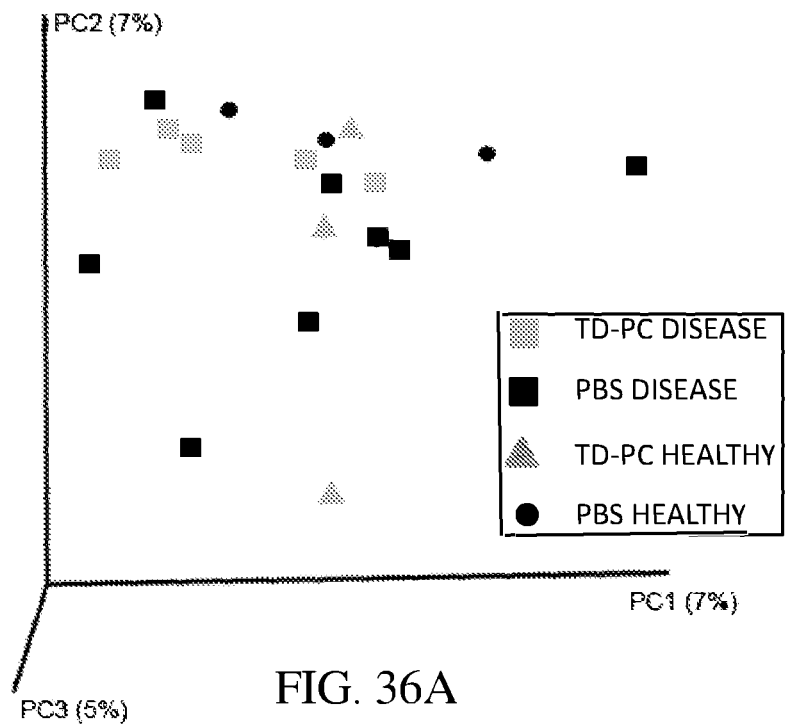
FIG. 36A is a Principal Coordinate Analysis (PCA) representing bacteria population in fecal samples of healthy mice or CIA mice prior to CIA induction (day 0) and prior to treatment with TD-PC set forth in SEQ ID NO: 25 (gray square, gray triangle) or with a carrier (PBS; black square, black circle).

The effect of TD-PC on the microbiome of mice with collagen induced arthritis (CIA) was monitored. A comparison of the microbiome population between day 0 (before disease induction) and day 35 - when the disease is established and the mice are inflamed was performed using Principal Coordinate Analyses (PCA) plot (FIGS. 36A-36B), which represent the diversity of the different bacteria populations within the fecal samples of each treatment: (group 1) s.c. injection of the TD-PC set forth in SEQ ID NO: 25 to healthy mice (gray triangle); (group 2) s.c. injection of the TD-PC set forth in SEQ ID NO: 25 to CIA mice (gray square); (group 3) s.c. injection of PBS to healthy mice (black circle); and (group 4) s.c. injection of PBS to CIA mice (black square). PC1 and PC2 and PC3 along the x and y and z axes, respectively, depict the amount of variance (the spread of the data values) in the samples explained by these components, included in brackets. The number of principle components (axes) is less than or equal to the number of individual measurements included for each sample, with each axis describing a fraction of the sample variance. As shown in FIG. 36A, a variety of bacteria is randomly distributed at day 0. However, following treatment with the conjugate TD-PC, the microbiome profile associated with untreated mice bearing the disease (group 2) is significantly distinct from the corresponding microbiome profiles in the remaining groups (groups 1, 3 and 4).

Figure 36B:
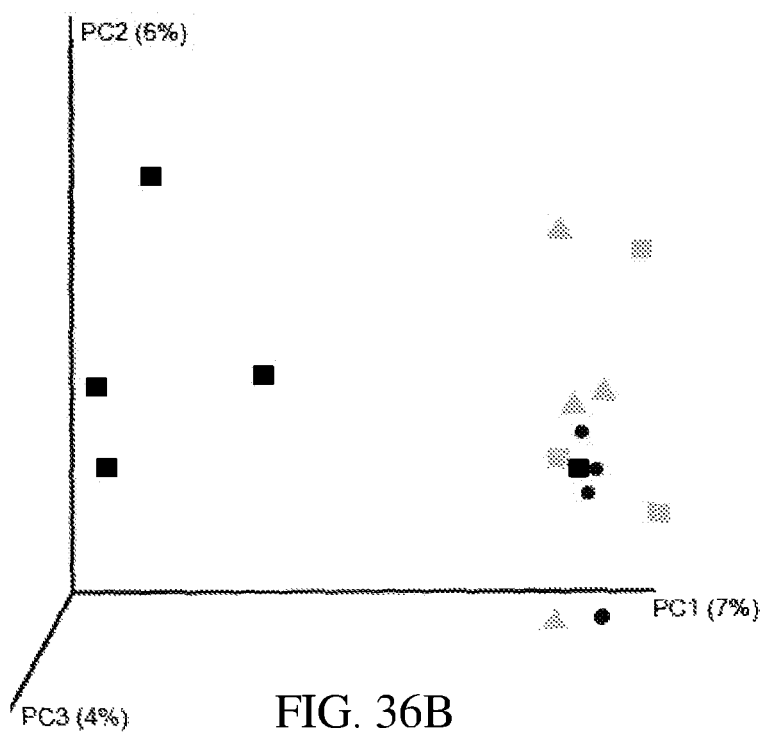
FIG. 36B is a PCA representing bacteria population in fecal samples of the mice of FIG. 36B 35 days after initiating CIA in the relevant groups (squares), and after treating the mice with TD-PC set forth in SEQ ID NO: 25 (gray square and gray triangle) or with a carrier (PBS; black square, black circle).

The results clearly indicate that microbiome profile of mice treated with TD-PC is similar to the microbiome profile of the healthy mice (FIG. 36B). Accordingly, the results suggest that the therapeutic effect exerted by TD-PC in CIA involves, inter alia, the ability of the conjugate to shift the microbiome of mice having CIA to a microbiome of healthy mice.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating or preventing an autoimmune disease in a subject in need thereof comprising administering to the subject a pharmaceutical composition comprising a phosphorylcholine-derivative bound directly to the C-terminus of an amino acid sequence whose C-terminus consists of TKPRGY (SEQ ID NO: 25) and wherein
   a. said phosphorylcholine derivative is any one of 4-amino-phenyl-phosphocholine, 4-diazonio-phenyl-phosphorylcholine, 4-nitro-phenyl-phosphocholine and 12-(3-iodophenyl)dodecyl-phosphocholine;
   b. said phosphorylcholine-derivative is bound to said C-terminus by an azo-bond; or
   c. both a and b.

2. The method of claim 1, wherein said phosphorylcholine-derivative is bound directly to the C-terminus of an amino acid sequence consisting of TKPRGY (SEQ ID NO: 25).

3. The method of claim 1, wherein said subject is at high risk of developing said autoimmune disease.

4. The method of claim 1, wherein said autoimmune disease is associated with abnormal inflammation.

5. The method of claim 1, wherein the autoimmune disease is selected from the group consisting of rheumatoid arthritis, lupus, multiple sclerosis, pemphigus vulgaris, antiphospholipid syndrome, psoriasis, autoimmune hepatitis, sarcoidosis, vasculitis, giant cell arteritis, inflammatory bowel disease, colitis, Crohn's disease and chronic obstructive pulmonary disease.

6. The method of claim 1, wherein the autoimmune disease is uveitis.

7. The method of claim 1, wherein the autoimmune disease is selected from the group consisting of arthritis, lupus, and colitis.

8. The method of claim 7, wherein the autoimmune disease is lupus.

9. The method of claim 7, wherein the autoimmune disease is arthritis.

10. The method of claim 9, wherein said arthritis is rheumatoid arthritis.

11. The method of claim 7, wherein the autoimmune disease is colitis.

12. The method of claim 11, wherein said colitis is inflammatory bowel disease (IBD) or Crohn's disease.

13. The method of claim 1, wherein said treating comprises at least one of preventing the onset of said autoimmune disease, attenuating the progress of said autoimmune disease and inhibiting the progression of said autoimmune disease.

14. The method of claim 1, wherein said treating comprises increasing T regulatory cells (Tregs) in said subject.

15. The method of claim 1, wherein said treating comprises decreasing proteinuria in said subject.

16. The method of claim 1, wherein said treating comprises decreasing glomerulonephritis in said subject.

17. The method of claim 1, wherein said treating comprises decreasing inflammation in said subject.

18. The method of claim 17, wherein decreasing inflammation comprises decreasing expression of at least one pro-inflammatory cytokine, increasing expression of at least one anti-inflammatory cytokine or both.

19. The method of claim 18, wherein said at least one pro-inflammatory cytokine is selected from the group consisting of: interferon gamma (IFNγ) and interleukin 17 (IL-17).

20. The method of claim 18, wherein said at least one anti-inflammatory cytokine is selected from the group consisting of: transforming growth factor beta (TGFβ) and interleukin 10(IL-10.

* * * * *